United States Patent
Elias et al.

(10) Patent No.: US 9,994,905 B2
(45) Date of Patent: Jun. 12, 2018

(54) METHODS FOR THE DIAGNOSIS AND TREATMENT OF PULMONARY FIBROSIS IN SUBJECTS WITH HERMANSKY PUDLAK SYNDROME

(71) Applicants: BROWN UNIVERSITY, Providence, RI (US); YALE UNIVERSITY, New Haven, CT (US)

(72) Inventors: Jack A. Elias, Providence, RI (US); Yang Zhou, Providence, RI (US); Chun Geun Lee, Providence, RI (US)

(73) Assignees: Brown University, Providence, RI (US); Yale University, New Haven, CT (US)

( * ) Notice: Subject to any disclaimer, the term of this patent is extended or adjusted under 35 U.S.C. 154(b) by 0 days. days.

(21) Appl. No.: 15/305,393

(22) PCT Filed: Apr. 24, 2015

(86) PCT No.: PCT/US2015/027481
§ 371 (c)(1),
(2) Date: Oct. 20, 2016

(87) PCT Pub. No.: WO2015/164716
PCT Pub. Date: Oct. 29, 2015

(65) Prior Publication Data
US 2017/0121773 A1  May 4, 2017

Related U.S. Application Data

(60) Provisional application No. 61/984,253, filed on Apr. 25, 2014, provisional application No. 62/081,701, filed on Nov. 19, 2014.

(51) Int. Cl.
*A61K 31/00* (2006.01)
*C12Q 1/68* (2018.01)
*G01N 33/573* (2006.01)

(52) U.S. Cl.
CPC ............ *C12Q 1/6883* (2013.01); *A61K 31/00* (2013.01); *C12Y 302/01014* (2013.01); *G01N 33/573* (2013.01); *C12Q 2600/158* (2013.01); *G01N 2333/924* (2013.01); *G01N 2800/12* (2013.01)

(58) Field of Classification Search
None
See application file for complete search history.

(56) References Cited

U.S. PATENT DOCUMENTS

| | | |
|---|---|---|
| 7,670,764 B2 | 3/2010 | Oh et al. |
| 2008/0171014 A1 | 7/2008 | Wu et al. |
| 2008/0194494 A1 | 8/2008 | Martinez et al. |
| 2008/0220003 A1 | 9/2008 | Schnatbaum et al. |
| 2013/0029873 A1 | 1/2013 | De Perrot et al. |

FOREIGN PATENT DOCUMENTS

WO  2013/148232 A1  10/2013

OTHER PUBLICATIONS

Areshkov et al.,"Two Closely Related Human Members of Chitinase-like Family, CHI3L1 and CHI3L2, Activate ERK1/2 in 293 and U373 Cells but Have the Different Influence on Cell Proliferation", Int. J. Biol. Sci. 8(1)39-48 (2012).
Chen et al., "Carbohydrate-binding motif in chitinase 3-like 1 (CHI3L1/YKL-40) specifically activates Akt signaling pathway in colonic epithelial cells", Clin Immunol. 140(3):268-275 (2011).
Coffman, "Chitinase 3-Like-1 (CHI3L1): A Putative Disease Marker at the Interface of Proteomics and Glycomics", Critical Reviews in Clinical Laboratory Sciences 45(6):531-562 (2008).
Dela Cruz et al., "Chitinase 3-like-1 Promotes *Streptococcus pneumoniae* Killing and Augments Host Tolerance to Lung Antibacterial Responses",Cell Host Microbe. 12(1):34-46 (2012).
Kim et al., "Involvement of the MAPK and PI3K pathways in chitinase 3-like 1-regulated hyperoxia-induced airway epithelial cell death", Biochemical and Biophysical Research Communications 421(4):790-796 (2012).
Lee et al., "Role of breast regression protein 39 (BRP-39)/chitinase 3-like-1 in Th2 and IL-13-induced tissue responses and apoptosis", J. Exp. Med. 206(5)1149-1166 (2009).
Lee et al., "Role of Chitin and Chitinase/Chitinase-Like Proteins in Inflammation, Tissue Remodeling, and Injury", Annu Rev Physiol. 73:479-501 (2011).
Lumsden et al., "Overexpression of IL-13Ra2 in the Mouse Lung Inhibits Induction of Fibrotic Markers in Bleomycin Induced Pulmonary Fibrosis", Am J Respir Crit Care Med. Confered. Abstract (2013).
Matsuura et al., "Role of Breast Regression Protein-39 in the Pathogenesis of Cigarette Smoke-Induced Inflammation and Emphysema", Am J Respir Cell Mol Biol. 44(6)177-786 (2011).
Sohn et al., "The Chitinase-like Proteins Breast Regression Protein-39 and YKL-40 Regulate Hyperoxia-Induced Acute Lung Injury", Am J Respir Crit Care Med. 182(7):918-928 (2010).
Zhou et al., "Chitinase 3-Like (CHI3L1) As a Biomarker and Therapeutic Target in the Pulmonary Fibrosis of Hermansky-Pudlak Syndrome", Am J Respir Crit Care Med. Meeting Abstract (2012).

*Primary Examiner* — Samantha L Shterengarts
(74) *Attorney, Agent, or Firm* — Nixon Peabody LLP; David S. Resnick; Nicole D. Kling

(57) ABSTRACT

Described herein are methods, assays, and systems related to the prognosis, diagnosis, and treatment of Hermansky Pudlak Syndrome (HPS) and, e.g., pulmonary fibrosis in a subject. As described herein, subjects with HPS who have, will develop, or are most at risk or developing pulmonary fibrosis have elevated levels of CHI3L1. In some embodiments, the methods comprise administering an agonist of IL-13Rα2 or an inhibitor of CRTH2 to the subject.

17 Claims, 13 Drawing Sheets

SEQUENCE LISTING

```
<160> NUMBER OF SEQ ID NOS: 10

<210> SEQ ID NO 1
<211> LENGTH: 1376
<212> TYPE: DNA
<213> ORGANISM: Homo sapiens

<400> SEQUENCE: 1
gtaagaacac tctcgtgagt ctaacggtct tccggatgaa ggctatttga agtcgccata      60
acctggtcag aagtgtgcct gtcggcgggg agagaggcaa tatcaaggtt ttaaatctcg     120
gagaaatggc tttcgtttgc ttggctatcg gatgcttata tacctttctg ataagcacaa     180
catttggctg tacttcatct tcagacaccg agataaaagt taaccctcct caggattttg     240
agatagtgga tcccggatac ttaggttatc tctatttgca atggcaaccc ccactgtctc     300
tggatcattt taaggaatgc acagtggaat atgaactaaa ataccgaaac attggtagtg     360
aaacatggaa gaccatcatt actaagaatc tacattacaa agatgggttt gatcttaaca     420
agggcattga agcgaagata cacacgcttt taccatggca atgcacaaat ggatcagaag     480
ttcaaagttc ctgggcagaa actacttatt ggatatcacc acaaggaatt ccagaaacta     540
aagttcagga tatggattgc gtatattaca attggcaata tttactctgt tcttggaaac     600
ctggcatagg tgtacttctt gataccaatt acaacttgtt ttactggtat gagggcttgg     660
atcatgcatt acagtgtgtt gattacatca aggctgatgg acaaaatata ggatgcagat     720
ttccctattt ggaggcatca gactataaag atttctatat ttgtgttaat ggatcatcag     780
agaacaagcc tatcagatcc agttatttca cttttcagct tcaaaatata gttaaacctt     840
tgccgccagt ctatcttact tttactcggg agagttcatg tgaaattaag ctgaaatgga     900
gcataccttt gggacctatt ccagcaaggt gttttgatta tgaaattgag atcagagaag     960
atgatactac cttggtgact gctacagttg aaaatgaaac atacacccttg aaaacaacaa    1020 atgaaacccg acaattatgc tttgtagtaa gaagcaaagt gaatatttat tgctcagatg    1080
acggaatttg gagtgagtgg agtgataaac aatgctggga aggtgaagac ctatcgaaga    1140
aaactttgct acgtttctgg ctaccatttg gtttcatctt aatattagtt atatttgtaa    1200
ccggtctgct tttgcgtaag ccaaacacct acccaaaaat gattccagaa tttttctgtg    1260
```

```
atacatgaag actttccata tcaagagaca tggtattgac tcaacagttt ccagtcatgg   1320
ccaaatgttc aatatgagtc tcaataaact gaatttttct tgcgaatgtt gaaaaa       1376
```

<210> SEQ ID NO 2
<211> LENGTH: 380
<212> TYPE: PRT
<213> ORGANISM: Homo sapiens

<400> SEQUENCE: 2

```
Met Ala Phe Val Cys Leu Ala Ile Gly Cys Leu Tyr Thr Phe Leu Ile
1               5                   10                  15

Ser Thr Thr Phe Gly Cys Thr Ser Ser Asp Thr Glu Ile Lys Val
            20                  25                  30

Asn Pro Pro Gln Asp Phe Glu Ile Val Asp Pro Gly Tyr Leu Gly Tyr
        35                  40                  45

Leu Tyr Leu Gln Trp Gln Pro Pro Leu Ser Leu Asp His Phe Lys Glu
    50                  55                  60

Cys Thr Val Glu Tyr Glu Leu Lys Tyr Arg Asn Ile Gly Ser Glu Thr
65                  70                  75                  80

Trp Lys Thr Ile Ile Thr Lys Asn Leu His Tyr Lys Asp Gly Phe Asp
                85                  90                  95

Leu Asn Lys Gly Ile Glu Ala Lys Ile His Thr Leu Leu Pro Trp Gln
            100                 105                 110

Cys Thr Asn Gly Ser Glu Val Gln Ser Ser Trp Ala Glu Thr Thr Tyr
        115                 120                 125

Trp Ile Ser Pro Gln Gly Ile Pro Glu Thr Lys Val Gln Asp Met Asp
    130                 135                 140

Cys Val Tyr Tyr Asn Trp Gln Tyr Leu Leu Cys Ser Trp Lys Pro Gly
145                 150                 155                 160

Ile Gly Val Leu Leu Asp Thr Asn Tyr Asn Leu Phe Tyr Trp Tyr Glu
                165                 170                 175

Gly Leu Asp His Ala Leu Gln Cys Val Asp Tyr Ile Lys Ala Asp Gly
            180                 185                 190

Gln Asn Ile Gly Cys Arg Phe Pro Tyr Leu Glu Ala Ser Asp Tyr Lys
        195                 200                 205

Asp Phe Tyr Ile Cys Val Asn Gly Ser Ser Glu Asn Lys Pro Ile Arg
    210                 215                 220

Ser Ser Tyr Phe Thr Phe Gln Leu Gln Asn Ile Val Lys Pro Leu Pro
225                 230                 235                 240

Pro Val Tyr Leu Thr Phe Thr Arg Glu Ser Ser Cys Glu Ile Lys Leu
                245                 250                 255

Lys Trp Ser Ile Pro Leu Gly Pro Ile Pro Ala Arg Cys Phe Asp Tyr
            260                 265                 270

Glu Ile Glu Ile Arg Glu Asp Asp Thr Thr Leu Val Thr Ala Thr Val
        275                 280                 285

Glu Asn Glu Thr Tyr Thr Leu Lys Thr Asn Glu Thr Arg Gln Leu
    290                 295                 300

Cys Phe Val Val Arg Ser Lys Val Asn Ile Tyr Cys Ser Asp Asp Gly
305                 310                 315                 320

Ile Trp Ser Glu Trp Ser Asp Lys Gln Cys Trp Glu Gly Glu Asp Leu
                325                 330                 335

Ser Lys Lys Thr Leu Leu Arg Phe Trp Leu Pro Phe Gly Phe Ile Leu
            340                 345                 350

Ile Leu Val Ile Phe Val Thr Gly Leu Leu Leu Arg Lys Pro Asn Thr
```

```
            355                 360                 365
Tyr Pro Lys Met Ile Pro Glu Phe Phe Cys Asp Thr
    370                 375                 380

<210> SEQ ID NO 3
<211> LENGTH: 2910
<212> TYPE: DNA
<213> ORGANISM: Homo sapiens

<400> SEQUENCE: 3
cagcctccct ctcccacctc tgtctgcccg ctgcctcttg tctagctgct gtcaggagct      60
gactgcctcc agggctggaa tcctgtgctc cctctgtgcc cagagcccca cgatgtcggc     120
caacgccaca ctgaagccac tctgccccat cctggagcag atgagccgtc tccagagcca     180
cagcaacacc agcatccgct acatcgacca cgcggccgtg ctgctgcacg ggctggcctc     240
gctgctgggc ctggtggaga tggagtcat cctcttcgtg gtgggctgcc gcatgcgcca     300
gaccgtggtc accacctggg tgctgcacct ggcgctgtcc gacctgttgg cctctgcttc     360
cctgcccttc ttcacctact tcttggccgt gggccactcg tgggagctgg caccaccctt     420
ctgcaaactg cactcctcca tcttctttct caacatgttc gccagcggct tcctgctcag     480
cgccatcagc ctggaccgct gcctgcaggt ggtgcggccg gtgtgggcgc agaaccaccg     540
caccgtggcc gcggcgcaca agtctgcct ggtgctttgg gcactagcgg tgctcaacac     600
ggtgccctat ttcgtgttcc gggacaccat ctcgcggctg acgggcgca ttatgtgcta     660 ctacaatgtg ctgctcctga cccgggggcc tgaccgcgat ccacgtgca actcgcggca     720 ggtggccctg ccgtcagca agttcctgct ggccttcctg tgccgctgg cgatcatcgc     780 ctcgagccac gcggccgtga gcctgcggtt gcagcaccgc ggccgccggc ggccaggccg     840
cttcgtgcgc ctggtggcgg ccgtcgtggc cgccttcgcg ctctgctggg ggcctacca     900 cgtgttcagc ctgctggagg cgcgggcgca cgcaaacccg gggctgcggc cgtcgtgtg     960 gcgcgggctg cccttcgtca ccagcctggc cttcttcaac agcgtggcca accggtgct    1020 ctacgtgctc acctgccccg acatgctgcg caagctgcgg cgctcgctgc cacggtgct    1080 ggagagcgtg ctggtggacg acagcgagct gggtggcgcg ggaagcagcc gccgccgccg    1140
cacctcctcc accgcccgct cggcctcccc tttagctctc tgcagccgcc cggaggaacc    1200
gcggggcccc gcgcgtctcc tcggctggct gctgggcagc tgcgcagcgt ccccgcagac    1260 gggcccctg aaccgggcgc tgagcagcac ctcgagttag aacccggccc acgtagggcg    1320
gcactcacac gcgaaagtat caccagggtg ccgcggttca attcgatatc cggactcctg    1380
ccgcagtgat caaagtccga ggggcgggac ccaggcacct gcattttaaa gcgccccggg    1440
agactctgaa tcttttcag aaacagtgag ttaaagcagt gcttctcaaa ccttgatgtg    1500
cctgtgaatc acctagggggt cttgttaagt gcagtctgat ccaggaggcc ggggccgggt    1560
actgagagtc tgcacttaac aagctcccag gccgagaagc cagtgcggca ggttcacagg    1620
cgaggcctgg agtaacacaa agtgaaactc ataatagact tcccactcta gggcagtgga    1680
gtcggaaggg cacacggggt gcgtctcccc ggagttcagt tttaccagat gatggggag    1740 gggggaagga gttttatgtt aaaccatcca tgtatttttg gagaagagag aggaaaggtt    1800
tgagaagcac tgttccagcc tgccctcttc atttagccaa tgcttactgc gctagacgct    1860
tcatcccaca atcttaaggg gcagcttcta ttagccagtc tttacagctg agcacattct    1920
ggctcaggga ggttaagtga cttgcccagt ttcagggcta acgaccacag ggtctgcact    1980
```

| | | |
|---|---|---|
| ctaaccctag gcatcacatg ctcaatgact ctctggtgag cgaggacatt ctctgaccta | 2040 |
| ctcgagggac ttaagatgct accttgtgac ccagcactgc ccaaagtgct tccaaggcag | 2100 |
| aagcagcagg ggatggcgtg gtcaagcact cgggaaacct ggggctaatc aaatccaatg | 2160 |
| ggggaaatga ctaaaagtct tcggtcgtta gaagttgaat gggcacagca actctaagac | 2220 |
| tacagcacac gtcatttctt agctaagcgg accagcctcc ctgtcggcct ggtgttctgt | 2280 |
| gggatccctc tggcactgg taatcccaag atctgtgcag ccccgcctcc aggccacatg | 2340 |
| gggctgggca gctaccattt ccctttttgcg gatgggaggg gtaacttgca cctctgacct | 2400 |
| atcacttcca ctgcaccccg tctcattcct ccacctgccg tggacttggg gtcagagact | 2460 |
| gctgtgtttg agctctgcag cccagggacc gaaaagttgg tgtcaatgaa ttttgcttgg | 2520 |
| tggatgaaat gtcagtggaa gaagcagatg agaaactctt gagatcttgg tcctgtgttt | 2580 |
| tttctgccac caaaggccag ggtcactgaa ggcctggccc acagcaggtg ctgagcaaag | 2640 |
| ggaacagtga ggtgcccagc tagctgcaga gccaccctgt gttgacacct cgcccctgct | 2700 |
| ccctcccatc ccttccccct ttactcatag cacttccccc attggacacg tggtgcattt | 2760 |
| tgcttgttta ttatgttttc tctccatcag aatgaaagct cctcgagggc agggactttg | 2820 |
| gtctattgtc tgtatttgcc ggtgcctagg attgtgcctg tatgcaacag gcactcaata | 2880 |
| aatattttg ctgtagactg gacaggcatg | 2910 |

<210> SEQ ID NO 4
<211> LENGTH: 395
<212> TYPE: PRT
<213> ORGANISM: Homo sapiens

<400> SEQUENCE: 4

Met Ser Ala Asn Ala Thr Leu Lys Pro Leu Cys Pro Ile Leu Glu Gln
1               5                   10                  15

Met Ser Arg Leu Gln Ser His Ser Asn Thr Ser Ile Arg Tyr Ile Asp
            20                  25                  30

His Ala Ala Val Leu Leu His Gly Leu Ala Ser Leu Leu Gly Leu Val
        35                  40                  45

Glu Asn Gly Val Ile Leu Phe Val Val Gly Cys Arg Met Arg Gln Thr
    50                  55                  60

Val Val Thr Thr Trp Val Leu His Leu Ala Leu Ser Asp Leu Leu Ala
65                  70                  75                  80

Ser Ala Ser Leu Pro Phe Phe Thr Tyr Phe Leu Ala Val Gly His Ser
                85                  90                  95

Trp Glu Leu Gly Thr Thr Phe Cys Lys Leu His Ser Ser Ile Phe Phe
            100                 105                 110

Leu Asn Met Phe Ala Ser Gly Phe Leu Leu Ser Ala Ile Ser Leu Asp
        115                 120                 125

Arg Cys Leu Gln Val Val Arg Pro Val Trp Ala Gln Asn His Arg Thr
    130                 135                 140

Val Ala Ala Ala His Lys Val Cys Leu Val Leu Trp Ala Leu Ala Val
145                 150                 155                 160

Leu Asn Thr Val Pro Tyr Phe Val Phe Arg Asp Thr Ile Ser Arg Leu
                165                 170                 175

Asp Gly Arg Ile Met Cys Tyr Tyr Asn Val Leu Leu Leu Asn Pro Gly
            180                 185                 190

Pro Asp Arg Asp Ala Thr Cys Asn Ser Arg Gln Val Ala Leu Ala Val
        195                 200                 205

-continued

```
Ser Lys Phe Leu Leu Ala Phe Leu Val Pro Leu Ala Ile Ile Ala Ser
    210                 215                 220

Ser His Ala Ala Val Ser Leu Arg Leu Gln His Arg Gly Arg Arg
225                 230                 235                 240

Pro Gly Arg Phe Val Arg Leu Val Ala Ala Val Ala Ala Phe Ala
                245                 250                 255

Leu Cys Trp Gly Pro Tyr His Val Phe Ser Leu Leu Glu Ala Arg Ala
                260                 265                 270

His Ala Asn Pro Gly Leu Arg Pro Leu Val Trp Arg Gly Leu Pro Phe
            275                 280                 285

Val Thr Ser Leu Ala Phe Phe Asn Ser Val Ala Asn Pro Val Leu Tyr
290                 295                 300

Val Leu Thr Cys Pro Asp Met Leu Arg Lys Leu Arg Arg Ser Leu Arg
305                 310                 315                 320

Thr Val Leu Glu Ser Val Leu Val Asp Asp Ser Glu Leu Gly Gly Ala
                325                 330                 335

Gly Ser Ser Arg Arg Arg Arg Thr Ser Ser Thr Ala Arg Ser Ala Ser
            340                 345                 350

Pro Leu Ala Leu Cys Ser Arg Pro Glu Glu Pro Arg Gly Pro Ala Arg
            355                 360                 365

Leu Leu Gly Trp Leu Leu Gly Ser Cys Ala Ala Ser Pro Gln Thr Gly
370                 375                 380

Pro Leu Asn Arg Ala Leu Ser Ser Thr Ser Ser
385                 390                 395
```

<210> SEQ ID NO 5
<211> LENGTH: 1867
<212> TYPE: DNA
<213> ORGANISM: Homo sapiens

<400> SEQUENCE: 5

```
cacatagctc agttcccata aaagggctgg tttgccgcgt cggggagtgg agtgggacag      60
gtatataaag gaagtacagg gcctggggaa gaggccctgt ctaggtagct ggcaccagga     120
gccgtgggca agggaagagg ccacaccctg ccctgctctg ctgcagccag aatgggtgtg     180
aaggcgtctc aaacaggctt gtggtcctg gtgctgctcc agtgctgctc tgcatacaaa      240
ctggtctgct actacaccag ctggtcccag taccgggaag cgatgggagc tgcttccca      300
gatgcccttg accgcttcct ctgtacccac atcatctaca gctttgccaa tataagcaac     360
gatcacatcg acacctggga gtggaatgat gtgacgctct acggcatgct caacacactc     420
aagaacagga accccaacct gaagactctc ttgtctgtcg aggatggaa ctttgggtct      480
caaagatttt ccaagatagc ctccaacacc cagagtcgcc ggactttcat caagtcagta     540
ccgccatttc tgcgcaccca tggctttgat gggctggacc ttgcctggct ctaccctgga     600
cggagagaca acagcattt taccacccta atcaaggaaa tgaaggccga atttataaag     660
gaagcccagc cagggaaaaa gcagctcctg ctcagcgcag cactgtctgc ggggaaggtc     720
accattgaca gcagctatga cattgccaag atatcccaac acctggattt cattagcatc     780
atgacctacg atttcatgg agcctggcgt gggaccacag ccatcacag tcccctgttc      840
cgaggtcagg aggatgcaag tcctgacaga ttcagcaaca ctgactatgc tgtgggtac      900
atgttgaggc tggggctcc tgccagtaag ctggtgatgg catcccac cttcgggagg        960
agcttcactc tggcttcttc tgagactggt gttgagccc caatctcagg accgggaatt    1020
ccaggccggt tcaccaagga ggcagggacc cttgcctact atgagatctg tgacttcctc    1080
```

-continued

```
cgcggagcca cagtccatag aatcctcggc cagcaggtcc cctatgccac caagggcaac    1140
cagtgggtag gatacgacga ccaggaaagc gtcaaaagca aggtgcagta cctgaaggac    1200
aggcagctgg cgggcgccat ggtatgggcc ctggacctgg atgacttcca gggctccttc    1260
tgcggccagg atctgcgctt ccctctcacc aatgccatca aggatgcact cgctgcaacg    1320
tagccctctg ttctgcacac agcacggggg ccaaggatgc cccgtccccc tctggctcca    1380
gctggccggg agcctgatca cctgccctgc tgagtcccag gctgagcctc agtctccctc    1440
ccttggggcc tatgcagagg tccacaacac acagatttga gctcagccct ggtgggcaga    1500
gaggtaggga tggggctgtg gggatagtga ggcatcgcaa tgtaagactc gggattagta    1560
cacacttgtt gattaatgga aatgtttaca gatccccaag cctggcaagg gaatttcttc    1620
aactccctgc cccccagccc tccttatcaa aggacaccat tttggcaagc tctatcacca    1680
aggagccaaa catcctacaa gacacagtga ccatactaat tataccccct gcaaagccca    1740
gcttgaaacc ttcacttagg aacgtaatcg tgtcccctat cctacttccc cttcctaatt    1800
ccacagctgc tcaataaagt acaagagctt aacagtgaaa aaaaaaaaa aaaaaaaaa    1860 aaaaaaa                                                             1867
```

<210> SEQ ID NO 6
<211> LENGTH: 383
<212> TYPE: PRT
<213> ORGANISM: Homo sapiens
<400> SEQUENCE: 6

```
Met Gly Val Lys Ala Ser Gln Thr Gly Phe Val Val Leu Val Leu Leu
1               5                   10                  15

Gln Cys Cys Ser Ala Tyr Lys Leu Val Cys Tyr Tyr Thr Ser Trp Ser
            20                  25                  30

Gln Tyr Arg Glu Gly Asp Gly Ser Cys Phe Pro Asp Ala Leu Asp Arg
        35                  40                  45

Phe Leu Cys Thr His Ile Ile Tyr Ser Phe Ala Asn Ile Ser Asn Asp
    50                  55                  60

His Ile Asp Thr Trp Glu Trp Asn Asp Val Thr Leu Tyr Gly Met Leu
65                  70                  75                  80

Asn Thr Leu Lys Asn Arg Asn Pro Asn Leu Lys Thr Leu Leu Ser Val
                85                  90                  95

Gly Gly Trp Asn Phe Gly Ser Gln Arg Phe Ser Lys Ile Ala Ser Asn
            100                 105                 110

Thr Gln Ser Arg Arg Thr Phe Ile Lys Ser Val Pro Pro Phe Leu Arg
        115                 120                 125

Thr His Gly Phe Asp Gly Leu Asp Leu Ala Trp Leu Tyr Pro Gly Arg
    130                 135                 140

Arg Asp Lys Gln His Phe Thr Thr Leu Ile Lys Glu Met Lys Ala Glu
145                 150                 155                 160

Phe Ile Lys Glu Ala Gln Pro Gly Lys Lys Gln Leu Leu Leu Ser Ala
                165                 170                 175

Ala Leu Ser Ala Gly Lys Val Thr Ile Asp Ser Ser Tyr Asp Ile Ala
            180                 185                 190

Lys Ile Ser Gln His Leu Asp Phe Ile Ser Ile Met Thr Tyr Asp Phe
        195                 200                 205

His Gly Ala Trp Arg Gly Thr Thr Gly His His Ser Pro Leu Phe Arg
    210                 215                 220
```

Gly Gln Glu Asp Ala Ser Pro Asp Arg Phe Ser Asn Thr Asp Tyr Ala
225                 230                 235                 240

Val Gly Tyr Met Leu Arg Leu Gly Ala Pro Ala Ser Lys Leu Val Met
            245                 250                 255

Gly Ile Pro Thr Phe Gly Arg Ser Phe Thr Leu Ala Ser Ser Glu Thr
            260                 265                 270

Gly Val Gly Ala Pro Ile Ser Gly Pro Gly Ile Pro Gly Arg Phe Thr
        275                 280                 285

Lys Glu Ala Gly Thr Leu Ala Tyr Tyr Glu Ile Cys Asp Phe Leu Arg
    290                 295                 300

Gly Ala Thr Val His Arg Ile Leu Gly Gln Gln Val Pro Tyr Ala Thr
305                 310                 315                 320

Lys Gly Asn Gln Trp Val Gly Tyr Asp Asp Gln Glu Ser Val Lys Ser
            325                 330                 335

Lys Val Gln Tyr Leu Lys Asp Arg Gln Leu Ala Gly Ala Met Val Trp
            340                 345                 350

Ala Leu Asp Leu Asp Asp Phe Gln Gly Ser Phe Cys Gly Gln Asp Leu
        355                 360                 365

Arg Phe Pro Leu Thr Asn Ala Ile Lys Asp Ala Leu Ala Ala Thr
    370                 375                 380

<210> SEQ ID NO 7
<211> LENGTH: 1234
<212> TYPE: DNA
<213> ORGANISM: Homo sapiens

<400> SEQUENCE: 7
gggccgcgag cactggcggg ttctgggtcc tgtgaccggt caggcggcgt cagcgggcgc      60
ggcggagggc tggccggcct cgggggagtt tccgcggccg ccgggggcgc ggcggcagag     120
cgcgaggccg ggcagggggc cagactcgga gtcgaggcgc gcccgacagc cgcagcgctc     180
atggcgggcg gaggagccgg ggaccccggc ctggggcgg ccgccgcccc agcgcccgag     240
acccgcgagc acctcttcaa ggtgctggtg atcggcgagc ttggcgtggg caagaccagc     300
atcatcaagc gctacgtcca ccagctcttc tcccagcact accgggccac catcgggtg      360 gacttcgccc tcaaggtcct caactgggac agcaggactc tggtgcgcct gcagctgtgg     420
gacatcgcgg ggcaggagcg atttggcaac atgacccgag tatactacaa ggaagctgtt     480 ggtgctttg tagtctttga tatatcaaga agttccacat ttgaggcagt cttaaaatgg     540
aaaagtgatc tggatagtaa agttcatctt ccaaatggca gccctatccc tgctgtcctc     600
ttggctaaca aatgtgacca gaacaaggac agtagccaga gtccttccca ggtggaccaa     660
ttctgcaaag aacatggctt tgccggatgg tttgaaacct ctgcaaagga taacataaac     720
atagaggaag ctgcccggtt cctagtggag aagattcttg taaaccacca aagctttcct     780
aatgaagaaa acgatgtgga caaaattaag ctagatcaag agaccttgag agcagagaac     840
aaatcccagt gttgctgata tatggcttct gcttctcttg tgtgtgcctc agctctgaag     900
aagttcctga aatgggtta cagatgtcat gttagctggg agtcttccca catgtggcac     960
ttcaaaaggc agcaccactg ggcgcctgca cttatttgaa aatggaactt tgggagaagt    1020
atccctgcta gtggctctgt aacttaacag atgacaatta ggcttttgtc attgttgcca    1080
tcatatggaa gataatgttt acatcctttt aaacattttt atatgacaat tcctcaggat    1140
ttggtaaggc ttccaagttg tagcttttag tgtaagtgct ggggtggtaa taaaatgtta    1200
cctgcaaaaa aaaaaaaaaa aaaaaaaaaa aaaa                                1234

<210> SEQ ID NO 8
<211> LENGTH: 225
<212> TYPE: PRT
<213> ORGANISM: Homo sapiens

<400> SEQUENCE: 8

Met Ala Gly Gly Ala Gly Asp Pro Gly Leu Gly Ala Ala Ala Ala
1               5                   10                  15

Pro Ala Pro Glu Thr Arg Glu His Leu Phe Lys Val Leu Val Ile Gly
            20                  25                  30

Glu Leu Gly Val Gly Lys Thr Ser Ile Ile Lys Arg Tyr Val His Gln
        35                  40                  45

Leu Phe Ser Gln His Tyr Arg Ala Thr Ile Gly Val Asp Phe Ala Leu
    50                  55                  60

Lys Val Leu Asn Trp Asp Ser Arg Thr Leu Val Arg Leu Gln Leu Trp
65                  70                  75                  80

Asp Ile Ala Gly Gln Glu Arg Phe Gly Asn Met Thr Arg Val Tyr Tyr
                85                  90                  95

Lys Glu Ala Val Gly Ala Phe Val Val Phe Asp Ile Ser Arg Ser Ser
            100                 105                 110

Thr Phe Glu Ala Val Leu Lys Trp Lys Ser Asp Leu Asp Ser Lys Val
        115                 120                 125

His Leu Pro Asn Gly Ser Pro Ile Pro Ala Val Leu Leu Ala Asn Lys
    130                 135                 140

Cys Asp Gln Asn Lys Asp Ser Ser Gln Ser Pro Ser Gln Val Asp Gln
145                 150                 155                 160

Phe Cys Lys Glu His Gly Phe Ala Gly Trp Phe Glu Thr Ser Ala Lys
                165                 170                 175

Asp Asn Ile Asn Ile Glu Glu Ala Ala Arg Phe Leu Val Glu Lys Ile
            180                 185                 190

Leu Val Asn His Gln Ser Phe Pro Asn Glu Glu Asn Asp Val Asp Lys
        195                 200                 205

Ile Lys Leu Asp Gln Glu Thr Leu Arg Ala Glu Asn Lys Ser Gln Cys
    210                 215                 220

Cys
225

<210> SEQ ID NO 9
<211> LENGTH: 1479
<212> TYPE: DNA
<213> ORGANISM: Homo sapiens

<400> SEQUENCE: 9
ttgcgctccc caagtctctc tcgtgcgcag agcccaggct gcgcttccct ggtcaggcac    60
ggcacgtctg gccggccgcc aggatgcagg ccccgcacaa ggagcacctg tacaagttgc   120
tggtgattgg cgacctgggc gtggggaaga ccagtatcat caagcgctac gtgcaccaga   180
acttctcttc gcactaccgg gccacaatcg gcgtggactt cgcgctcaag gtgctccact   240
gggacccgga gactgtggtg cgcctgcagc tctgggatat cgcaggtcaa gaaagatttg   300
gaaacatgac gagggtctat taccgagaag ctatgggtgc atttattgtc ttcgatgtca   360
ccaggccagc cacatttgaa gcagtggcaa agtggaaaaa tgatttggac tccaagttaa   420
gtctccctaa tggcaaaccg gtttcagtgg ttttgttggc caacaaatgt gaccagggga   480
aggatgtgct catgaacaat ggcctcaaga tggaccagtt ctgcaaggag cacgtgtttcg   540

```
taggatggtt tgaaacatca gcaaaggaaa atataaacat tgatgaagcc tccagatgcc    600
tggtgaaaca catacttgca aatgagtgtg acctaatgga gtctattgag ccggacgtcg    660
tgaagcccca tctcacatca accaaggttg ccagctgctc tggctgtgcc aaatcctagt    720
aggcaccttt gctggtgtct ggtaggaatg acctcattgt tccacaaatt gtgcctctat    780
ttttaccatt tgggtaaac gtcaggatag agataccaca tgtggcaagc caagatcta     840
tgcctctgtt ttttcagtga gagagaaata gcaaatgttc tttctatgct ttcctcacca    900
tcatcacagt gtttacaaac ttttgaaaat atttagtctg ttacaaactt ctgtcatgta    960
gctgaccaaa atcctgcagg ccacagtcg gcactgttat ttgcttcttt taatcagcaa    1020
aggcctcaag tcttaaaata aaggggaga agaacaaact agctgtcaag tcaaggactg     1080
gctttcacct tgccctggtg tcttttcca gatttcagta tattctctga tggcctgaca    1140
ggcctattaa gtagatgtga tattttctcc caagatgacc tccattctcg gcagacctaa    1200
gagttgcctc tgagttagct ctttggaatc gtgaacacag gtgtgctata ttgtccttgt    1260
cctaactgtc acttgccatg gcctgaatgt tggcttaact gaatattgta tgaaaagaca    1320
tgcctccata tgtgcctttc tgttagcttt ctctgactca agctgtgggg ctcctctata    1380
catgctatac atgtaatata tattatatat atttttgcaa gtgaacaata aacattaaa     1440
agatgctgtt tccctattta aaaaaaaaa aaaaaaaa                             1479

<210> SEQ ID NO 10
<211> LENGTH: 211
<212> TYPE: PRT
<213> ORGANISM: Homo sapiens

<400> SEQUENCE: 10

Met Gln Ala Pro His Lys Glu His Leu Tyr Lys Leu Leu Val Ile Gly
1               5                   10                  15

Asp Leu Gly Val Gly Lys Thr Ser Ile Ile Lys Arg Tyr Val His Gln
            20                  25                  30

Asn Phe Ser Ser His Tyr Arg Ala Thr Ile Gly Val Asp Phe Ala Leu
        35                  40                  45

Lys Val Leu His Trp Asp Pro Glu Thr Val Val Arg Leu Gln Leu Trp
    50                  55                  60

Asp Ile Ala Gly Gln Glu Arg Phe Gly Asn Met Thr Arg Val Tyr Tyr
65                  70                  75                  80

Arg Glu Ala Met Gly Ala Phe Ile Val Phe Asp Val Thr Arg Pro Ala
                85                  90                  95

Thr Phe Glu Ala Val Ala Lys Trp Lys Asn Asp Leu Asp Ser Lys Leu
            100                 105                 110

Ser Leu Pro Asn Gly Lys Pro Val Ser Val Val Leu Leu Ala Asn Lys
        115                 120                 125

Cys Asp Gln Gly Lys Asp Val Leu Met Asn Asn Gly Leu Lys Met Asp
    130                 135                 140

Gln Phe Cys Lys Glu His Gly Phe Val Gly Trp Phe Glu Thr Ser Ala
145                 150                 155                 160

Lys Glu Asn Ile Asn Ile Asp Glu Ala Ser Arg Cys Leu Val Lys His
                165                 170                 175

Ile Leu Ala Asn Glu Cys Asp Leu Met Glu Ser Ile Glu Pro Asp Val
            180                 185                 190
```

```
Val Lys Pro His Leu Thr Ser Thr Lys Val Ala Ser Cys Ser Gly Cys
        195                 200                 205
Ala Lys Ser
    210
```

METHODS FOR THE DIAGNOSIS AND TREATMENT OF PULMONARY FIBROSIS IN SUBJECTS WITH HERMANSKY PUDLAK SYNDROME

CROSS-REFERENCE TO RELATED APPLICATIONS

This application is a 35 U.S.C. § 371 National Phase Entry Application of International Application No. PCT/US2015/027481 filed Apr. 24, 2015, which designates the U.S. and claims benefit under 35 U.S.C. § 119(e) of U.S. Provisional Application Nos. 61/984,253 filed Apr. 25, 2014 and 62/081,701 filed Nov. 19, 2014, the contents of which are incorporated herein by reference in their entirety.

GOVERNMENT SUPPORT

This invention was made with government support under R01 HL093017 and U01 HL108638 awarded by National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on Feb. 20, 2015, is named 058040-080672-PCT_SL.txt and is 26,270 bytes in size.

TECHNICAL FIELD

The technology described herein relates to the diagnosis, prognosis, and treatment of pulmonary fibrosis, e.g. in subjects with Hermansky Pudlak Syndrome.

BACKGROUND

Hermansky-Pudlak Syndrome (HPS) is a group of inherited autosomal recessive disorders characterized by mutations affecting the function of lysosome-related organelles (LROs). Patients with HPS often suffer from oculocutaneous albinism, visual impairment, bleeding disorders, and/or inflammatory bowel disease. More importantly, untreatable and progressive pulmonary fibrosis occurs in certain HPS patients, and is the leading cause of death in such patients (Pierson, D. M., et al. *Respiration* 73, 382-395 (2006)). There are currently no methods to predict which patients will experience pulmonary fibrosis. In addition, little is known about the mechanisms that drive the lung injury and the progressive fibrotic response in HPS patients, and no therapeutics successfully intervene in these responses.

SUMMARY

Described herein is the inventors' discovery that pulmonary fibrosis in subjects with HPS is caused by an unchecked ability of CHI3L1 to signal via CRTH2 and a decreased ability and/or sensitivity of CHI3L1 to signal via IL-13Rα2. This aberrant state of affairs leads to a decrease of the ability of CHI3L1 to prevent cell death and an increase in the ability of CHI3L1 to induce proliferation of fibroblasts and fibrosis. This understanding of the pathology of pulmonary fibrosis in HPS patients permits methods of prognosis, diagnosis, and treatment as described herein.

In one aspect, described herein is a method of treating Hermansky Pudlak Syndrome (HPS) in a subject in need thereof, the method comprising administering an agonist of IL-13Rα2 or an inhibitor of CRTH2 to the subject. In one aspect, described herein is a method of treating pulmonary fibrosis in a subject in need of treatment for Hermansky Pudlak Syndrome (HPS), the method comprising administering an agonist of IL-13Rα2 or an inhibitor of CRTH2 to the subject. In some embodiments, the subject is a subject identified as having an increased level of CHI3L1 expression and/or activity.

In one aspect, described herein is a method comprising: measuring the level of CHI3L1 in a test sample obtained from a subject with Hermansky Pudlak Syndrome (HPS); wherein an increase in the CHI3L1 level relative to a reference level indicates the subject has a higher risk of having or developing pulmonary fibrosis. In one aspect, described herein is an assay comprising contacting a sample obtained from the subject with Hermansky Pudlak Syndrome (HPS) with a CHI3L1-specific reagent to detect the presence or level of CHI3L1; measuring the presence or intensity of a signal which indicates the presence or level of CHI3L1 in the sample; wherein an increase in the CHI3L1 level relative to a reference level indicates the subject has a higher risk of having or developing pulmonary fibrosis. In one aspect, described herein is a method for selecting a treatment regimen for a subject with Hermansky Pudlak Syndrome (HPS), comprising: contacting a sample obtained from the subject with Hermansky Pudlak Syndrome (HPD) with a CHI3L1-specific reagent to detect the presence or level of CHI3L1; measuring the presence or intensity of a signal which indicates the presence or level of CHI3L1 in the sample; selecting a treatment regimen comprising a treatment for pulmonary fibrosis when the subject has an increase in the CHI3L1 level relative to a reference level; and selecting a treatment regimen not comprising a treatment for pulmonary fibrosis when the subject does not have an increase in the CHI3L1 level relative to a reference level. In one aspect, described herein is a method of identifying a subject with Hermansky Pudlak Syndrome (HPS) in need of treatment for pulmonary fibrosis, the method comprising: measuring the level of CHI3L1 in a test sample obtained from a subject; and identifying the subject as being in need of treatment for pulmonary fibrosis when the expression level of CHI3L1 is increased relative to a reference level. In one aspect, described herein is a method of determining if a subject with Hermansky Pudlak Syndrome (HPS) is at risk for pulmonary fibrosis, the method comprising: measuring the level of CHI3L1 in a test sample obtained from a subject; comparing the level of CHI3L1 in the sample to a reference level of CHI3L1; determining that the subject is at risk for pulmonary fibrosis when the level of CHI3L1 is increased relative to a reference level; and determining that the subject is not at risk for pulmonary fibrosis when the level of CHI3L1 is not increased relative to a reference level. In one aspect, described herein is a method of determining the efficacy of a treatment for pulmonary fibrosis in a subject with Hermansky Pudlak Syndrome (HPS), the method comprising: a) measuring the level of CHI3L1 in a test sample obtained from a subject before administration of the treatment; b) measuring the level of CHI3L1 in a test sample obtained from a subject after administration of the treatment; and c) determining that the treatment is not efficacious when the expression level determined in step (b) is increased relative to the expression level determined in step (a). In one aspect, described herein is a method of treatment for pulmonary fibrosis in a subject with Hermansky Pudlak Syndrome, the method comprising; measuring the level of CHI3L1 in a test sample obtained from a subject; treating the subject with a pulmonary fibrosis treatment when the level of CHI3L1 is increased relative to a reference level; and not treating the subject with a pulmonary fibrosis treatment when the level of CHI3L1 is not increased relative to a reference level.

In some embodiments of any of the foregoing aspects, the sample obtained from the subject is a blood, plasma or serum sample. In some embodiments of any of the foregoing aspects, a detectable signal is generated by a CHI3L1-specific reagent when a CHI3L1 molecule is present. In some embodiments of any of the foregoing aspects, the CHI3L1-specific reagent is detectably labeled or capable of generating a detectable signal. In some embodiments of any of the foregoing aspects, the treatment for pulmonary fibrosis is an agonist of IL-13Rα2 and/or an inhibitor of CRTH2. In some embodiments of any of the foregoing aspects, the agonist of IL-13Rα2 is an agonist of Rab32/38. In some embodiments of any of the foregoing aspects, the inhibitor of CRTH2 is selected from the group consisting of: OC-459; AZD-1981; Setipiprant; QAW-039; QAV-680; MK-7246; ADC-3680; BI671800; ARRY-502; RG-7581; AZD-5985; AZD-8075; AM461; AM211; AMG-853; $PGD_2$; AM432; CAY-10471; TM-30089; TM-30643; TM-30642; Ramatroban; and OC000459.

In some embodiments of any of the foregoing aspects, the level of CHI3L1 is determined by measuring the level of a nucleic acid. In some embodiments of any of the foregoing aspects, the level of CHI3L1 is determined by determined the level of CHI3L1 RNA transcript. In some embodiments of any of the foregoing aspects, the level of the nucleic acid is determined using a method selected from the group consisting of: RT-PCR; quantitative RT-PCR; Northern blot; microarray based expression analysis; next-generation sequencing; and RNA in situ hybridization.

In some embodiments of any of the foregoing aspects, the level of CHI3L1 is determined by measuring the level of CHI3L1 polypeptide. In some embodiments of any of the foregoing aspects, the level of the polypeptide is determined using a method selected from the group consisting of: Western blot; immunoprecipitation; enzyme-linked immunosorbent assay (ELISA); radioimmunological assay (RIA); sandwich assay; fluorescence in situ hybridization (FISH); immunohistological staining; radioimmunometric assay; immunofluoresence assay; mass spectroscopy; FACS; and immunoelectrophoresis assay. In some embodiments of any of the foregoing aspects, the polypeptide level is measured using an antibody reagent. In some embodiments of any of the foregoing aspects, the antibody reagent is detectably labeled or generates a detectable signal.

In some embodiments of any of the foregoing aspects, the expression level of CHI3L1 is normalized relative to the expression level of one or more reference genes or reference proteins. In some embodiments of any of the foregoing aspects, the reference level of CHI3L1 is the expression level of CHI3L1 in a prior sample obtained from the subject.

In one aspect, described herein is a kit for performing the method or assay described herein.

In one aspect, described herein is a computer system for determining the risk of a subject with Hermansky Pudlak Syndrome (HPS) having or developing pulmonary fibrosis, the system comprising: a measuring module configured to measure the level of CHI3L1 in a test sample obtained from a subject; a storage module configured to store output data from the determination module; a comparison module adapted to compare the data stored on the storage module with a reference level, and to provide a retrieved content, and a display module for displaying whether the sample comprises a level of CHI3L1 which is significantly increased relative to the reference expression level and/or displaying the relative level of CHI3L1. In some embodiments, the measuring module measures the intensity of a detectable signal from an assay indicating the level of CHI3L1 polypeptide in the test sample. In some embodiments, the assay is an immunoassay. In some embodiments, the measuring module measures the intensity of a detectable signal from a RT-PCR assay indicating the level of CHI3L1 RNA transcript in the test sample. In some embodiments, if the computing module determines that the level of CHI3L1 in the test sample obtained from a subject is greater by a statistically significant amount than the reference level, the display module displays a signal indicating that the levels in the sample obtained from a subject are greater than those of the reference level. In some embodiments, the signal indicates that the subject has an increased likelihood of having or developing pulmonary fibrosis. In some embodiments, the signal indicates the subject is in need of treatment for pulmonary fibrosis. In some embodiments, the signal indicates the degree to which the level of CHI3L1 in the sample obtained from a subject varies from the reference level.

BRIEF DESCRIPTION OF THE DRAWINGS

FIG. 1A depicts a graph demonstrating that plasma CHI3L1 is increased in HPS-1 and HPS-4 patients compared to age-matched normal controls. FIG. 1B depicts a graph demonstrating that plasma CHI3L1 is increased in HPS-1 and HPS-4 patients compared to HPS-3, HPS-5, and HPS-6 patients. FIG. 1C depicts a graph demonstrating that plasma CHI3L1 is increased in HPS-1 and HPS-4 patients with lung disease. FIG. 1D depicts a graph demonstrating that plasma CHI3L1 is higher in patients with severe disease according to FVC. FIG. 1E depicts a graph demonstrating that plasma CHI3L1 is higher in patients with severe disease according to DLCO. FIG. 1F depicts a graph demonstrating that plasma CHI3L1 levels correlate with FVC. FIG. 1G (G) Plasma CHI3L1 levels correlate with DLCO.*$p \leq 0.05$,$p \leq 0.05$,*$p \leq 0.001$, ****$p \leq 0.0001$.

FIG. 2A depicts a graph of CHI3L1 transcript measured in whole-lung RNA extracts from WT and pale ear mice using qRT-PCR. FIG. 2B depicts a graph of CHI3L1 protein levels in BAL fluid quantified using ELISA. Values are mean±SEM with a minimum of 4 mice in each group **$p \leq 0.01$,*$p \leq 0.05$.

FIGS. 3A and 3B depict graphs of experiments in which WT and pale ear mice were subjected to intratracheal saline or bleomycin administration. FIG. 3A depicts the results of TUNEL staining performed on Day 7 and TUNEL-positive Type II epithelial cells were counted. FIG. 3B depicts quantification of total lung collagen using Sircol assay on Day 14. In FIGS. 3C-3F, WT, $CHI3L1^{-/-}$, pale ear, and $HPS1^{-/-}CHI3L1^{-/-}$ double mutant mice were subjected to intratracheal bleomycin administration. FIG. 3C depicts a graph of all TUNEL-positive cells counted on Day 7. FIG. 3D depicts a graph of total lung collagen quantified using Sircol assay on Day 14. WT,CHI3L1 Tg, pale ear, and HPS1⁻/⁻CHI3L1 Tg mice were subjected to intratracheal bleomycin administration. FIG. 3E depicts a graph of CHI3L1 Tg turned on from Day 0 to Day 5. All TUNEL-positive cells were counted on Day 7. FIG. 3F depicts a graph of CHI3L1 Tg turned on from Day 5 to Day 14. Total lung collagen was quantified using Sircol assay on Day 14. Values are mean±SEM with a minimum of 4 mice in each group. *p≤0.05,**p≤0.01.

FIG. 5C depicts the results after total protein was extracted from the plasma membrane fraction and Western blot analysis was performed to detect IL-13Rα2. Pan-Cadherin was used as specificity and loading controls. FIGS. 5D and 5E depict graphs of TUNEL-positive cells. Values are mean±SEM with 3 experiments. *p≤0.05, **p≤0.01.

FIG. 6A depicts the results of CHI3L1 and CRTH2 co-immunoprecipitation. Immunoprecipitation (IP) of CHI3L1 or CRTH2 was undertaken and the precipitate was then evaluated by Western immunoblot (IB) analysis as noted. Lung lysates from wild-type (IL-13Tg (−)) and IL-13 Tg (+) mice were employed. FIG. 6B depicts graphs of FACS analysis of co-localization of CHI3L1 and CRTH2. THP-1 cells were incubated in the presence or absence of anti-CHI3L1-biotin antibody or anti-CRTH2 immunoglobulin G (IgG) antibody without permeabilization. The cells were then washed and stained with streptavidin (SA)-PE and anti-igG-APC and subjected to flow cytometric analysis. FIG. 6C depicts the results after total protein was extracted from bleomycin or saline-treated WT and pale ear mouse lungs and separated into cytoplasmic fraction or plasma membrane fractions. Western blot analysis was performed to detect CRTH2. Pan-Cadherin and GAPDH were used as specificity and loading controls. In FIGS. 6D-6E, WT, pale ear, and CHI3L1 Tg mice were subjected to intratracheal bleomycin administration. Mice were treated with CRTH2 inhibitor or its vehicle control. Total lung collagen was quantified using Sircol assay on Day 14. The noted values are the mean±SEM of evaluations of a minimum of 6 mice in each group. **p≤0.01.

DETAILED DESCRIPTION

Figure 1A:
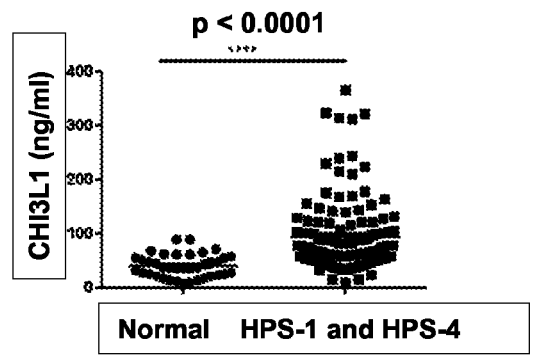
FIGS. 1A-1G demonstrate that CHI3L1 levels are increased in HPS patients.

As described herein, a subset of patients with Hermansky Pudlak Syndrome will develop pulmonary fibrosis, which is very likely to prove fatal. The inventors have discovered that aberrations in CHI3L1 signaling through IL-13Rα2 and CRTH2 are responsible for lung injury and fibrosis in subjects with HPS. As a result, CHI3L1 levels are increased in patients having pulmonary fibrosis (or likely to develop pulmonary fibrosis). Accordingly, provided herein are methods of treating and/or preventing pulmonary fibrosis in a subject with HPS and methods of diagnosing and/or prognosing pulmonary fibrosis in a subject with HPS.

As described herein, "Hermansky Pudlak Syndrome" or "HPS" refers to a group of inherited recessive disorders caused by mutations that alter the function of lysosome-related organelles and are characterized by oculocutaneous albinism and visual impairment. Nine genetic subtypes (HPS1-9) have been described with each mutation affecting the function of lysosome-related organelles (LROs). HPS patients can develop pulmonary fibrosis, which is the leading cause of death for HPS subjects. Pulmonary fibrosis is most commonly developed in subjects with genetic defects in the biogenesis of lysosome-related organelle complex 3 (BLOC-3) (e.g. HPS-1, HPS-2, and HPS-4 subjects), but there is no existing clinical method for determining which subjects in these populations will develop pulmonary fibrosis, nor are treatments that will successfully halt the progression of pulmonary fibrosis available.

In one aspect, described herein is a method of treating HPS in a subject in need thereof, the method comprising administering an agonist of IL-13Rα2 and/or an inhibitor of CRTH2 to the subject. In some embodiments, described herein is a method of treating and/or preventing pulmonary fibrosis in a subject in need of treatment for HPS, the method comprising administering an agonist of IL-13Rα2 and/or an inhibitor of CRTH2 to the subject. In some embodiments, the subject is a subject having or diagnosed as having HPS-1, HPS-2, and/or HPS-4. In some embodiments, the subject with HPS is a subject with a defect in BLOC-3. In some embodiments, the subject with HPS is a subject with HPS-1, HPS-2, and/or HPS-4. In some embodiments, an agonist of IL-13Rα2 is administered. In some embodiments, the agonist of IL-13Rα2 can be an IL-13Rα2 polypeptide or a nucleic acid encoding a IL-13Rα2 polypeptide. In some embodiments, the IL-13Rα2 polypeptide or a nucleic acid encoding a IL-13Rα2 polypeptide can be targeted to the plasma membrane, e.g. so that it can interact with a natural agonist as described herein. In some embodiments, an inhibitor of CRTH2 is administered. In some embodiments, an agonist of IL-13Rα2 and an inhibitor of CRTH2 are administered.

As used herein, "IL-13Rα2," "Interleukin-13 receptor subunit alpha-2," or "CD213A2" refers to a membrane bound protein that binds to IL-13 with very high affinity, and negatively regulates both IL-13 and IL-4. IL-13Rα2 competes with the IL-13 receptor comprising IL-13Rα1 and IL4R alpha for binding of IL-13. Sequences for IL-13Rα2 expression products are known for a number of species, e.g., human IL-13Rα2 (NCBI Gene ID: 3598) mRNA (SEQ ID NO: 1; NCBI Ref Seq: NM_000640) and polypeptide (SEQ ID NO: 2; NCBI Ref Seq: NP_000631).

As used herein, the term "agonist" refers to any agent that increases the level and/or activity of the target, e.g., of IL-13Rα2. As used herein, the term "agonist" refers to an agent which increases the expression and/or activity of the target by at least 10% or more, e.g. by 10% or more, 50% or more, 100% or more, 200% or more, 500% or more, or 1000% or more. Non-limiting examples of agonists of IL-13Rα2 can include IL-13Rα2 polypeptides or fragments thereof and nucleic acids encoding a IL-13Rα2 polypeptide, e.g. a polypeptide comprising the sequence SEQ ID NO: 2 or a nucleic acid comprising the sequence of SEQ ID NO: 1 or variants thereof.

In some embodiments, an agonist of IL-13Rα2 increases the level of an IL-13Rα2 expression product and/or increases the level of IL-13Rα2 polypeptide localized to the plasma membrane (e.g. increases the absolute level of IL-13Rα2 polypeptide localized to the plasma membrane and/or increases the proportion of IL-13Rα2 in the cell which is localized to the plasma membrane).

In some embodiments, an agonist of IL-13Rα2 can be an agonist of Rab32/38. As used herein, "Rab32/38" refers to Rab32 (member RAS oncogene family 32) and Rab38 (member RAS oncogene family 38), a pair of Rab small GTPases that both contribute to melanosome biogenesis and pigmentation enzyme transport and are located in perinuclear vesicles. Rab32 and Rab38 are able to functionally compensate, at least in part, for each other. BLOC-3 is the guanine nucleotide exchange factor (GEF) for Rab32/38. Sequences for Rab32/38 are known for a number of species, e g human Rab32 (NCBI Gene ID: 10981) mRNA (SEQ ID NO: 7; NCBI Ref Seq: NM_006834) and polypeptide (SEQ ID NO: 8; NCBI Ref Seq: NP_006825) and human Rab38 (NCBI Gene ID: 23682) mRNA (SEQ ID NO: 9; NCBI Ref Seq: NM_022337) and polypeptide (SEQ ID NO: 10; NCBI Ref Seq: NP_071732). An agonist of Rab32/38 can be an agonist of Rab32, an agonist of Rab38, or an agonist of both Rab32 and Rab38.

As used herein, "CRTH2," "chemoattractant homologous receptor expressed on Th2 cells," "CD294," or "GPR44" refers to a G protein-coupled receptor activated by prostaglandin $D_2$ and/or CHI3L1. Activation of CRTH2 by prostaglandin $D_2$ induces the chemotaxis of Th2 lymphocytes and eosinophils, even in the absence of allergen or co-stimulation. Activation of CRTH2 by CHI3L1 can induce fibroproliferation. CRTH2 activity can be measured by measuring CHI3L1-induced fibroproliferation, e.g. in HPS cells and/or subjects and/or following bleomycin injury as described herein. In some embodiments, increased CRTH2 activity can be indicated by increased levels of CHI3L1-induced fibroproliferation. In some embodiments, increased CRTH2 activity can be indicated by increased M2 macrophage differentiation. The sequences of CRTH2 expression products for a number of species are known, e.g., human CRTH2 (NCBI Gene ID: 11251) mRNA (SEQ ID NO: 3; NCBI Ref Seq: NM_004778) and polypeptide (SEQ ID NO: 4; NCBI Ref Seq: NP_004769).

As used herein, the term "inhibitor" refers to an agent which can decrease the expression and/or activity of the targeted expression product (e.g. mRNA encoding the target or a target polypeptide), e.g. by at least 10% or more, e.g. by 10% or more, 50% or more, 70% or more, 80% or more, 90% or more, 95% or more, or 98% or more. The efficacy of an inhibitor of, for example, CRTH2, e.g. its ability to decrease the level and/or activity of CRTH2 can be determined, e.g. by measuring the level of an expression product of CRTH2 and/or the activity of CRTH2. Methods for measuring the level of a given mRNA and/or polypeptide are known to one of skill in the art, e.g. RT-PCR with primers can be used to determine the level of RNA and Western blotting with an antibody (e.g. an anti-CRTH2 antibody, e.g. Cat No. ab150632; Abcam; Cambridge, Mass.) can be used to determine the level of a polypeptide. The activity of, e.g. CRTH2 can be determined using methods known in the art and described elsewhere herein. In some embodiments, the inhibitor can be an inhibitory nucleic acid; an aptamer; an antibody reagent; an antibody; or a small molecule.

Small molecule inhibitors of CRTH2 are known in the art and can include, by way of non-limiting example, OC-459; AZD-1981; Setipiprant; QAW-039; QAV-680; MK-7246; ADC-3680; BI671800; ARRY-502; RG-7581; AZD-5985; AZD-8075; AM461; AM211; AMG-853; $PGD_2$; AM432; CAY-10471; TM-30089; TM-30643; TM-30642; Ramatroban; and 00000459. Such compounds and their synthesis are described, e.g., in Pettipher and Hansel. Drug News Perspect 2008 21:317-322; Xue et al. Journal of Immunology 2009 182: 7580-6; Bain et al. Journal of Pharmacology and Experimental Therapeutics 2011 338: 290-301; Molinaro et al. J Organic Chem 2012 77:2299-2309; Wang et al. Nature 2012 92(1); Busse et al. J Allergy Clin Immunol 2013 135:339-345; Sandham et al. Bioorg & Med Chem 2013 21:6582-6591; Sidharta et al. Fundamental and Clinical Pharma 2014; Diamant et al. Clinical & Exper Allergy 2014 44:1044-1052; Krug et al. J Allergy Clin Immunol 133:414-419; Gil et al. E J Phamacol 2014 743:106-116; Gehin et al. Eur J Clin Pharmacol 20014; Wenzel et al. J Allergy Clin Immunol 2014 AB abstracts; Norman Expert Opinion Ther Patents 2011 21:1931-6; Sandhman and Page J Labelled Compounds and Radiopharmaceuticals 2014 57:175-7; Norman Expert Opin Investig Drugs 2014 23:55-66; Foti et al. Drug Metabolism and Disposition 2012 40:2239-2249; Bain et al. J Clin Pharm 2012 52:1482-1493; Uller et al. Respiratory Research 2007 8:16; U.S. Pat. Nos. 8,536,158; 4,363,912; 4,859,692; 4,273,782; 8,563,536; 8,268,878; International Patent Publications WO2013/

010880; WO2009/063202; WO/03066046; WO/03066047; WO/9950268; WO/0032180; WO/0151849; WO/0164205; WO/9603376; WO/03/097598; WO 2003/097042; WO2003/097598; WO 2003/101981; WO2003/101961; WO2004/007451; WO2005/019171; WO2005/094816; WO2006/034419; WO2005/044260; WO2006/095183; and WO2008/012511; Great Britain Patent Nos. 1,356,834; 1,407,658; 1,460,348; and Japanese Patent Publications 43-24418; 2001247570; each of which is incorporated by reference herein in its entirety.

Table 1 provides exemplary CRTH2 inhibitors, e.g. CRTH2 antagonists that are in clinical trials. In some embodiments of any of the aspects described herein, the CRTH2 inhibitor can be selected from the inhibitors listed in Table 1 or derivatives or variants thereof. In some embodiments, the CRTH2 inhibitor can be selected from the group consisting of: OC-459; AZD-1981; Setipiprant; QAW-039; QAV-680; MK-7246; ADC-3680; BI671800; Arry-502; RG-7581; AZD-5985; AM461; AM211; AMG-853; and TM-30089.

TABLE 1

| Name | Company | Clinical Trial Phase | Relevant Reference(s) PMID numbers and/or links to relevant references |
|---|---|---|---|
| OC-459 | Oxagen-Eleventa | III | PMID: 24073896 |
| AZD-1981 | AstraZeneca | II | PMID: 24073896 |
| Setipiprant | Actelion | III | 25323804 |
|  |  |  | 24964348 |
|  |  |  | 24734908, |
| QAW-039 (R=CF$_3$) | Novartis | II | 24452929 |
|  |  |  | 24021582 |
| QAV-680 (R=H) |  |  |  |
| MK-7246 | Merck | I | 25261040 |
|  |  |  | 22669291 |
|  |  |  | 22335767, |
| ADC-3680 | Pulmagen | II | 24073896 |
| BI671800 | Boehringer | II | 24332218 |
| Arry-502 | Array | II | jacionline.org/article/S0091-6749(13)01941-6/abstract |
| RG-7581 | Roche | I |  |
| AZD-5985 | AstraZeneca | I | clinicaltrials.gov/show/NCT00967356 |
| AM461 | Panmira | I | 22082220 |
| AM211 | Panmira | I | 22110163 |
|  |  |  | 21487069 |
| AMG-853 | Amgen | II | 24073896 |
|  |  |  | 23174659 |
|  |  |  | 22930276 |
| TM-30089 | Cayman |  | 22442685 |
|  |  |  | 19494281 |
|  |  |  | 17328802 |

As used herein, "OC-459" refers to a compound having the structure of Formula I.

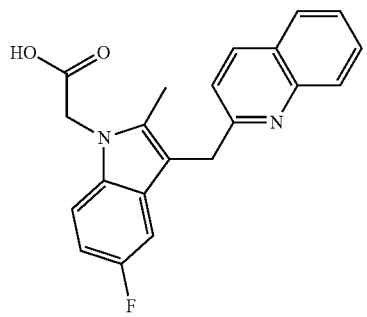

Formula I

As used herein, "AZD-1981" refers to a compound having the structure of Formula II.

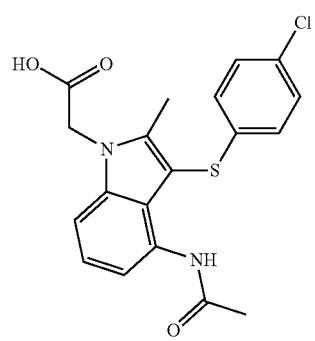

Formula II

As used herein, "setipiprant" refers to a compound having the structure of Formula III.

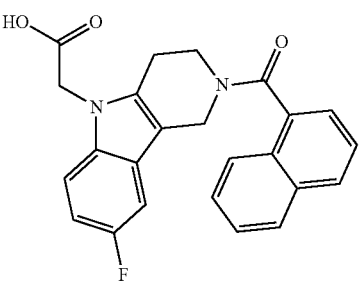

Formula III

As used herein, "QAW-039" refers to a compound having the structure of Formula IV, wherein R=CF$_3$. As used herein, "QAV-680" refers to a compound having the structure of Formula IV, wherein R=H.

Formula IV

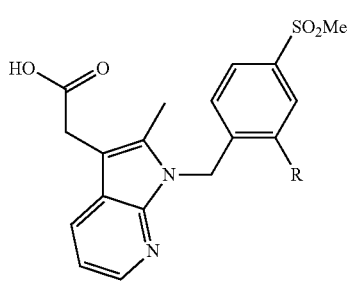

As used herein, "MK-7246" refers to a compound having the structure of Formula V.

Formula V

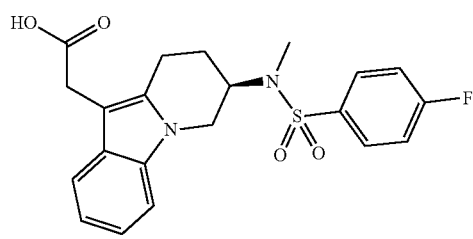

As used herein, "BI671800" refers to a compound having the structure of Formula VI.

Formula VI

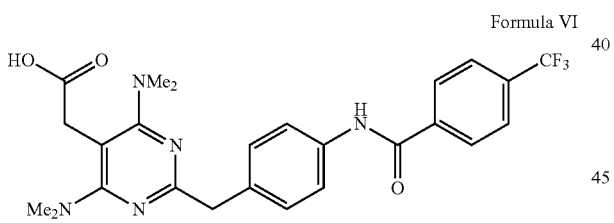

As used herein, "Any-502" refers to a compound having the structure of Formula VII.

Formula VII

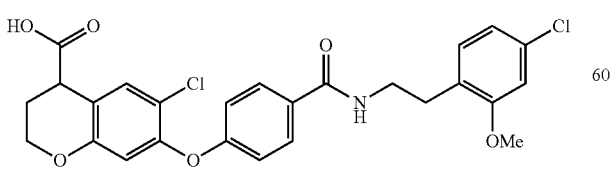

As used herein, "AZD-5985" refers to a compound having the structure of Formula VIII.

Formula VIII

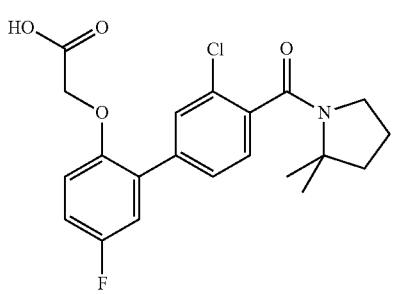

AstraZeneca
AZD-5985 or
AZD-8075

As used herein, "AM461" refers to a compound having the structure of Formula IX.

Formula IX

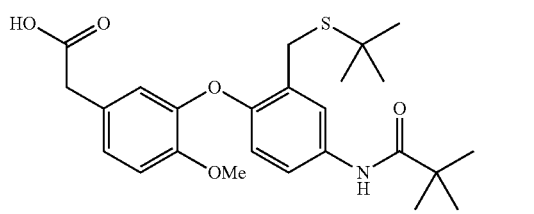

As used herein, "AM211" refers to a compound having the structure of Formula X.

Formula X

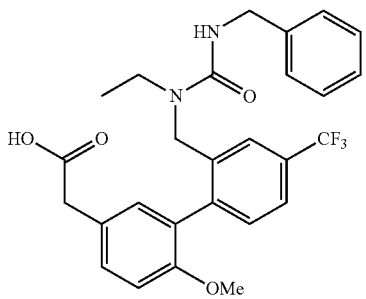

As used herein, "AMG-853" refers to a compound having the structure of Formula XI.

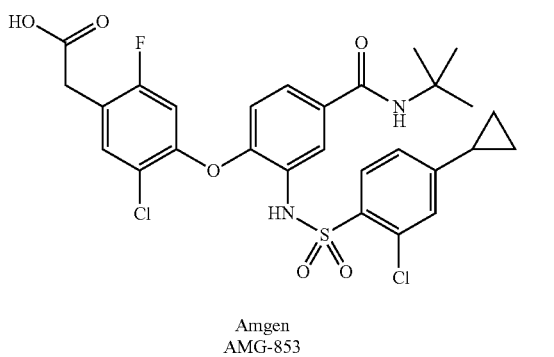

Amgen
AMG-853

As used herein, "TM-30089" refers to a compound having the structure of Formula XII.

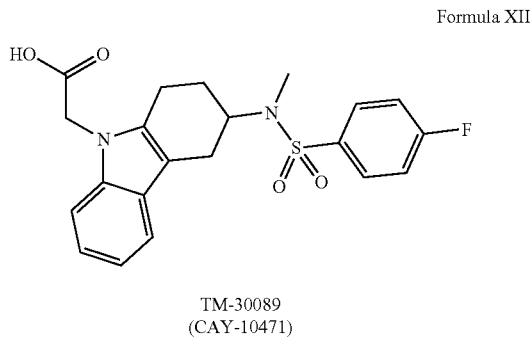 [SMILES: CN(C1CCc2c(c3ccccc3n2CC(=O)O)C1)S(=O)(=O)c1ccc(F)cc1]

TM-30089
(CAY-10471)

As described herein, increased levels of CHI3L1 expression and/or activity indicate that a subject with HPS has an increased risk of having and/or developing pulmonary fibrosis. Accordingly, in some embodiments of any of the aspects described herein, the subject that is treated in accordance with the methods described herein is a subject having or identified as having an increased level of CHI3L1 expression and/or activity.

As used herein, "CHI3L1," "chintinase-3-like protein 1," or "YKL-40" refers to a ~40 kDa glycoprotein secreted by at least macrophages, chondrocytes, neutrophils, synovial cells, and some cancer cells. CHI3L1 does not have chitinase activity, is a Th2 promoting cytokine, has been linked to the AKT anti-apoptotic signaling pathway and induces the migration of astrocytes. The sequences of CHI3L1 expression products are known for a number of species, e.g., human CHI3L1 (NCBI Gene ID No: 1116) mRNA (SEQ ID NO: 5; NCBI Ref Seq: NM_001276) and polypeptide (SEQ ID NO: 6; NCBI Ref Seq: NP_001267). The activity of CHI3L1 can be measured, e.g., by measuring the anti-apoptotic effects of CHI3L1, e.g. in response to bleomycin injury, or by measuring the level of CHI3L1-induced fibroproliferation, e.g., in response to bleomycin injury as described herein.

Increased levels of CHI3L1, as demonstrated herein, are indicative of an increased risk of likelihood of a subject with HPS developing pulmonary fibrosis. In one aspect, described herein is a method comprising measuring the level of CHI3L1 in a test sample obtained from a subject with Hermansky Pudlak Syndrome (HPS) wherein an increase in the CHI3L1 level relative to a reference level indicates the subject has a higher risk of having or developing pulmonary fibrosis. In one aspect, described herein is an assay comprising contacting a sample obtained from the subject with Hermansky Pudlak Syndrome (HPD) with a CHI3L1-specific reagent to detect the presence or level of CHI3L1; measuring/detecting the presence or intensity of a signal which indicates the presence or level of CHI3L1 in the sample; wherein an increase in the CHI3L1 level relative to a reference level indicates the subject has a higher risk of having or developing pulmonary fibrosis. In some embodiments, the methods and assays described herein include (a) transforming the CHI3L1 into a detectable target; (b) measuring the amount of the target; and (c) comparing the amount of the gene target to an amount of a reference, wherein if the amount of the detectable target is statistically significantly greater than the amount of the reference level, the subject is identified as likely to have and/or develop pulmonary fibrosis. In some embodiments, if the amount of the detectable target is not statistically significantly greater than the amount of the reference level, the subject is identified as unlikely to have and/or develop pulmonary fibrosis.

As used herein, the term "transforming" or "transformation" refers to changing an object or a substance, e.g., biological sample, nucleic acid or protein, into another substance. The transformation can be physical, biological or chemical. Exemplary physical transformation includes, but not limited to, pre-treatment of a biological sample, e.g., from whole blood to blood serum by differential centrifugation. A biological/chemical transformation can involve at least one enzyme and/or a chemical reagent in a reaction. For example, a DNA sample can be digested into fragments by one or more restriction enzyme, or an exogenous molecule can be attached to a fragmented DNA sample with a ligase. In some embodiments, a DNA sample can undergo enzymatic replication, e.g., by polymerase chain reaction (PCR).

Transformation, measurement, and/or detection of a target molecule, e.g. a CHI3L1 mRNA or polypeptide can comprise contacting a sample obtained from a subject with a reagent (e.g. a detection reagent) which is specific for the target, e.g., a CHI3L1-specific reagent. In some embodiments, the target-specific reagent is detectably labeled. In some embodiments, the target-specific reagent is capable of generating a detectable signal. In some embodiments, the target-specific reagent generates a detectable signal when the target molecule is present.

Methods to measure CHI3L1 gene expression products are well known to a skilled artisan. Such methods to measure gene expression products, e.g., protein level, include ELISA (enzyme linked immunosorbent assay), western blot, immunoprecipitation, and immunofluorescence using detection reagents such as an antibody or protein binding agents. Alternatively, a peptide can be detected in a subject by introducing into a subject a labeled anti-peptide antibody and other types of detection agent. For example, the antibody can be labeled with a detectable marker whose presence and location in the subject is detected by standard imaging techniques.

For example, antibodies for CHI3L1 are commercially available and can be used for the purposes of the invention to measure protein expression levels, e.g. anti-CHI3L1 (Cat. No. ab86428; Abcam, Cambridge Mass.). Alternatively, since the amino acid sequences for CHI3L1 are known and publically available at NCBI website, one of skill in the art can raise their own antibodies against these polypeptides of interest for the purpose of the invention.

The amino acid sequences of the polypeptides described herein, e.g. CHI3L1 have been assigned NCBI accession numbers for different species such as human, mouse and rat. In particular, the NCBI accession numbers for the amino acid sequence of human CHI3L1 is included herein, e.g. SEQ ID NO: 6.

In some embodiments, immunohistochemistry ("IHC") and immunocytochemistry ("ICC") techniques can be used. IHC is the application of immunochemistry to tissue sections, whereas ICC is the application of immunochemistry to cells or tissue imprints after they have undergone specific cytological preparations such as, for example, liquid-based preparations. Immunochemistry is a family of techniques based on the use of an antibody, wherein the antibodies are used to specifically target molecules inside or on the surface of cells. The antibody typically contains a marker that will undergo a biochemical reaction, and thereby experience a change of color, upon encountering the targeted molecules. In some instances, signal amplification can be integrated into the particular protocol, wherein a secondary antibody, that includes the marker stain or marker signal, follows the application of a primary specific antibody.

In some embodiments, the assay can be a Western blot analysis. Alternatively, proteins can be separated by two-dimensional gel electrophoresis systems. Two-dimensional gel electrophoresis is well known in the art and typically involves iso-electric focusing along a first dimension followed by SDS-PAGE electrophoresis along a second dimension. These methods also require a considerable amount of cellular material. The analysis of 2D SDS-PAGE gels can be performed by determining the intensity of protein spots on the gel, or can be performed using immune detection. In other embodiments, protein samples are analyzed by mass spectroscopy.

Immunological tests can be used with the methods and assays described herein and include, for example, competitive and non-competitive assay systems using techniques such as Western blots, radioimmunoassay (RIA), ELISA (enzyme linked immunosorbent assay), "sandwich" immunoassays, immunoprecipitation assays, immunodiffusion assays, agglutination assays, e.g. latex agglutination, complement-fixation assays, immunoradiometric assays, fluorescent immunoassays, e.g. FIA (fluorescence-linked immunoassay), chemiluminescence immunoassays (CLIA), electrochemiluminescence immunoassay (ECLIA, counting immunoassay (CIA), lateral flow tests or immunoassay (LFIA), magnetic immunoassay (MIA), and protein A immunoassays. Methods for performing such assays are known in the art, provided an appropriate antibody reagent is available. In some embodiment, the immunoassay can be a quantitative or a semi-quantitative immunoassay.

An immunoassay is a biochemical test that measures the concentration of a substance in a biological sample, typically a fluid sample such as urine, using the interaction of an antibody or antibodies to its antigen. The assay takes advantage of the highly specific binding of an antibody with its antigen. For the methods and assays described herein, specific binding of the target polypeptides with respective proteins or protein fragments, or an isolated peptide, or a fusion protein described herein occurs in the immunoassay to form a target protein/peptide complex. The complex is then detected by a variety of methods known in the art. An immunoassay also often involves the use of a detection antibody.

Enzyme-linked immunosorbent assay, also called ELISA, enzyme immunoassay or EIA, is a biochemical technique used mainly in immunology to detect the presence of an antibody or an antigen in a sample. The ELISA has been used as a diagnostic tool in medicine and plant pathology, as well as a quality control check in various industries.

In one embodiment, an ELISA involving at least one antibody with specificity for the particular desired antigen (e.g., CHI3L1 as described herein) can also be performed. A known amount of sample and/or antigen is immobilized on a solid support (usually a polystyrene micro titer plate). Immobilization can be either non-specific (e.g., by adsorption to the surface) or specific (e.g. where another antibody immobilized on the surface is used to capture antigen or a primary antibody). After the antigen is immobilized, the detection antibody is added, forming a complex with the antigen. The detection antibody can be covalently linked to an enzyme, or can itself be detected by a secondary antibody which is linked to an enzyme through bio-conjugation. Between each step the plate is typically washed with a mild detergent solution to remove any proteins or antibodies that are not specifically bound. After the final wash step the plate is developed by adding an enzymatic substrate to produce a visible signal, which indicates the quantity of antigen in the sample. Older ELISAs utilize chromogenic substrates, though newer assays employ fluorogenic substrates with much higher sensitivity.

In another embodiment, a competitive ELISA is used. Purified antibodies that are directed against a target polypeptide or fragment thereof are coated on the solid phase of multi-well plate, i.e., conjugated to a solid surface. A second batch of purified antibodies that are not conjugated on any solid support is also needed. These non-conjugated purified antibodies are labeled for detection purposes, for example, labeled with horseradish peroxidase to produce a detectable signal. A sample (e.g., a blood sample) from a subject is mixed with a known amount of desired antigen (e.g., a known volume or concentration of a sample comprising a target polypeptide) together with the horseradish peroxidase labeled antibodies and the mixture is then are added to coated wells to form competitive combination. After incubation, if the polypeptide level is high in the sample, a complex of labeled antibody reagent-antigen will form. This complex is free in solution and can be washed away. Washing the wells will remove the complex. Then the wells are incubated with TMB (3, 3',5, 5'-tetramethylbenzidene) color development substrate for localization of horseradish peroxidase-conjugated antibodies in the wells. There will be no color change or little color change if the target polypeptide level is high in the sample. If there is little or no target polypeptide present in the sample, a different complex in formed, the complex of solid support bound antibody reagents-target polypeptide. This complex is immobilized on the plate and is not washed away in the wash step. Subsequent incubation with TMB will produce much color change. Such a competitive ELSA test is specific, sensitive, reproducible and easy to operate.

There are other different forms of ELISA, which are well known to those skilled in the art. The standard techniques known in the art for ELISA are described in "Methods in Immunodiagnosis", 2nd Edition, Rose and Bigazzi, eds. John Wiley & Sons, 1980; and Oellerich, M. 1984, J. Clin. Chem. Clin. Biochem. 22:895-904. These references are hereby incorporated by reference in their entirety.

In one embodiment, the levels of a polypeptide in a sample can be detected by a lateral flow immunoassay test (LFIA), also known as the immunochromatographic assay, or strip test. LFIAs are a simple device intended to detect the presence (or absence) of antigen, e.g. a polypeptide, in a fluid sample. There are currently many LFIA tests are used for medical diagnostics either for home testing, point of care testing, or laboratory use. LFIA tests are a form of immunoassay in which the test sample flows along a solid substrate via capillary action. After the sample is applied to the test strip it encounters a colored reagent (generally comprising antibody specific for the test target antigen) bound to microparticles which mixes with the sample and transits the substrate encountering lines or zones which have been pretreated with another antibody or antigen. Depending upon the level of target polypeptides present in the sample the colored reagent can be captured and become bound at the test line or zone. LFIAs are essentially immunoassays adapted to operate along a single axis to suit the test strip format or a dipstick format. Strip tests are extremely versatile and can be easily modified by one skilled in the art for detecting an enormous range of antigens from fluid samples such as urine, blood, water, and/or homogenized tissue samples etc. Strip tests are also known as dip stick test, the name bearing from the literal action of "dipping" the test strip into a fluid sample to be tested. LFIA strip tests are easy to use, require minimum training and can easily be included as components of point-of-care test (POCT) diagnostics to be use on site in the field. LFIA tests can be operated as either competitive or sandwich assays. Sandwich LFIAs are similar to sandwich ELISA. The sample first encounters colored particles which are labeled with antibodies raised to the target antigen. The test line will also contain antibodies to the same target, although it may bind to a different epitope on the antigen. The test line will show as a colored band in positive samples. In some embodiments, the lateral flow immunoassay can be a double antibody sandwich assay, a competitive assay, a quantitative assay or variations thereof. Competitive LFIAs are similar to competitive ELISA. The sample first encounters colored particles which are labeled with the target antigen or an analogue. The test line contains antibodies to the target/its analogue. Unlabelled antigen in the sample will block the binding sites on the antibodies preventing uptake of the colored particles. The test line will show as a colored band in negative samples. There are a number of variations on lateral flow technology. It is also possible to apply multiple capture zones to create a multiplex test.

The use of "dip sticks" or LFIA test strips and other solid supports have been described in the art in the context of an immunoassay for a number of antigen biomarkers. U.S. Pat. Nos. 4,943,522; 6,485,982; 6,187,598; 5,770,460; 5,622,871; 6,565,808, U.S. patent application Ser. No. 10/278,676; U.S. Ser. No. 09/579,673 and U.S. Ser. No. 10/717,082, which are incorporated herein by reference in their entirety, are non-limiting examples of such lateral flow test devices. Examples of patents that describe the use of "dip stick" technology to detect soluble antigens via immunochemical assays include, but are not limited to U.S. Pat. Nos. 4,444,880; 4,305,924; and 4,135,884; which are incorporated by reference herein in their entireties. The apparatuses and methods of these three patents broadly describe a first component fixed to a solid surface on a "dip stick" which is exposed to a solution containing a soluble antigen that binds to the component fixed upon the "dip stick," prior to detection of the component-antigen complex upon the stick. It is within the skill of one in the art to modify the teachings of this "dip stick" technology for the detection of polypeptides using antibody reagents as described herein.

Other techniques can be used to detect the level of a polypeptide in a sample. One such technique is the dot blot, and adaptation of Western blotting (Towbin et at., Proc. Nat. Acad. Sci. 76:4350 (1979)). In a Western blot, the polypeptide or fragment thereof can be dissociated with detergents and heat, and separated on an SDS-PAGE gel before being transferred to a solid support, such as a nitrocellulose or PVDF membrane. The membrane is incubated with an antibody reagent specific for the target polypeptide or a fragment thereof. The membrane is then washed to remove unbound proteins and proteins with non-specific binding. Detectably labeled enzyme-linked secondary or detection antibodies can then be used to detect and assess the amount of polypeptide in the sample tested. The intensity of the signal from the detectable label corresponds to the amount of enzyme present, and therefore the amount of polypeptide. Levels can be quantified, for example by densitometry.

In some embodiments, the level of, e.g., CHI3L1, can be measured, by way of non-limiting example, by Western blot; immunoprecipitation; enzyme-linked immunosorbent assay (ELISA); radioimmunological assay (RIA); sandwich assay; fluorescence in situ hybridization (FISH); immunohistological staining; radioimmunometric assay; immunofluoresence assay; mass spectroscopy and/or immunoelectrophoresis assay.

In certain embodiments, the gene expression products as described herein can be instead determined by determining the level of messenger RNA (mRNA) expression of the genes described herein, e.g. CHI3L1. Such molecules can be isolated, derived, or amplified from a biological sample, such as a blood sample. Techniques for the detection of mRNA expression is known by persons skilled in the art, and can include but not limited to, PCR procedures, RT-PCR, quantitative RT-PCR Northern blot analysis, differential gene expression, RNA protection assay, microarray based analysis, next-generation sequencing; hybridization methods, etc.

In general, the PCR procedure describes a method of gene amplification which is comprised of (i) sequence-specific hybridization of primers to specific genes or sequences within a nucleic acid sample or library, (ii) subsequent amplification involving multiple rounds of annealing, elongation, and denaturation using a thermostable DNA polymerase, and (iii) screening the PCR products for a band of the correct size. The primers used are oligonucleotides of sufficient length and appropriate sequence to provide initiation of polymerization, i.e. each primer is specifically designed to be complementary to a strand of the genomic locus to be amplified. In an alternative embodiment, mRNA level of gene expression products described herein can be determined by reverse-transcription (RT) PCR and by quantitative RT-PCR (QRT-PCR) or real-time PCR methods. Methods of RT-PCR and QRT-PCR are well known in the art.

In some embodiments, the level of an mRNA can be measured by a quantitative sequencing technology, e.g. a quantitative next-generation sequence technology. Methods of sequencing a nucleic acid sequence are well known in the art. Briefly, a sample obtained from a subject can be contacted with one or more primers which specifically hybridize to a single-strand nucleic acid sequence flanking the target gene sequence and a complementary strand is synthesized. In some next-generation technologies, an adaptor (double or single-stranded) is ligated to nucleic acid molecules in the sample and synthesis proceeds from the adaptor or adaptor compatible primers. In some third-generation technologies, the sequence can be determined, e.g. by determining the location and pattern of the hybridization of probes, or measuring one or more characteristics of a single molecule as it passes through a sensor (e.g. the modulation of an electrical field as a nucleic acid molecule passes through a nanopore). Exemplary methods of sequencing include, but are not limited to, Sanger sequencing, dideoxy chain termination, high-throughput sequencing, next generation sequencing, 454 sequencing, SOLiD sequencing, polony sequencing, Illumina sequencing, Ion Torrent sequencing, sequencing by hybridization, nanopore sequencing, Helioscope sequencing, single molecule real time sequencing, RNAP sequencing, and the like. Methods and protocols for performing these sequencing methods are known in the art, see, e.g. "Next Generation Genome Sequencing" Ed. Michal Janitz, Wiley-VCH; "High-Throughput Next Generation Sequencing" Eds. Kwon and Ricke, Humanna Press, 2011; and Sambrook et al., Molecular Cloning: A Laboratory Manual (4 ed.), Cold Spring Harbor Laboratory Press, Cold Spring Harbor, N.Y., USA (2012); which are incorporated by reference herein in their entireties.

The nucleic acid sequences of the genes described herein, e.g., CHI3L1, have been assigned NCBI accession numbers for different species such as human, mouse and rat. For example, the human CHI3L1 mRNA (e.g. SEQ ID NO: 5) is known. Accordingly, a skilled artisan can design an appropriate primer based on the known sequence for determining the mRNA level of the respective gene.

Nucleic acid and ribonucleic acid (RNA) molecules can be isolated from a particular biological sample using any of a number of procedures, which are well-known in the art, the particular isolation procedure chosen being appropriate for the particular biological sample. For example, freeze-thaw and alkaline lysis procedures can be useful for obtaining nucleic acid molecules from solid materials; heat and alkaline lysis procedures can be useful for obtaining nucleic acid molecules from urine; and proteinase K extraction can be used to obtain nucleic acid from blood (Roiff, A et al. PCR: Clinical Diagnostics and Research, Springer (1994)).

In some embodiments, one or more of the reagents (e.g. an antibody reagent and/or nucleic acid probe) described herein can comprise a detectable label and/or comprise the ability to generate a detectable signal (e.g. by catalyzing reaction converting a compound to a detectable product). Detectable labels can comprise, for example, a light-absorbing dye, a fluorescent dye, or a radioactive label. Detectable labels, methods of detecting them, and methods of incorporating them into reagents (e.g. antibodies and nucleic acid probes) are well known in the art.

In some embodiments, detectable labels can include labels that can be detected by spectroscopic, photochemical, biochemical, immunochemical, electromagnetic, radiochemical, or chemical means, such as fluorescence, chemifluoresence, or chemiluminescence, or any other appropriate means. The detectable labels used in the methods described herein can be primary labels (where the label comprises a moiety that is directly detectable or that produces a directly detectable moiety) or secondary labels (where the detectable label binds to another moiety to produce a detectable signal, e.g., as is common in immunological labeling using secondary and tertiary antibodies). The detectable label can be linked by covalent or non-covalent means to the reagent. Alternatively, a detectable label can be linked such as by directly labeling a molecule that achieves binding to the reagent via a ligand-receptor binding pair arrangement or other such specific recognition molecules. Detectable labels can include, but are not limited to radioisotopes, bioluminescent compounds, chromophores, antibodies, chemiluminescent compounds, fluorescent compounds, metal chelates, and enzymes.

In other embodiments, the detection reagent is label with a fluorescent compound. When the fluorescently labeled reagent is exposed to light of the proper wavelength, its presence can then be detected due to fluorescence. In some embodiments, a detectable label can be a fluorescent dye molecule, or fluorophore including, but not limited to fluorescein, phycoerythrin, phycocyanin, o-phthaldehyde, fluorescamine, Cy3™, Cy5™, allophycocyanine, Texas Red, peridenin chlorophyll, cyanine, tandem conjugates such as phycoerythrin-Cy5™, green fluorescent protein, rhodamine, fluorescein isothiocyanate (FITC) and Oregon Green™, rhodamine and derivatives (e.g., Texas red and tetrarhodimine isothiocynate (TRITC)), biotin, phycoerythrin, AMCA, CyDyes™, 6-carboxyfhiorescein (commonly known by the abbreviations FAM and F), 6-carboxy-2',4', 7',4,7-hexachlorofiuorescein (HEX), 6-carboxy-4',5'-dichloro-2',7'-dimethoxyfiuorescein (JOE or J), N,N,N',N'-tetramethyl-6carboxyrhodamine (TAMRA or T), 6-carboxy-X-rhodamine (ROX or R), 5-carboxyrhodamine-6G (R6G5 or G5), 6-carboxyrhodamine-6G (R6G6 or G6), and rhodamine 110; cyanine dyes, e.g. Cy3, Cy5 and Cy7 dyes; coumarins, e.g. umbelliferone; benzimide dyes, e.g. Hoechst 33258; phenanthridine dyes, e.g. Texas Red; ethidium dyes; acridine dyes; carbazole dyes; phenoxazine dyes; porphyrin dyes; polymethine dyes, e.g. cyanine dyes such as Cy3, Cy5, etc; BODIPY dyes and quinoline dyes. In some embodiments, a detectable label can be a radiolabel including, but not limited to $^{3}$H, $^{125}$I, $^{35}$S, $^{32}$P, and $^{33}$P. In some embodiments, a detectable label can be an enzyme including, but not limited to horseradish peroxidase and alkaline phosphatase. An enzymatic label can produce, for example, a chemiluminescent signal, a color signal, or a fluorescent signal. Enzymes contemplated for use to detectably label an antibody reagent include, but are not limited to, malate dehydrogenase, staphylococcal nuclease, delta-V-steroid isomerase, yeast alcohol dehydrogenase, alpha-glycerophosphate dehydrogenase, triose phosphate isomerase, horseradish peroxidase, alkaline phosphatase, asparaginase, glucose oxidase, beta-galactosidase, ribonuclease, urease, catalase, glucose-VI-phosphate dehydrogenase, glucoamylase and acetylcholinesterase. In some embodiments, a detectable label is a chemiluminescent label, including, but not limited to lucigenin, luminol, luciferin, isoluminol, theromatic acridinium ester, imidazole, acridinium salt and oxalate ester. In some embodiments, a detectable label can be a spectral colorimetric label including, but not limited to colloidal gold or colored glass or plastic (e.g., polystyrene, polypropylene, and latex) beads.

In some embodiments, detection reagents can also be labeled with a detectable tag, such as c-Myc, HA, VSV-G, HSV, FLAG, V5, HIS, or biotin. Other detection systems can also be used, for example, a biotin-streptavidin system. In this system, the antibodies immunoreactive (i.e. specific for) with the biomarker of interest is biotinylated. Quantity of biotinylated antibody bound to the biomarker is determined using a streptavidin-peroxidase conjugate and a chromagenic substrate. Such streptavidin peroxidase detection kits are commercially available, e.g. from DAKO; Carpinteria, Calif. A reagent can also be detectably labeled using fluorescence emitting metals such as $^{152}$Eu, or others of the lanthanide series. These metals can be attached to the reagent using such metal chelating groups as diethylenetriaminepentaacetic acid (DTPA) or ethylenediaminetetraacetic acid (EDTA).

A level which is greater than a reference level can be a level which is greater by at least about 10%, at least about 20%, at least about 50%, at least about 100%, at least about 200%, at least about 300%, at least about 500%, at least about 1000%, or greater than the reference level. In some embodiments, a level which is greater than a reference level can be a level which is statistically significantly greater than the reference level. In some embodiments, the reference can be a level of CHI3L1 in a population of subjects who do not have or are not diagnosed as having, and/or do not exhibit signs or symptoms of pulmonary fibrosis. In some embodiments, the reference can be a level of CHI3L1 in a population of subjects with HPS who do not have or are not diagnosed as having, and/or do not exhibit signs or symptoms of pulmonary fibrosis. In some embodiments, the reference can be a level of CHI3L1 in a population of subjects who do not have or are not diagnosed as having, and/or do not exhibit signs or symptoms of HPS and who do not have or are not diagnosed as having, and/or do not exhibit signs or symptoms of pulmonary fibrosis. In some embodiments, the reference can also be a level of expression of CHI3L1 in a control sample, a pooled sample of control individuals or a numeric value or range of values based on the same. In some embodiments, the reference can be the level of CHI3L1 in a sample obtained from the same subject at an earlier point in time, e.g., the methods described herein can be used to determine if a subject's risk or likelihood of developing pulmonary fibrosis is increasing.

In some embodiments, the reference level of CHI3L1 can be a level of circulating CHI3L1 of about 75 ng/mL, e.g. as measured by the assays described in the examples herein. In some embodiments, the reference level of CHI3L1 can be a level of circulating CHI3L1 of about 100 ng/mL, e.g. as measured by the assays described in the examples herein. In some embodiments, the reference level of CHI3L1 can be a level of circulating CHI3L1 of about 125 ng/mL, e.g. as measured by the assays described in the examples herein. In some embodiments, the reference level of CHI3L1 can be a level of circulating CHI3L1 of about 150 ng/mL, e.g. as measured by the assays described in the examples herein. In some embodiments, the reference level of CHI3L1 can be a level of circulating CHI3L1 of about 200 ng/mL, e.g. as measured by the assays described in the examples herein.

In some embodiments, the level of expression products of no more than 200 other genes is determined. In some embodiments, the level of expression products of no more than 100 other genes is determined. In some embodiments, the level of expression products of no more than 20 other genes is determined. In some embodiments, the level of expression products of no more than 10 other genes is determined.

In some embodiments of the foregoing aspects, the expression level of a given gene, e.g., CHI3L1, can be normalized relative to the expression level of one or more reference genes or reference proteins.

The term "sample" or "test sample" as used herein denotes a sample taken or isolated from a biological organism, e.g., a blood or plasma sample from a subject. Exemplary biological samples include, but are not limited to, a biofluid sample; serum; plasma; urine; saliva; and/or tissue sample etc. The term also includes a mixture of the above-mentioned samples. The term "test sample" also includes untreated or pretreated (or pre-processed) biological samples. In some embodiments, a test sample can comprise cells from subject. In some embodiments, the test sample can be a blood sample. In some embodiments, the test sample can be a plasma sample.

The test sample can be obtained by removing a sample from a subject, but can also be accomplished by using previously sample (e.g. isolated at a prior timepoint and isolated by the same or another person). In addition, the test sample can be freshly collected or a previously collected sample.

In some embodiments, the test sample can be an untreated test sample. As used herein, the phrase "untreated test sample" refers to a test sample that has not had any prior sample pre-treatment except for dilution and/or suspension in a solution. Exemplary methods for treating a test sample include, but are not limited to, centrifugation, filtration, sonication, homogenization, heating, freezing and thawing, and combinations thereof. In some embodiments, the test sample can be a frozen test sample, e.g., a frozen tissue. The frozen sample can be thawed before employing methods, assays and systems described herein. After thawing, a frozen sample can be centrifuged before being subjected to methods, assays and systems described herein. In some embodiments, the test sample is a clarified test sample, for example, by centrifugation and collection of a supernatant comprising the clarified test sample. In some embodiments, a test sample can be a pre-processed test sample, for example, supernatant or filtrate resulting from a treatment selected from the group consisting of centrifugation, filtration, thawing, purification, and any combinations thereof. In some embodiments, the test sample can be treated with a chemical and/or biological reagent. Chemical and/or biological reagents can be employed to protect and/or maintain the stability of the sample, including biomolecules (e.g., nucleic acid and protein) therein, during processing. One exemplary reagent is a protease inhibitor, which is generally used to protect or maintain the stability of protein during processing. The skilled artisan is well aware of methods and processes appropriate for pre-processing of biological samples required for determination of the level of an expression product as described herein.

In some embodiments, the methods, assays, and systems described herein can further comprise a step of obtaining a test sample from a subject. In some embodiments, the subject can be a human subject. In some embodiments, the subject can be a subject in need of treatment for (e.g. having or diagnosed as having) HPS.

In one aspect, described herein is a method for selecting a treatment regimen for a subject with Hermansky Pudlak Syndrome (HPS), comprising contacting a sample obtained from the subject with Hermansky Pudlak Syndrome (HPS) with a CHI3L1-specific reagent to detect the presence or level of CHI3L1; measuring and/or detecting the presence or intensity of a signal which indicates the presence or level of CHI3L1 in the sample; selecting a treatment regimen comprising a treatment for pulmonary fibrosis when the subject has an increase in the CHI3L1 level relative to a reference level; and selecting a treatment regimen not comprising a treatment for pulmonary fibrosis when the subject does not have an increase in the CHI3L1 level relative to a reference level. In one aspect, described herein is a method of identifying a subject with Hermansky Pudlak Syndrome (HPS) in need of treatment for pulmonary fibrosis, the method comprising: measuring and/or detecting the level of CHI3L1 in a test sample obtained from a subject; and identifying the subject as being in need of treatment for pulmonary fibrosis when the expression level of CHI3L1 is increased relative to a reference level. In one aspect, described herein is a method of treatment for pulmonary fibrosis in a subject with Hermansky Pudlak Syndrome, the method comprising; measuring and/or detecting the level of CHI3L1 in a test sample obtained from a subject; treating the subject with a pulmonary fibrosis treatment when the level of CHI3L1 is increased relative to a reference level; and not treating the subject with a pulmonary fibrosis treatment when the level of CHI3L1 is not increased relative to a reference level.

Treatments for pulmonary fibrosis have been tried for years and are known in the art. Treatments that have been utilized include, by way of non-limiting example, corticosteroids (e.g., prednisone), immunosuppressants e.g., cyclophosphamide, azathioprine, methotrexate, penicillamine, cyclosporine, colchicine, IFN-gamma and mycophenolate mofetil. Recently, efficacy has been demonstrated with pirfendione and nintedanib. Supportive measures such as oxygen supplementation, and/or lung transplantation have also been utilized. In some embodiments, a treatment for pulmonary fibrosis can comprise administering an agonist of IL-13Rα2 and/or an inhibitor of CRTH2 as described herein.

In one aspect, described herein is a method of determining if a subject with Hermansky Pudlak Syndrome (HPS) is at risk for pulmonary fibrosis, the method comprising measuring and/or detecting the level of CHI3L1 in a test sample obtained from a subject; comparing the level of CHI3L1 in the sample to a reference level of CHI3L1; determining that the subject is at risk for pulmonary fibrosis when the level of CHI3L1 is increased relative to a reference level; and determining that the subject is not at risk for pulmonary fibrosis when the level of CHI3L1 is not increased relative to a reference level.

In one aspect, described herein is a method of determining the efficacy of a treatment for pulmonary fibrosis in a subject with Hermansky Pudlak Syndrome (HPS), the method comprising: (a) measuring and/or detecting the level of CHI3L1 in a test sample obtained from a subject before administration of the treatment; (b) measuring and/or detecting the level of CHI3L1 in a test sample obtained from a subject after administration of the treatment; and (c) determining that the treatment is not efficacious when the expression level determined in step (b) is increased relative to the expression level determined in step (a).

In some embodiments, the methods described herein relate to treating a subject having or diagnosed as having HPS. Subjects having HPS can be identified by a physician using current methods of diagnosing HPS. Symptoms and/or complications of HPS which characterize these conditions and aid in diagnosis are well known in the art and include but are not limited to, decreased pigmentation (oculocutaneous albinism), bleeding problems, and lysosomal accumulation of ceroid lipofuscin. Tests that may aid in a diagnosis of, e.g. HPS include, but are not limited to, tests for the presence of dense bodies on whole mount EM of platelets, and genetic testing. A family history of HPS can also aid in determining if a subject is likely to have HPS or in making a diagnosis of HPS.

The compositions and methods described herein can be administered to a subject having or diagnosed as having HPS. In some embodiments, the methods described herein comprise administering an effective amount of compositions described herein, e.g. an agonist of IL-13Rα2 and/or an inhibitor of CRTH2 to a subject in order to alleviate a symptom of HPS, e g pulmonary fibrosis. As used herein, "alleviating a symptom" is ameliorating the referenced condition or symptom associated with the condition. As compared with an equivalent untreated control, such reduction is by at least 5%, 10%, 20%, 40%, 50%, 60%, 80%, 90%, 95%, 99% or more as measured by any standard technique. A variety of means for administering the compositions described herein to subjects are known to those of skill in the art. Such methods can include, but are not limited to oral, parenteral, intravenous, intramuscular, subcutaneous, transdermal, airway (aerosol), pulmonary, cutaneous, topical, or injection administration. Administration can be local or systemic.

The term "effective amount" as used herein refers to the amount of, e.g. an agonist of IL-13Rα2 and/or an inhibitor of CRTH2 needed to alleviate at least one or more symptom of the disease or disorder, and relates to a sufficient amount of pharmacological composition to provide the desired effect. The term "therapeutically effective amount" therefore refers to an amount of, e.g., an agonist of IL-13Rα2 and/or an inhibitor of CRTH2, that is sufficient to provide a particular anti-fibrotic effect when administered to a typical subject. An effective amount as used herein, in various contexts, would also include an amount sufficient to delay the development of a symptom of the disease, alter the course of a symptom disease (for example but not limited to, slowing the progression of a symptom of the disease), or reverse a symptom of the disease. Thus, it is not generally practicable to specify an exact "effective amount". However, for any given case, an appropriate "effective amount" can be determined by one of ordinary skill in the art using only routine experimentation.

Effective amounts, toxicity, and therapeutic efficacy can be determined by standard pharmaceutical procedures in cell cultures or experimental animals, e.g., for determining the LD50 (the dose lethal to 50% of the population) and the ED50 (the dose therapeutically effective in 50% of the population). The dosage can vary depending upon the dosage form employed and the route of administration utilized. The dose ratio between toxic and therapeutic effects is the therapeutic index and can be expressed as the ratio LD50/ED50. Compositions and methods that exhibit large therapeutic indices are preferred. A therapeutically effective dose can be estimated initially from cell culture assays. Also, a dose can be formulated in animal models to achieve a circulating plasma concentration range that includes the IC50 (i.e., the concentration of the active ingredient which achieves a half-maximal inhibition of symptoms) as determined in cell culture, or in an appropriate animal model. Levels in plasma can be measured, for example, by high performance liquid chromatography. The effects of any particular dosage can be monitored by a suitable bioassay, e.g., assay for CHI3L1 levels, among others. The dosage can be determined by a physician and adjusted, as necessary, to suit observed effects of the treatment.

In some embodiments, the technology described herein relates to a pharmaceutical composition comprising, e.g., an agonist of IL-13Rα2 and/or an inhibitor of CRTH2, as described herein, and optionally a pharmaceutically acceptable carrier. Pharmaceutically acceptable carriers and diluents include saline, aqueous buffer solutions, solvents and/or dispersion media. The use of such carriers and diluents is well known in the art. Some non-limiting examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, methylcellulose, ethyl cellulose, microcrystalline cellulose and cellulose acetate; (4) powdered tragacanth; (5) malt; (6) gelatin; (7) lubricating agents, such as magnesium stearate, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol (PEG); (12) esters, such as ethyl oleate and ethyl laurate; (13) agar;

(14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) bulking agents, such as polypeptides and amino acids (23) serum component, such as serum albumin, HDL and LDL; (22) $C_2$-$C_{12}$ alcohols, such as ethanol; and (23) other non-toxic compatible substances employed in pharmaceutical formulations. Wetting agents, coloring agents, release agents, coating agents, sweetening agents, flavoring agents, perfuming agents, preservative and antioxidants can also be present in the formulation. The terms such as "excipient", "carrier", "pharmaceutically acceptable carrier" or the like are used interchangeably herein. In some embodiments, the carrier inhibits the degradation of the active agent.

In some embodiments, the pharmaceutical composition comprising, e.g., an agonist of IL-13Rα2 and/or an inhibitor of CRTH2 as described herein can be a parenteral dose form. Since administration of parenteral dosage forms typically bypasses the patient's natural defenses against contaminants, parenteral dosage forms are preferably sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, and emulsions. In addition, controlled-release parenteral dosage forms can be prepared for administration of a patient, including, but not limited to, DUROS®-type dosage forms and dose-dumping.

Suitable vehicles that can be used to provide parenteral dosage forms as disclosed within are well known to those skilled in the art. Examples include, without limitation: sterile water; water for injection USP; saline solution; glucose solution; aqueous vehicles such as but not limited to, sodium chloride injection, Ringer's injection, dextrose injection, dextrose and sodium chloride injection, and lactated Ringer's injection; water-miscible vehicles such as, but not limited to, ethyl alcohol, polyethylene glycol, and propylene glycol; and non-aqueous vehicles such as, but not limited to, corn oil, cottonseed oil, peanut oil, sesame oil, ethyl oleate, isopropyl myristate, and benzyl benzoate. Compounds that alter or modify the solubility of a pharmaceutically acceptable salt of, e.g., an agonist of IL-13Rα2 and/or an inhibitor of CRTH2, as disclosed herein can also be incorporated into the parenteral dosage forms of the disclosure, including conventional and controlled-release parenteral dosage forms.

Pharmaceutical compositions comprising, e.g., an agonist of IL-13Rα2 and/or an inhibitor of CRTH2, can also be formulated to be suitable for oral administration, for example as discrete dosage forms, such as, but not limited to, tablets (including without limitation scored or coated tablets), pills, caplets, capsules, chewable tablets, powder packets, cachets, troches, wafers, aerosol sprays, or liquids, such as but not limited to, syrups, elixirs, solutions or suspensions in an aqueous liquid, a non-aqueous liquid, an oil-in-water emulsion, or a water-in-oil emulsion. Such compositions contain a predetermined amount of the pharmaceutically acceptable salt of the disclosed compounds, and may be prepared by methods of pharmacy well known to those skilled in the art. See generally, Remington: The Science and Practice of Pharmacy, 21st Ed., Lippincott, Williams, and Wilkins, Philadelphia Pa. (2005).

A composition as described herein can be administered directly to the airways of a subject in the form of an aerosol or by nebulization. For use as aerosols, a, e.g., agonist of IL-13Rα2 and/or inhibitor of CRTH2, in solution or suspension may be packaged in a pressurized aerosol container together with suitable propellants, for example, hydrocarbon propellants like propane, butane, or isobutane with conventional adjuvants. Halocarbon propellants can include fluorocarbon propellants in which all hydrogens are replaced with fluorine, chlorofluorocarbon propellants in which all hydrogens are replaced with chlorine and at least one fluorine, hydrogen-containing fluorocarbon propellants, and hydrogen-containing chlorofluorocarbon propellants. Halocarbon propellants are described in Johnson, U.S. Pat. No. 5,376,359, issued Dec. 27, 1994; Byron et al., U.S. Pat. No. 5,190,029, issued Mar. 2, 1993; and Purewal et al., U.S. Pat. No. 5,776,434, issued Jul. 7, 1998. Hydrocarbon propellants useful in the invention include, for example, propane, isobutane, n-butane, pentane, isopentane and neopentane. A blend of hydrocarbons can also be used as a propellant. Ether propellants include, for example, dimethyl ether as well as the ethers. An aerosol formulation of the invention can also comprise more than one propellant. For example, an aerosol formulation can comprise more than one propellant from the same class, such as two or more fluorocarbons; or more than one, more than two, more than three propellants from different classes, such as a fluorohydrocarbon and a hydrocarbon. Pharmaceutical compositions of the present invention can also be dispensed with a compressed gas, e.g., an inert gas such as carbon dioxide, nitrous oxide or nitrogen.

Aerosol formulations can also include other components, for example, ethanol, isopropanol, propylene glycol, as well as surfactants or other components such as oils and detergents. These components can serve to stabilize the formulation and/or lubricate valve components. The aerosol formulation can be packaged under pressure and can be formulated as an aerosol using solutions, suspensions, emulsions, powders and semisolid preparations.

An agonist of IL-13Rα2 and/or an inhibitor of CRTH2 can also be administered in a non-pressurized form such as in a nebulizer or atomizer.

An aerosol formulation can also be a dispersion or suspension. A suspension aerosol formulation may comprise a suspension of an agent or combination of agents of the instant invention, e.g., a an agonist of IL-13Rα2 and/or an inhibitor of CRTH2, and a dispersing agent. Dispersing agents useful in the invention include, for example, sorbitan trioleate, oleyl alcohol, oleic acid, lecithin and corn oil. A suspension aerosol formulation can also include lubricants, preservatives, antioxidant, and/or other aerosol components.

An aerosol formulation can be formulated as an emulsion. An emulsion aerosol formulation can include, for example, an alcohol such as ethanol, a surfactant, water and a propellant, as well as an agent or combination of agents, e.g., an agonist of IL-13Rα2 and/or an inhibitor of CRTH2. The surfactant used can be nonionic, anionic or cationic. One example of an emulsion aerosol formulation comprises, for example, ethanol, surfactant, water and propellant. Another example of an emulsion aerosol formulation comprises, for example, vegetable oil, glyceryl monostearate and propane.

The term "nebulization" is well known in the art to include reducing liquid to a fine spray. Preferably, by such nebulization small liquid droplets of uniform size are produced from a larger body of liquid in a controlled manner. Nebulization can be achieved by any suitable means therefore, including by using many nebulizers known and marketed today. For example, an AEROMIST pneumatic nebulizer available from Inhalation Plastic, Inc. of Niles, Ill. When the active ingredients are adapted to be administered, either together or individually, via nebulizer(s) they can be in the form of a nebulized aqueous suspension or solution, with or without a suitable pH or tonicity adjustment, either as a unit dose or multidose device. As is well known, any suitable gas can be used to apply pressure during the nebulization, with preferred gases to date being those which are chemically inert to an agonist of IL-13Rα2 and/or an inhibitor of CRTH2. Exemplary gases including, but are not limited to, nitrogen, argon or helium can be used to high advantage.

In some embodiments, an agonist of IL-13Rα2 and/or an inhibitor of CRTH2 can also be administered directly to the airways in the form of a dry powder. For use as a dry powder, an agonist of IL-13Rα2 and/or an inhibitor of CRTH2 can be administered by use of an inhaler. Exemplary inhalers include metered dose inhalers and dry powdered inhalers.

A metered dose inhaler or "MDI" is a pressure resistant canister or container filled with a product such as a pharmaceutical composition dissolved in a liquefied propellant or micronized particles suspended in a liquefied propellant. The propellants which can be used include chlorofluorocarbons, hydrocarbons or hydrofluoroalkanes. Especially preferred propellants are P134a (tetrafluoroethane) and P227 (heptafluoropropane) each of which may be used alone or in combination. They are optionally used in combination with one or more other propellants and/or one or more surfactants and/or one or more other excipients, for example ethanol, a lubricant, an anti-oxidant and/or a stabilizing agent. The correct dosage of the composition is delivered to the patient.

A dry powder inhaler (i.e. TURBUHALER™ (Astra AB)) is a system operable with a source of pressurized air to produce dry powder particles of a pharmaceutical composition that is compacted into a very small volume. Dry powder aerosols for inhalation therapy are generally produced with mean diameters primarily in the range of <5 μm. As the diameter of particles exceeds 3 μm, there is increasingly less phagocytosis by macrophages. However, increasing the particle size also has been found to minimize the probability of particles (possessing standard mass density) entering the airways and acini due to excessive deposition in the oropharyngeal or nasal regions.

Suitable powder compositions include, by way of illustration, powdered preparations of an agonist of IL-13Rα2 and/or an inhibitor of CRTH2 thoroughly intermixed with lactose, or other inert powders acceptable for intrabronchial administration. The powder compositions can be administered via an aerosol dispenser or encased in a breakable capsule which may be inserted by the patient into a device that punctures the capsule and blows the powder out in a steady stream suitable for inhalation. The compositions can include propellants, surfactants, and co-solvents and may be filled into conventional aerosol containers that are closed by a suitable metering valve.

Aerosols for the delivery to the respiratory tract are known in the art. See for example, Adjei, A. and Garren, J. Pharm. Res., 1: 565-569 (1990); Zanen, P. and Lamm, J.-W. J. Int. J. Pharm., 114: 111-115 (1995); Gonda, I. "Aerosols for delivery of therapeutic an diagnostic agents to the respiratory tract," in Critical Reviews in Therapeutic Drug Carrier Systems, 6:273-313 (1990); Anderson et al., Am. Rev. Respir. Dis., 140: 1317-1324 (1989)) and have potential for the systemic delivery of peptides and proteins as well (Patton and Platz, Advanced Drug Delivery Reviews, 8:179-196 (1992)); Timsina et. al., Int. J. Pharm., 101: 1-13 (1995); and Tansey, I. P., Spray Technol. Market, 4:26-29 (1994); French, D. L., Edwards, D. A. and Niven, R. W., Aerosol Sci., 27: 769-783 (1996); Visser, J., Powder Technology 58:

1-10 (1989)); Rudt, S. and R. H. Muller, J. Controlled Release, 22: 263-272 (1992); Tabata, Y, and Y. Ikada, Biomed. Mater. Res., 22: 837-858 (1988); Wall, D. A., Drug Delivery, 2: 10 1-20 1995); Patton, J. and Platz, R., Adv. Drug Del. Rev., 8: 179-196 (1992); Bryon, P., Adv. Drug. Del. Rev., 5: 107-132 (1990); Patton, J. S., et al., Controlled Release, 28: 15 79-85 (1994); Damms, B. and Bains, W., Nature Biotechnology (1996); Niven, R. W., et al., Pharm. Res., 12(9); 1343-1349 (1995); and Kobayashi, S., et al., Pharm. Res., 13(1): 80-83 (1996), contents of all of which are herein incorporated by reference in their entirety.

Conventional dosage forms generally provide rapid or immediate drug release from the formulation. Depending on the pharmacology and pharmacokinetics of the drug, use of conventional dosage forms can lead to wide fluctuations in the concentrations of the drug in a patient's blood and other tissues. These fluctuations can impact a number of parameters, such as dose frequency, onset of action, duration of efficacy, maintenance of therapeutic blood levels, toxicity, side effects, and the like. Advantageously, controlled-release formulations can be used to control a drug's onset of action, duration of action, plasma levels within the therapeutic window, and peak blood levels. In particular, controlled- or extended-release dosage forms or formulations can be used to ensure that the maximum effectiveness of a drug is achieved while minimizing potential adverse effects and safety concerns, which can occur both from under-dosing a drug (i.e., going below the minimum therapeutic levels) as well as exceeding the toxicity level for the drug. In some embodiments, the an agonist of IL-13Rα2 and/or an inhibitor of CRTH2 can be administered in a sustained release formulation.

Controlled-release pharmaceutical products have a common goal of improving drug therapy over that achieved by their non-controlled release counterparts. Ideally, the use of an optimally designed controlled-release preparation in medical treatment is characterized by a minimum of drug substance being employed to cure or control the condition in a minimum amount of time. Advantages of controlled-release formulations include: 1) extended activity of the drug; 2) reduced dosage frequency; 3) increased patient compliance; 4) usage of less total drug; 5) reduction in local or systemic side effects; 6) minimization of drug accumulation; 7) reduction in blood level fluctuations; 8) improvement in efficacy of treatment; 9) reduction of potentiation or loss of drug activity; and 10) improvement in speed of control of diseases or conditions. Kim, Cherng-ju, Controlled Release Dosage Form Design, 2 (Technomic Publishing, Lancaster, Pa.: 2000).

Most controlled-release formulations are designed to initially release an amount of drug (active ingredient) that promptly produces the desired therapeutic effect, and gradually and continually release other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, ionic strength, osmotic pressure, temperature, enzymes, water, and other physiological conditions or compounds.

A variety of known controlled- or extended-release dosage forms, formulations, and devices can be adapted for use with the salts and compositions of the disclosure. Examples include, but are not limited to, those described in U.S. Pat. Nos.: 3,845,770; 3,916,899; 3,536,809; 3,598,123; 4,008, 719; 5674,533; 5,059,595; 5,591,767; 5,120,548; 5,073,543; 5,639,476; 5,354,556; 5,733,566; and 6,365,185 B1; each of which is incorporated herein by reference. These dosage forms can be used to provide slow or controlled-release of one or more active ingredients using, for example, hydroxypropylmethyl cellulose, other polymer matrices, gels, permeable membranes, osmotic systems (such as OROS® (Alza Corporation, Mountain View, Calif. USA)), or a combination thereof to provide the desired release profile in varying proportions.

The methods described herein can further comprise administering a second agent and/or treatment to the subject, e.g. as part of a combinatorial therapy. Various treatments for pulmonary fibrosis are described elsewhere herein. Subjects with HPS can be treated for one or more of the symptoms of HPS other than pulmonary fibrosis. Non-limiting examples of such treatments can include vitamin E or dDAVP (an antidiuretic) for treatment of hemorrhages, and/or ocular surgeries.

In certain embodiments, an effective dose of a composition comprising an agonist of IL-13Rα2 and/or an inhibitor of CRTH2 as described herein can be administered to a patient once. In certain embodiments, an effective dose of a composition comprising an agonist of IL-13Rα2 and/or an inhibitor of CRTH2 can be administered to a patient repeatedly. For systemic administration, subjects can be administered a therapeutic amount of a composition comprising an agonist of IL-13Rα2 and/or an inhibitor of CRTH2, such as, e.g. 0.1 mg/kg, 0.5 mg/kg, 1.0 mg/kg, 2.0 mg/kg, 2.5 mg/kg, 5 mg/kg, 10 mg/kg, 15 mg/kg, 20 mg/kg, 25 mg/kg, 30 mg/kg, 40 mg/kg, 50 mg/kg, or more.

In some embodiments, after an initial treatment regimen, the treatments can be administered on a less frequent basis. For example, after treatment biweekly for three months, treatment can be repeated once per month, for six months or a year or longer. Treatment according to the methods described herein can reduce levels of a marker or symptom of a condition, e.g. CHI3L1 levels by at least 10%, at least 15%, at least 20%, at least 25%, at least 30%, at least 40%, at least 50%, at least 60%, at least 70%, at least 80% or at least 90% or more.

The dosage of a composition as described herein can be determined by a physician and adjusted, as necessary, to suit observed effects of the treatment. With respect to duration and frequency of treatment, it is typical for skilled clinicians to monitor subjects in order to determine when the treatment is providing therapeutic benefit, and to determine whether to increase or decrease dosage, increase or decrease administration frequency, discontinue treatment, resume treatment, or make other alterations to the treatment regimen. The dosing schedule can vary from once a week to daily depending on a number of clinical factors, such as the subject's sensitivity to, e.g., an agonist of IL-13Raα2 and/or an inhibitor of CRTH2. The desired dose or amount of activation can be administered at one time or divided into subdoses, e.g., 2-4 subdoses and administered over a period of time, e.g., at appropriate intervals through the day or other appropriate schedule. In some embodiments, administration can be chronic, e.g., one or more doses and/or treatments daily over a period of weeks or months. Examples of dosing and/or treatment schedules are administration daily, twice daily, three times daily or four or more times daily over a period of 1 week, 2 weeks, 3 weeks, 4 weeks, 1 month, 2 months, 3 months, 4 months, 5 months, or 6 months, or more. A composition comprising, e.g., an agonist of IL-13Rα2 and/or an inhibitor of CRTH2, can be administered over a period of time, such as over a 5 minute, 10 minute, 15 minute, 20 minute, or 25 minute period.

The dosage ranges for the administration of, e.g., an agonist of IL-13Rα2 and/or an inhibitor of CRTH2, according to the methods described herein depend upon, for example, the form of the active ingredient, its potency, and the extent to which symptoms, markers, or indicators of a condition described herein are desired to be reduced, for example the percentage reduction desired for, e.g., fibrosis and/or CHI3L1 levels or the extent to which, for example, IL-13Rα2 levels are desired to be induced. The dosage should not be so large as to cause adverse side effects. Generally, the dosage will vary with the age, condition, and sex of the patient and can be determined by one of skill in the art. The dosage can also be adjusted by the individual physician in the event of any complication.

The efficacy of an agonist of IL-13Rα2 and/or an inhibitor of CRTH2 in, e.g. the treatment of a condition described herein, or to induce a response as described herein (e.g. a decrease in CHI3L1 levels) can be determined by the skilled clinician. However, a treatment is considered "effective treatment," as the term is used herein, if one or more of the signs or symptoms of a condition described herein are altered in a beneficial manner, other clinically accepted symptoms are improved, or even ameliorated, or a desired response is induced e.g., by at least 10% following treatment according to the methods described herein. Efficacy can be assessed, for example, by measuring a marker, indicator, symptom, and/or the incidence of a condition treated according to the methods described herein or any other measurable parameter appropriate, e.g. CHI3L1 levels. Efficacy can also be measured by a failure of an individual to worsen as assessed by hospitalization, or need for medical interventions (i.e., progression of the disease is halted). Methods of measuring these indicators are known to those of skill in the art and/or are described herein. Treatment includes any treatment of a disease in an individual or an animal (some non-limiting examples include a human or an animal) and includes: (1) inhibiting the disease, e.g., preventing a worsening of symptoms (e.g. pain or inflammation); or (2) relieving the severity of the disease, e.g., causing regression of symptoms. An effective amount for the treatment of a disease means that amount which, when administered to a subject in need thereof, is sufficient to result in effective treatment as that term is defined herein, for that disease. Efficacy of an agent can be determined by assessing physical indicators of a condition or desired response, (e.g. the level of fibrosis). It is well within the ability of one skilled in the art to monitor efficacy of administration and/or treatment by measuring any one of such parameters, or any combination of parameters. Efficacy can be assessed in animal models of a condition described herein, for example treatment of pulmonary fibrosis in a mouse. When using an experimental animal model, efficacy of treatment is evidenced when a statistically significant change in a marker is observed, e.g. the level of fibrosis and/or the level of CHI3L1.

In vitro and animal model assays are provided herein which allow the assessment of a given dose of a treatment described herein. By way of non-limiting example, the effects of a dose of, e.g. an agonist of IL-13Rα2 and/or an inhibitor of CRTH2 can be assessed by the ability of the agonist of IL-13Rα2 and/or an inhibitor of CRTH2 to rescue the antiapoptotic effect of CHI3L1 in a cell from an HPS subject (or, e.g. an animal model thereof, e.g. pale ear mice). A non-limiting example of a protocol for such an assay can comprise transfecting alveolar type II cells from a pale ear mouse with a construct that expresses IL-13Rα2 and then treating the cells with CHI3L1 (e.g. rCHI3L1) and bleomycin and measuring the level of apoptosis.

The efficacy of a given dosage combination can also be assessed in an animal model, e.g. the pale ear mouse described herein. For example, a pale ear mouse can be treated with an agonist of IL-13Rα2 and/or an inhibitor of CRTH2 and one or more symptoms of pulmonary fibrosis measured, e.g., the level of CHI3L1, or the level of apoptosis or collagen accumulation in the lungs following administration of bleomycin.

In one aspect, described herein is a kit for performing any of the assays and/or methods described herein. In some embodiments, the kit can comprise a CHI3L1-specific reagent.

A kit is any manufacture (e.g., a package or container) comprising at least one reagent, e.g., an antibody reagent(s) or nucleic acid probe, for specifically detecting, e.g., a CHI3L1 expression product or fragment thereof, the manufacture being promoted, distributed, or sold as a unit for performing the methods or assays described herein. When the kits, and methods described herein are used for diagnosis and/or treatment of pulmonary fibrosis in patients with HPS, the reagents (e.g., detection probes) or systems can be selected such that a positive result is obtained in at least about 20%, at least about 40%, at least about 60%, at least about 80%, at least about 90%, at least about 95%, at least about 99% or in 100% of subjects having or developing pulmonary fibrosis.

In some embodiments, described herein is a kit for the detection of a CHI3L1 expression product in a sample, the kit comprising at least a first CHI3L1-specific reagent as described herein which specifically binds the CHI3L1 expression product, on a solid support and comprising a detectable label. The kits described herein include reagents and/or components that permit assaying the level of an expression product in a sample obtained from a subject (e.g., a biological sample obtained from a subject). The kits described herein can optionally comprise additional components useful for performing the methods and assays described herein.

A kit can further comprise devices and/or reagents for concentrating an expression product (e.g., a polypeptide) in a sample, e.g. a plasma sample. Thus, ultrafiltration devices permitting, e.g., protein concentration from plasma can also be included as a kit component.

Preferably, a diagnostic or prognostic kit for use with the methods and assays disclosed herein contains detection reagents for CHI3L1 expression products. Such detection reagents comprise in addition to CHI3L1-specific reagents, for example, buffer solutions, labels or washing liquids etc. Furthermore, the kit can comprise an amount of a known nucleic acid and/or polypeptide, which can be used for a calibration of the kit or as an internal control. A diagnostic kit for the detection of an expression product can also comprise accessory ingredients like secondary affinity ligands, e.g., secondary antibodies, detection dyes and any other suitable compound or liquid necessary for the performance of a expression product detection method known to the person skilled in the art. Such ingredients are known to the person skilled in the art and may vary depending on the detection method carried out. Additionally, the kit may comprise an instruction leaflet and/or may provide information as to the relevance of the obtained results.

In some aspects, the invention described herein is directed to systems (and computer readable media for causing computer systems) for obtaining data from at least one sample obtained from at least one subject, the system comprising 1) a measuring module configured to receive the at least one sample and perform at least one analysis on the at least one sample to determine the level and/or activity of CHI3L1 in the sample; 2) a storage device configured to store data output from the determination module; and 3) a display module for displaying a content based in part on the data output from the determination module, wherein the content comprises a signal indicative of the level and/or activity of CHI3L1.

Figure 7:
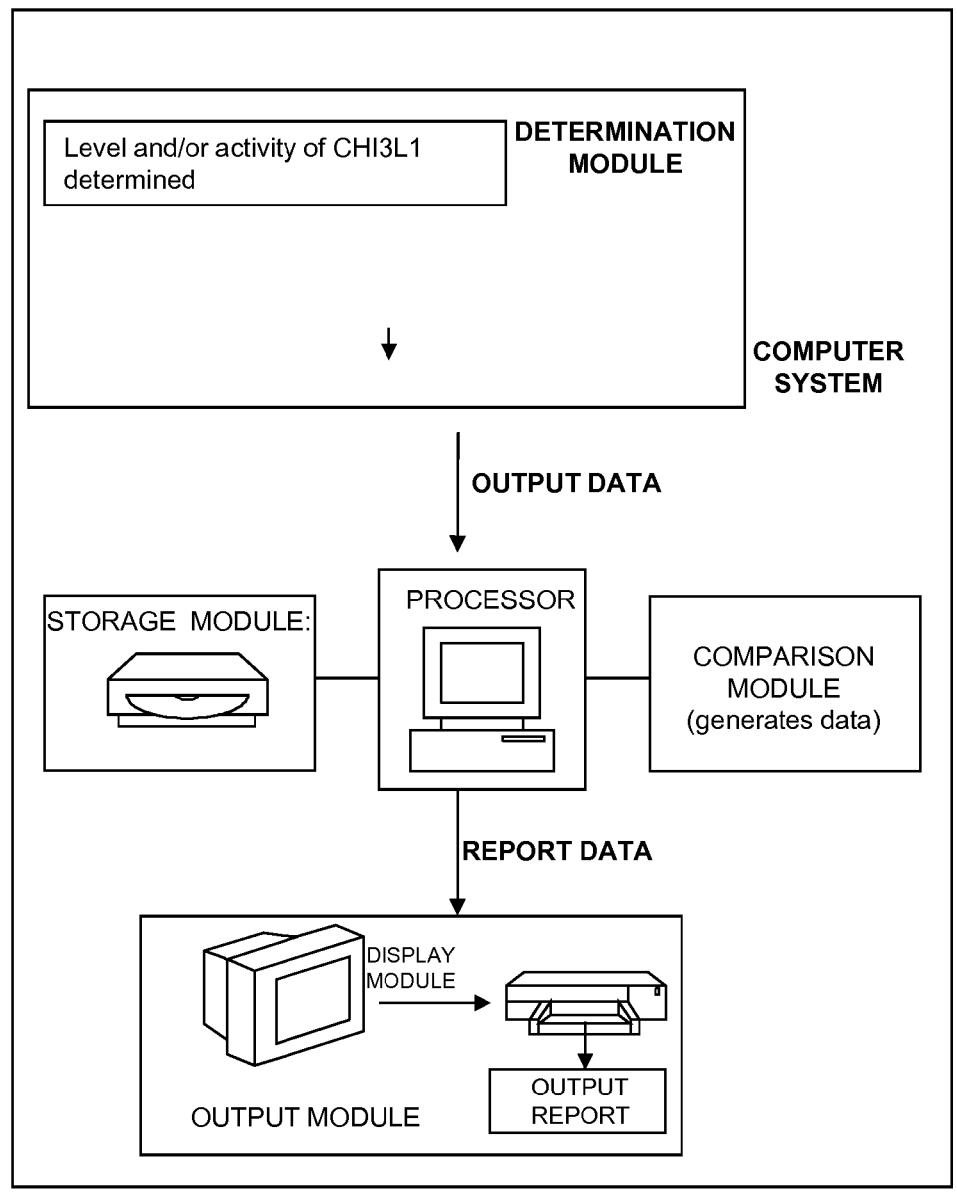
FIG. 7 is a diagram of an exemplary embodiment of a system for performing an assay for determining the level of CHI3L1 in a sample obtained from a subject.

In one embodiment, provided herein is a system comprising: (a) at least one memory containing at least one computer program adapted to control the operation of the computer system to implement a method that includes a measuring module configured to measure the level of CHI3L1 in a test sample obtained from a subject; a storage module configured to store output data from the determination module; a comparison module adapted to compare the data stored on the storage module with a reference level, and to provide a retrieved content, and a display module for displaying whether the sample comprises a level of CHI3L1 which is significantly increased relative to the reference expression level and/or displaying the relative level of CHI3L and (b) at least one processor for executing the computer program (see FIG. 7).

The term "computer" can refer to any non-human apparatus that is capable of accepting a structured input, processing the structured input according to prescribed rules, and producing results of the processing as output. Examples of a computer include: a computer; a general purpose computer; a supercomputer; a mainframe; a super mini-computer; a mini-computer; a workstation; a micro-computer; a server; an interactive television; a hybrid combination of a computer and an interactive television; a tablet; and application-specific hardware to emulate a computer and/or software. A computer can have a single processor or multiple processors, which can operate in parallel and/or not in parallel. A computer also refers to two or more computers connected together via a network for transmitting or receiving information between the computers. An example of such a computer includes a distributed computer system for processing information via computers linked by a network.

The term "computer-readable medium" may refer to any storage device used for storing data accessible by a computer, as well as any other means for providing access to data by a computer. Examples of a storage-device-type computer-readable medium include: a magnetic hard disk; a floppy disk; an optical disk, such as a CD-ROM and a DVD; a magnetic tape; a memory chip. The term a "computer system" may refer to a system having a computer, where the computer comprises a computer-readable medium embodying software to operate the computer. The term "software" is used interchangeably herein with "program" and refers to prescribed rules to operate a computer. Examples of software include: software; code segments; instructions; computer programs; and programmed logic.

The computer readable storage media can be any available tangible media that can be accessed by a computer. Computer readable storage media includes volatile and nonvolatile, removable and non-removable tangible media implemented in any method or technology for storage of information such as computer readable instructions, data structures, program modules or other data. Computer readable storage media includes, but is not limited to, RAM (random access memory), ROM (read only memory), EPROM (erasable programmable read only memory), EEPROM (electrically erasable programmable read only memory), flash memory or other memory technology, CD- ROM (compact disc read only memory), DVDs (digital versatile disks) or other optical storage media, magnetic cassettes, magnetic tape, magnetic disk storage or other magnetic storage media, other types of volatile and non-volatile memory, and any other tangible medium which can be used to store the desired information and which can accessed by a computer including and any suitable combination of the foregoing.

Computer-readable data embodied on one or more computer-readable media may define instructions, for example, as part of one or more programs that, as a result of being executed by a computer, instruct the computer to perform one or more of the functions described herein, and/or various embodiments, variations and combinations thereof. Such instructions may be written in any of a plurality of programming languages, for example, Java, J#, Visual Basic, C, C#, C++, Fortran, Pascal, Eiffel, Basic, COBOL assembly language, and the like, or any of a variety of combinations thereof. The computer-readable media on which such instructions are embodied may reside on one or more of the components of either of a system, or a computer readable storage medium described herein, may be distributed across one or more of such components.

The computer-readable media may be transportable such that the instructions stored thereon can be loaded onto any computer resource to implement the aspects of the present invention discussed herein. In addition, it should be appreciated that the instructions stored on the computer-readable medium, described above, are not limited to instructions embodied as part of an application program running on a host computer. Rather, the instructions may be embodied as any type of computer code (e.g., software or microcode) that can be employed to program a computer to implement aspects of the present invention. The computer executable instructions may be written in a suitable computer language or combination of several languages. Basic computational biology methods are known to those of ordinary skill in the art and are described in, for example, Setubal and Meidanis et al., Introduction to Computational Biology Methods (PWS Publishing Company, Boston, 1997); Salzberg, Searles, Kasif, (Ed.), Computational Methods in Molecular Biology, (Elsevier, Amsterdam, 1998); Rashidi and Buehler, Bioinformatics Basics: Application in Biological Science and Medicine (CRC Press, London, 2000) and Ouelette and Bzevanis Bioinformatics: A Practical Guide for Analysis of Gene and Proteins (Wiley & Sons, Inc., 2nd ed., 2001).

Embodiments of the invention can be described through functional modules, which are defined by computer executable instructions recorded on computer readable media and which cause a computer to perform method steps when executed. The modules are segregated by function for the sake of clarity. However, it should be understood that the modules/systems need not correspond to discreet blocks of code and the described functions can be carried out by the execution of various code portions stored on various media and executed at various times. Furthermore, it should be appreciated that the modules can perform other functions, thus the modules are not limited to having any particular functions or set of functions.

The functional modules of certain embodiments of the invention include at minimum a measuring module, a storage module, a computing module, and a display module. The functional modules can be executed on one, or multiple, computers, or by using one, or multiple, computer networks. The measuring module has computer executable instructions to provide e.g., levels of expression products etc in computer readable form.

The measuring module can comprise any system for detecting a signal elicited from an assay to determine the level and/or activity of CHI3L1 as described above herein. In some embodiments, such systems can include an instrument, e.g., AU2700 (Beckman Coulter Brea, Calif.) as described herein for quantitative measurement of polypeptides or e.g., a real time PCR machine, e.g. a LIGHTCYCLER™ (Roche). In some embodiments, the measuring module can measure the intensity of a detectable signal from an assay indicating the level of CHI3L1 polypeptide in the test sample. In some embodiments, the assay can be an immunoassay. In some embodiments, the measuring module can measure the intensity of a detectable signal from a RT-PCR assay indicating the level of CHI3L1 RNA transcript in the test sample.

The information determined in the determination system can be read by the storage module. As used herein the "storage module" is intended to include any suitable computing or processing apparatus or other device configured or adapted for storing data or information. Examples of electronic apparatus suitable for use with the present invention include stand-alone computing apparatus, data telecommunications networks, including local area networks (LAN), wide area networks (WAN), Internet, Intranet, and Extranet, and local and distributed computer processing systems. Storage modules also include, but are not limited to: magnetic storage media, such as floppy discs, hard disc storage media, magnetic tape, optical storage media such as CD-ROM, DVD, electronic storage media such as RAM, ROM, EPROM, EEPROM and the like, general hard disks and hybrids of these categories such as magnetic/optical storage media. The storage module is adapted or configured for having recorded thereon, for example, sample name, biomolecule assayed and the level of said biomolecule. Such information may be provided in digital form that can be transmitted and read electronically, e.g., via the Internet, on diskette, via USB (universal serial bus) or via any other suitable mode of communication.

As used herein, "stored" refers to a process for encoding information on the storage module. Those skilled in the art can readily adopt any of the presently known methods for recording information on known media to generate manufactures comprising expression level information.

In some embodiments of any of the systems described herein, the storage module stores the output data from the determination module. In additional embodiments, the storage module stores reference information such as levels of CHI3L1 in healthy subjects and/or a population of healthy subjects.

Figure 8:
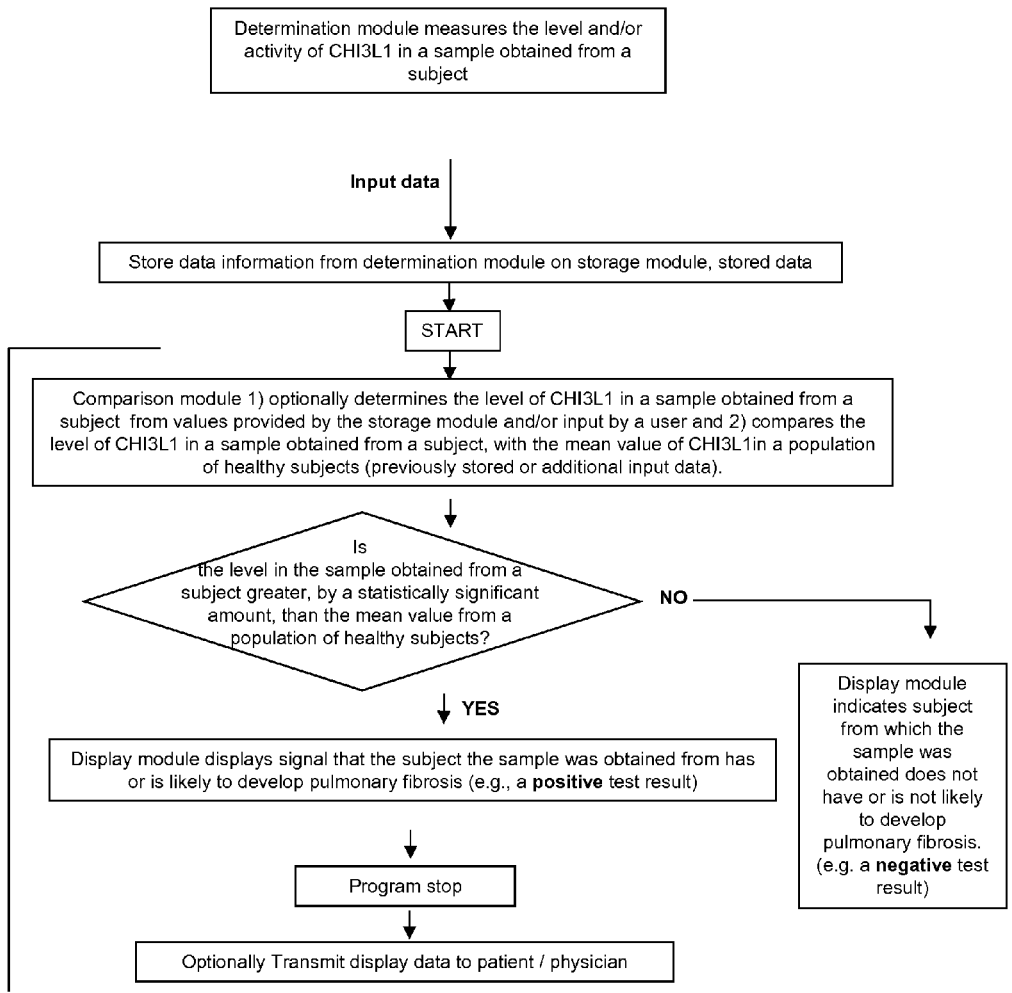
FIG. 8 is a diagram of an exemplary embodiment of a comparison module as described herein.

The "computing module" can use a variety of available software programs and formats for computing the level of CHI3L1. Such algorithms are well established in the art. A skilled artisan is readily able to determine the appropriate algorithms based on the size and quality of the sample and type of data. The data analysis tools and equations described herein can be implemented in the computing module of the invention. In one embodiment, the computing module further comprises a comparison module, which compares the level of CHI3L1 in a sample obtained from a subject as described herein with the mean value of CHI3L1 in a population of healthy subjects and/or a population of HPS patients unlikely to develop pulmonary fibrosis (FIG. 8). By way of an example, when the value of CHI3L1 in a sample obtained from a subject is measured, a comparison module can compare or match the output data with the mean value of CHI3L1 in a population of healthy subjects. In certain embodiments, the mean value of CHI3L1 in a population of healthy subjects can be pre-stored in the storage module. In various embodiments, the comparison module can be configured using existing commercially-available or freely-available software for comparison purpose, and may be optimized for particular data comparisons that are conducted.

Figure 9:
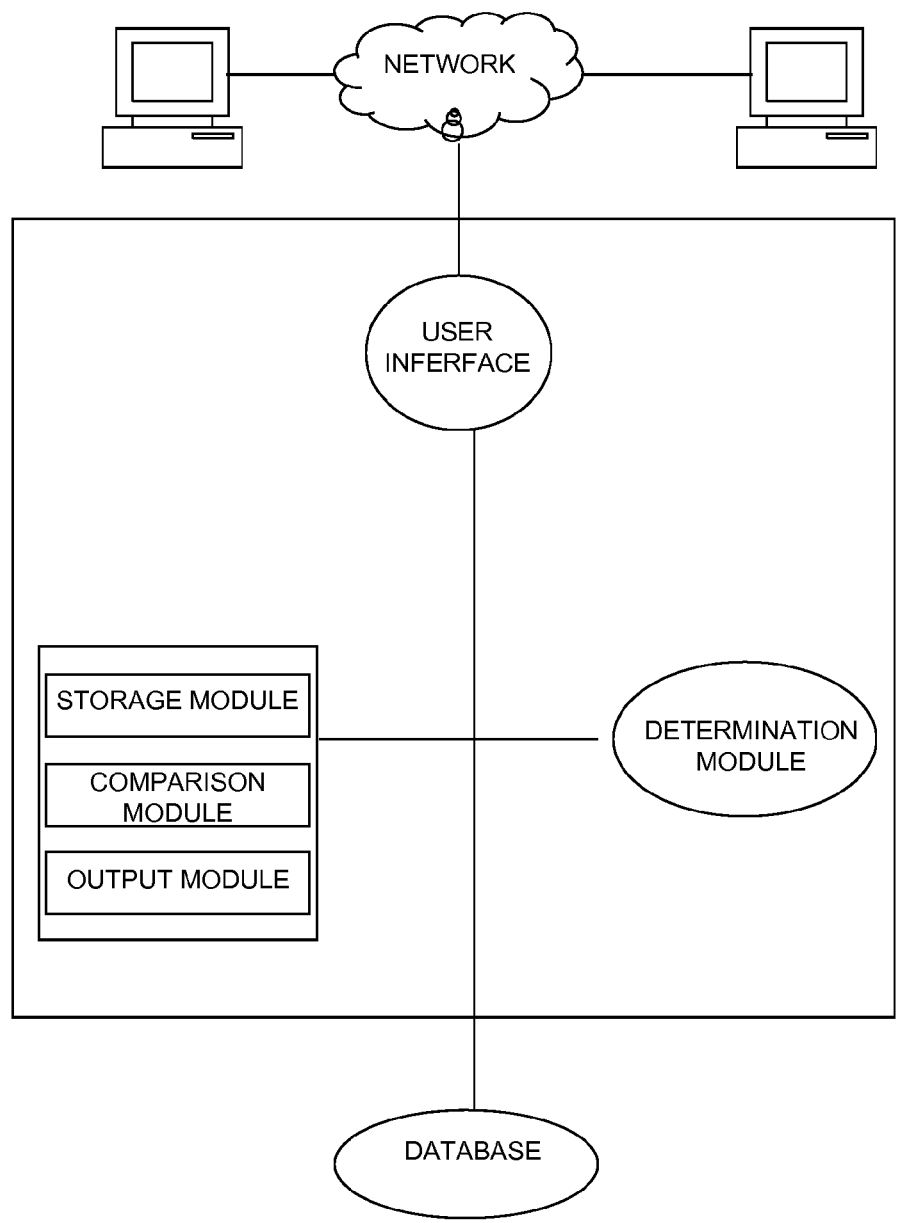
FIG. 9 is a diagram of an exemplary embodiment of an operating system and applications for a computing system as described herein.
Figure 10:
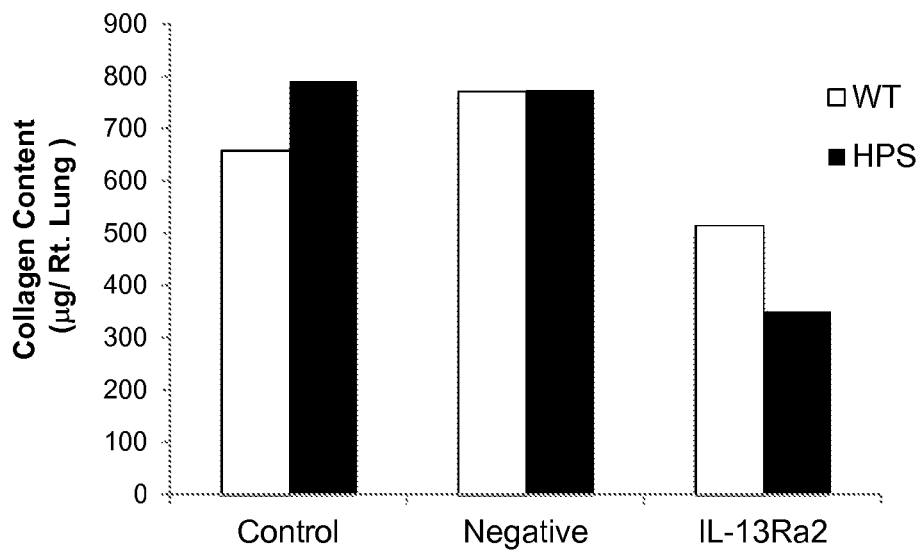
FIG. 10 depicts a graph of the effects of Lentivirus IL-13Rα2 on bleomycin-induced pulmonary fibrosis in wild type and HPS-1 null mice. Wild type (WT) and HPS-1 null mice were treated with bleomycin. Some mice received Lentivirus without an insert (negative). Others received Lentivirus expressing IL-13Receptor alpha2 (IL-13Rα2) as noted. Collagen content was assessed 14 days after bleomycin administration. For each bar N=2 that were within 10% of each other.

The computing and/or comparison module, or any other module of the invention, can include an operating system (e.g., UNIX) on which runs a relational database management system, a World Wide Web application, and a World Wide Web server. World Wide Web application includes the executable code necessary for generation of database language statements (e.g., Structured Query Language (SQL) statements). Generally, the executables will include embedded SQL statements. In addition, the World Wide Web application may include a configuration file which contains pointers and addresses to the various software entities that comprise the server as well as the various external and internal databases which must be accessed to service user requests. The Configuration file also directs requests for server resources to the appropriate hardware—as may be necessary should the server be distributed over two or more separate computers. In one embodiment, the World Wide Web server supports a TCP/IP protocol. Local networks such as this are sometimes referred to as "Intranets." An advantage of such Intranets is that they allow easy communication with public domain databases residing on the World Wide Web (e.g., the GenBank or Swiss Pro World Wide Web site). In some embodiments users can directly access data (via Hypertext links for example) residing on Internet databases using a HTML interface provided by Web browsers and Web servers (FIG. 9).

The computing and/or comparison module provides a computer readable comparison result that can be processed in computer readable form by predefined criteria, or criteria defined by a user, to provide content based in part on the comparison result that may be stored and output as requested by a user using an output module, e.g., a display module.

In some embodiments, the content displayed on the display module can be the level of CHI3L1 in the sample obtained from a subject. In some embodiments, the content displayed on the display module can be the relative level of CHI3L1 in the sample obtained from a subject as compared to the mean level of CHI3L1 in a population of healthy subjects. In some embodiments, if the computing module determines that the level of CHI3L1 in the test sample obtained from a subject is greater by a statistically significant amount than the reference level, the display module displays a signal indicating that the levels in the sample obtained from a subject are greater than those of the reference level. In some embodiments, the signal indicates the subject is in need of treatment for pulmonary fibrosis. In some embodiments, the signal indicates the degree to which the level of CHI3L1 in the sample obtained from a subject varies from the reference level. In some embodiments, the content displayed on the display module can indicate whether the subject has an increased likelihood of having or developing pulmonary fibrosis. In some embodiments, the content displayed on the display module can be a numerical value indicating one of these risks or probabilities. In such embodiments, the probability can be expressed in percentages or a fraction. For example, higher percentage or a fraction closer to 1 indicates a higher likelihood of a subject having or developing pulmonary fibrosis. In some embodiments, the content displayed on the display module can be single word or phrases to qualitatively indicate a risk or probability. For example, a word "unlikely" can be used to indicate a lower risk for having or developing pulmonary fibrosis, while "likely" can be used to indicate a high risk for having or developing pulmonary fibrosis.

In one embodiment of the invention, the content based on the computing and/or comparison result is displayed on a computer monitor. In one embodiment of the invention, the content based on the computing and/or comparison result is displayed through printable media. The display module can be any suitable device configured to receive from a computer and display computer readable information to a user. Non-limiting examples include, for example, general-purpose computers such as those based on Intel PENTIUM-type processor, Motorola PowerPC, Sun UltraSPARC, Hewlett-Packard PA-RISC processors, any of a variety of processors available from Advanced Micro Devices (AMD) of Sunnyvale, Calif., or any other type of processor, visual display devices such as flat panel displays, cathode ray tubes and the like, as well as computer printers of various types.

In one embodiment, a World Wide Web browser is used for providing a user interface for display of the content based on the computing/comparison result. It should be understood that other modules of the invention can be adapted to have a web browser interface. Through the Web browser, a user can construct requests for retrieving data from the computing/comparison module. Thus, the user will typically point and click to user interface elements such as buttons, pull down menus, scroll bars and the like conventionally employed in graphical user interfaces.

Systems and computer readable media described herein are merely illustrative embodiments of the invention for determining the level and/or activity of CHI3L1 in a sample obtained from a subject, and therefore are not intended to limit the scope of the invention. Variations of the systems and computer readable media described herein are possible and are intended to fall within the scope of the invention.

The modules of the machine, or those used in the computer readable medium, may assume numerous configurations. For example, function may be provided on a single machine or distributed over multiple machines.

For convenience, the meaning of some terms and phrases used in the specification, examples, and appended claims, are provided below. Unless stated otherwise, or implicit from context, the following terms and phrases include the meanings provided below. The definitions are provided to aid in describing particular embodiments, and are not intended to limit the claimed invention, because the scope of the invention is limited only by the claims. Unless otherwise defined, all technical and scientific terms used herein have the same meaning as commonly understood by one of ordinary skill in the art to which this invention belongs. If there is an apparent discrepancy between the usage of a term in the art and its definition provided herein, the definition provided within the specification shall prevail.

For convenience, certain terms employed herein, in the specification, examples and appended claims are collected here.

The terms "decrease", "reduced", "reduction", or "inhibit" are all used herein to mean a decrease by a statistically significant amount. In some embodiments, "reduce," "reduction" or "decrease" or "inhibit" typically means a decrease by at least 10% as compared to a reference level (e.g. the absence of a given treatment) and can include, for example, a decrease by at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 98%, at least about 99%, or more. As used herein, "reduction" or "inhibition" does not encompass a complete inhibition or reduction as compared to a reference level. "Complete inhibition" is a 100% inhibition as compared to a reference level. A decrease can be preferably down to a level accepted as within the range of normal for an individual without a given disorder.

The terms "increased", "increase", "enhance", or "activate" are all used herein to mean an increase by a statically significant amount. In some embodiments, the terms "increased", "increase", "enhance", or "activate" can mean an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level. In the context of a marker or symptom, a "increase" is a statistically significant increase in such level.

As used herein, a "subject" means a human or animal. Usually the animal is a vertebrate such as a primate, rodent, domestic animal or game animal Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. In some embodiments, the subject is a mammal, e.g., a primate, e.g., a human. The terms, "individual," "patient" and "subject" are used interchangeably herein.

Preferably, the subject is a mammal. The mammal can be a human, non-human primate, mouse, rat, dog, cat, horse, or cow, but is not limited to these examples. Mammals other than humans can be advantageously used as subjects that represent animal models of HPS and/or pulmonary fibrosis. A subject can be male or female.

A subject can be one who has been previously diagnosed with or identified as suffering from or having a condition in need of treatment (e.g. HPS and/or pulmonary fibrosis) or one or more complications related to such a condition, and optionally, have already undergone treatment for HPS or the one or more complications related to HPS (e g pulmonary fibrosis). Alternatively, a subject can also be one who has not been previously diagnosed as having, e.g., HPS or one or more complications related to HPS. For example, a subject can be one who exhibits one or more risk factors for HPS and/or pulmonary fibrosis or one or more complications related to HPS and/or pulmonary fibrosis or a subject who does not exhibit risk factors.

A "subject in need" of treatment for a particular condition can be a subject having that condition, diagnosed as having that condition, or at risk of developing that condition.

As used herein, the term "nucleic acid" or "nucleic acid sequence" refers to any molecule, preferably a polymeric molecule, incorporating units of ribonucleic acid, deoxyribonucleic acid or an analog thereof. The nucleic acid can be either single-stranded or double-stranded. A single-stranded nucleic acid can be one nucleic acid strand of a denatured double-stranded DNA. Alternatively, it can be a single-stranded nucleic acid not derived from any double-stranded DNA. In one aspect, the nucleic acid can be DNA. In another aspect, the nucleic acid can be RNA. Suitable nucleic acid molecules are DNA, including genomic DNA or cDNA. Other suitable nucleic acid molecules are RNA, including mRNA.

In some embodiments, an inhibitor of a gene expression product of a gene described herein (e.g. IL-13Ra2) can be an inhibitory nucleic acid. In some embodiments, the inhibitory nucleic acid is an inhibitory RNA (iRNA). Double-stranded RNA molecules (dsRNA) have been shown to block gene expression in a highly conserved regulatory mechanism known as RNA interference (RNAi). The inhibitory nucleic acids described herein can include an RNA strand (the antisense strand) having a region which is 30 nucleotides or less in length, i.e., 15-30 nucleotides in length, generally 19-24 nucleotides in length, which region is substantially complementary to at least part of the targeted mRNA transcript. The use of these iRNAs permits the targeted degradation of mRNA transcripts, resulting in decreased expression and/or activity of the target.

As used herein, the term "iRNA" refers to an agent that contains RNA as that term is defined herein, and which mediates the targeted cleavage of an RNA transcript via an RNA-induced silencing complex (RISC) pathway. In one embodiment, an iRNA as described herein effects inhibition of the expression and/or activity of, e.g., IL-13Rα2. In certain embodiments, contacting a cell with the inhibitor (e.g. an iRNA) results in a decrease in the target mRNA level in a cell by at least about 5%, about 10%, about 20%, about 30%, about 40%, about 50%, about 60%, about 70%, about 80%, about 90%, about 95%, about 99%, up to and including 100% of the target mRNA level found in the cell without the presence of the iRNA.

In some embodiments, the iRNA can be a dsRNA. A dsRNA includes two RNA strands that are sufficiently complementary to hybridize to form a duplex structure under conditions in which the dsRNA will be used. One strand of a dsRNA (the antisense strand) includes a region of complementarity that is substantially complementary, and generally fully complementary, to a target sequence. The target sequence can be derived from the sequence of an mRNA formed during the expression of the target. The other strand (the sense strand) includes a region that is complementary to the antisense strand, such that the two strands hybridize and form a duplex structure when combined under suitable conditions. Generally, the duplex structure is between 15 and 30 inclusive, more generally between 18 and 25 inclusive, yet more generally between 19 and 24 inclusive, and most generally between 19 and 21 base pairs in length, inclusive. Similarly, the region of complementarity to the target sequence is between 15 and 30 inclusive, more generally between 18 and 25 inclusive, yet more generally between 19 and 24 inclusive, and most generally between 19 and 21 nucleotides in length, inclusive. In some embodiments, the dsRNA is between 15 and 20 nucleotides in length, inclusive, and in other embodiments, the dsRNA is between 25 and 30 nucleotides in length, inclusive. As the ordinarily skilled person will recognize, the targeted region of an RNA targeted for cleavage will most often be part of a larger RNA molecule, often an mRNA molecule. Where relevant, a "part" of an mRNA target is a contiguous sequence of an mRNA target of sufficient length to be a substrate for RNAi-directed cleavage (i.e., cleavage through a RISC pathway). dsRNAs having duplexes as short as 9 base pairs can, under some circumstances, mediate RNAi-directed RNA cleavage. Most often a target will be at least 15 nucleotides in length, preferably 15-30 nucleotides in length.

In yet another embodiment, the RNA of an iRNA, e.g., a dsRNA, is chemically modified to enhance stability or other beneficial characteristics. The nucleic acids may be synthesized and/or modified by methods well established in the art, such as those described in "Current protocols in nucleic acid chemistry," Beaucage, S. L. et al. (Edrs.), John Wiley & Sons, Inc., New York, N.Y., USA, which is hereby incorporated herein by reference. Modifications include, for example, (a) end modifications, e.g., 5' end modifications (phosphorylation, conjugation, inverted linkages, etc.), 3' end modifications (conjugation, DNA nucleotides, inverted linkages, etc.), (b) base modifications, e.g., replacement with stabilizing bases, destabilizing bases, or bases that base pair with an expanded repertoire of partners, removal of bases (abasic nucleotides), or conjugated bases, (c) sugar modifications (e.g., at the 2' position or 4' position) or replacement of the sugar, as well as (d) backbone modifications, including modification or replacement of the phosphodiester linkages. Specific examples of RNA compounds useful in the embodiments described herein include, but are not limited to RNAs containing modified backbones or no natural internucleoside linkages. RNAs having modified backbones include, among others, those that do not have a phosphorus atom in the backbone. For the purposes of this specification, and as sometimes referenced in the art, modified RNAs that do not have a phosphorus atom in their internucleoside backbone can also be considered to be oligonucleosides. In particular embodiments, the modified RNA will have a phosphorus atom in its internucleoside backbone.

Modified RNA backbones can include, for example, phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those) having inverted polarity wherein the adjacent pairs of nucleoside units are linked 3'-5' to 5'-3' or 2'-5' to 5'-2'. Various salts, mixed salts and free acid forms are also included. Representative U.S. patents that teach the preparation of the above phosphorus-containing linkages include, but are not limited to, U.S. Pat. Nos. 3,687,808; 4,469,863; 4,476,301; 5,023,243; 5,177,195; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,316; 5,550,111; 5,563,253; 5,571,799; 5,587,361; 5,625,050; 6,028,188; 6,124,445; 6,160,109; 6,169,170; 6,172,209; 6,239,265; 6,277,603; 6,326,199; 6,346,614; 6,444,423; 6,531,590; 6,534,639; 6,608,035; 6,683,167; 6,858,715; 6,867,294; 6,878,805; 7,015,315; 7,041,816; 7,273,933; 7,321,029; and U.S. Pat. RE39464, each of which is herein incorporated by reference Modified RNA backbones that do not include a phosphorus atom therein have backbones that are formed by short chain alkyl or cycloalkyl internucleoside linkages, mixed heteroatoms and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts. Representative U.S. patents that teach the preparation of the above oligonucleosides include, but are not limited to, U.S. Pat. Nos. 5,034,506; 5,166,315; 5,185,444; 5,214,134; 5,216,141; 5,235,033; 5,64,562; 5,264,564; 5,405,938; 5,434,257; 5,466,677; 5,470,967; 5,489,677; 5,541,307; 5,561,225; 5,596,086; 5,602,240; 5,608,046; 5,610,289; 5,618,704; 5,623,070; 5,663,312; 5,633,360; 5,677,437; and, 5,677,439, each of which is herein incorporated by reference.

In other RNA mimetics suitable or contemplated for use in iRNAs, both the sugar and the internucleoside linkage, i.e., the backbone, of the nucleotide units are replaced with novel groups. The base units are maintained for hybridization with an appropriate nucleic acid target compound. One such oligomeric compound, an RNA mimetic that has been shown to have excellent hybridization properties, is referred to as a peptide nucleic acid (PNA). In PNA compounds, the sugar backbone of an RNA is replaced with an amide containing backbone, in particular an aminoethylglycine backbone. The nucleobases are retained and are bound directly or indirectly to aza nitrogen atoms of the amide portion of the backbone. Representative U.S. patents that teach the preparation of PNA compounds include, but are not limited to, U.S. Pat. Nos. 5,539,082; 5,714,331; and 5,719,262, each of which is herein incorporated by reference. Further teaching of PNA compounds can be found, for example, in Nielsen et al., Science, 1991, 254, 1497-1500.

Some embodiments include RNAs with phosphorothioate backbones and oligonucleosides with heteroatom backbones, and in particular —$CH_2$—NH—$CH_2$—, —$CH_2$—N($CH_3$)—O—$CH_2$-[known as a methylene (methylimino) or MMI backbone], —$CH_2$—O—N($CH_3$)—$CH_2$—, —$CH_2$—N($CH_3$)—N($CH_3$)—$CH_2$— and —N($CH_3$)—$CH_2$—$CH_2$-[wherein the native phosphodiester backbone is represented as —O—P—O—$CH_2$-] of the above-referenced U.S. Pat. No. 5,489,677, and the amide backbones of the above-referenced U.S. Pat. No. 5,602,240. In some embodiments, the RNAs featured herein have morpholino backbone structures of the above-referenced U.S. Pat. No. 5,034,506.

Modified RNAs can also contain one or more substituted sugar moieties. The iRNAs, e.g., dsRNAs, featured herein can include one of the following at the 2' position: OH; F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. Exemplary suitable modifications include $O[(CH_2)_nO]_mCH_3$, $O(CH_2)_{.n}OCH_3$, $O(CH_2)_nNH_2$, $O(CH_2)_nCH_3$, $O(CH_2)_nONH_2$, and $O(CH_2)_nON[(CH_2)_nCH_3)]_2$, where n and m are from 1 to about 10. In other embodiments, dsRNAs include one of the following at the 2' position: $C_1$ to $C_{10}$ lower alkyl, substituted lower alkyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an iRNA, or a group for improving the pharmacodynamic properties of an iRNA, and other substituents having similar properties. In some embodiments, the modification includes a 2'-methoxyethoxy (2'-O—$CH_2CH_2OCH_3$, also known as 2'-O-(2-methoxyethyl) or 2'-MOE) (Martin et al., *Helv. Chim. Acta,* 1995, 78:486-504) i.e., an alkoxy-alkoxy group. Another exemplary modification is 2'-dimethylaminooxyethoxy, i.e., a O(CH$_2$)$_2$ON(CH$_3$)$_2$ group, also known as 2'-DMAOE, as described in examples herein below, and 2'-dimethylaminoethoxyethoxy (also known in the art as 2'-O-dimethylaminoethoxyethyl or 2'-DMAEOE), i.e., 2'-O—CH$_2$—O—CH$_2$—N(CH$_2$)$_2$, also described in examples herein below.

Other modifications include 2'-methoxy (2'-OCH$_3$), 2'-aminopropoxy (2'-OCH$_2$CH$_2$CH$_2$NH$_2$) and 2'-fluoro (2'-F). Similar modifications can also be made at other positions on the RNA of an iRNA, particularly the 3' position of the sugar on the 3' terminal nucleotide or in 2'-5' linked dsRNAs and the 5' position of 5' terminal nucleotide. iRNAs may also have sugar mimetics such as cyclobutyl moieties in place of the pentofuranosyl sugar. Representative U.S. patents that teach the preparation of such modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; and 5,700,920, certain of which are commonly owned with the instant application, and each of which is herein incorporated by reference.

An iRNA can also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl anal other 8-substituted adenines and guanines, 5-halo, particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine. Further nucleobases include those disclosed in U.S. Pat. No. 3,687,808, those disclosed in Modified Nucleosides in Biochemistry, Biotechnology and Medicine, Herdewijn, P. ed. Wiley-VCH, 2008; those disclosed in The Concise Encyclopedia Of Polymer Science And Engineering, pages 858-859, Kroschwitz, J. L, ed. John Wiley & Sons, 1990, these disclosed by Englisch et al., Angewandte Chemie, International Edition, 1991, 30, 613, and those disclosed by Sanghvi, Y S., Chapter 15, dsRNA Research and Applications, pages 289-302, Crooke, S. T. and Lebleu, B., Ed., CRC Press, 1993. Certain of these nucleobases are particularly useful for increasing the binding affinity of the oligomeric compounds featured in the invention. These include 5-substituted pyrimidines, 6-azapyrimidines and N-2, N-6 and 0-6 substituted purines, including 2-aminopropyladenine, 5-propynyluracil and 5-propynylcytosine. 5-methylcytosine substitutions have been shown to increase nucleic acid duplex stability by 0.6-1.2° C. (Sanghvi, Y. S., Crooke, S. T. and Lebleu, B., Eds., dsRNA Research and Applications, CRC Press, Boca Raton, 1993, pp. 276-278) and are exemplary base substitutions, even more particularly when combined with 2'-O-methoxyethyl sugar modifications.

Representative U.S. patents that teach the preparation of certain of the above noted modified nucleobases as well as other modified nucleobases include, but are not limited to, the above noted U.S. Pat. No. 3,687,808, as well as U.S. Pat. Nos. 4,845,205; 5,130,30; 5,134,066; 5,175,273; 5,367,066; 5,432,272; 5,457,187; 5,459,255; 5,484,908; 5,502,177; 5,525,711; 5,552,540; 5,587,469; 5,594,121, 5,596,091; 5,614,617; 5,681,941; 6,015,886; 6,147,200; 6,166,197; 6,222,025; 6,235,887; 6,380,368; 6,528,640; 6,639,062; 6,617,438; 7,045,610; 7,427,672; and 7,495,088, each of which is herein incorporated by reference, and U.S. Pat. No. 5,750,692, also herein incorporated by reference.

The RNA of an iRNA can also be modified to include one or more locked nucleic acids (LNA). A locked nucleic acid is a nucleotide having a modified ribose moiety in which the ribose moiety comprises an extra bridge connecting the 2' and 4' carbons. This structure effectively "locks" the ribose in the 3'-endo structural conformation. The addition of locked nucleic acids to siRNAs has been shown to increase siRNA stability in serum, and to reduce off-target effects (Elmen, J. et al., (2005) *Nucleic Acids Research* 33(1):439-447; Mook, O R. et al., (2007) *Mol Canc Ther* 6(3):833-843; Grunweller, A. et al., (2003) *Nucleic Acids Research* 31(12): 3185-3193). Representative U.S. Patents that teach the preparation of locked nucleic acid nucleotides include, but are not limited to, the following: U.S. Pat. Nos. 6,268,490; 6,670,461; 6,794,499; 6,998,484; 7,053,207; 7,084,125; and 7,399,845, each of which is herein incorporated by reference in its entirety.

Another modification of the RNA of an iRNA as described herein involves chemically linking to the RNA one or more ligands, moieties or conjugates that enhance the activity, cellular distribution, pharmacokinetic properties, or cellular uptake of the iRNA. Such moieties include but are not limited to lipid moieties such as a cholesterol moiety (Letsinger et al., Proc. Natl. Acid. Sci. USA, 1989, 86: 6553-6556), cholic acid (Manoharan et al., Biorg. Med. Chem. Let., 1994, 4:1053-1060), a thioether, e.g., beryl-S-tritylthiol (Manoharan et al., Ann. N.Y. Acad. Sci., 1992, 660:306-309; Manoharan et al., Biorg. Med. Chem. Let., 1993, 3:2765-2770), a thiocholesterol (Oberhauser et al., Nucl. Acids Res., 1992, 20:533-538), an aliphatic chain, e.g., dodecandiol or undecyl residues (Saison-Behmoaras et al., EMBO J, 1991, 10:1111-1118; Kabanov et al., FEBS Lett., 1990, 259:327-330; Svinarchuk et al., Biochimie, 1993, 75:49-54), a phospholipid, e.g., di-hexadecyl-rac-glycerol or triethyl-ammonium 1,2-di-O-hexadecyl-rac-glycero-3-phosphonate (Manoharan et al., Tetrahedron Lett., 1995, 36:3651-3654; Shea et al., Nucl. Acids Res., 1990, 18:3777-3783), a polyamine or a polyethylene glycol chain (Manoharan et al., Nucleosides & Nucleotides, 1995, 14:969-973), or adamantane acetic acid (Manoharan et al., Tetrahedron Left., 1995, 36:3651-3654), a palmityl moiety (Mishra et al., Biochim. Biophys. Acta, 1995, 1264:229-237), or an octadecylamine or hexylamino-carbonyloxycholesterol moiety (Crooke et al., J. Pharmacol. Exp. Ther., 1996, 277:923-937).

As used herein, the terms "protein" and "polypeptide" are used interchangeably herein to designate a series of amino acid residues, connected to each other by peptide bonds between the alpha-amino and carboxy groups of adjacent residues. The terms "protein", and "polypeptide" refer to a polymer of amino acids, including modified amino acids (e.g., phosphorylated, glycated, glycosylated, etc.) and amino acid analogs, regardless of its size or function. "Protein" and "polypeptide" are often used in reference to relatively large polypeptides, whereas the term "peptide" is often used in reference to small polypeptides, but usage of these terms in the art overlaps. The terms "protein" and "polypeptide" are used interchangeably herein when referring to a gene product and fragments thereof. Thus, exemplary polypeptides or proteins include gene products, naturally occurring proteins, homologs, orthologs, paralogs, fragments and other equivalents, variants, fragments, and analogs of the foregoing.

As used herein, a particular "polypeptide", e.g. an IL13Rα2 polypeptide can include the human polypeptide (e.g., SEQ ID NO: 2); as well as homologs from other species, including but not limited to bovine, dog, cat chicken, murine, rat, porcine, ovine, turkey, horse, fish, baboon and other primates. The terms also refer to fragments or variants of the native polypeptide that maintain at least 50% of the activity or effect of the native full length polypeptide, e.g. as measured in an appropriate animal model. Conservative substitution variants that maintain the activity of wildtype polypeptides will include a conservative substitution as defined herein. The identification of amino acids most likely to be tolerant of conservative substitution while maintaining at least 50% of the activity of the wildtype is guided by, for example, sequence alignment with homologs or paralogs from other species. Amino acids that are identical between homologs are less likely to tolerate change, while those showing conservative differences are obviously much more likely to tolerate conservative change in the context of an artificial variant. Similarly, positions with non-conservative differences are less likely to be critical to function and more likely to tolerate conservative substitution in an artificial variant. Variants can be tested for activity, for example, by administering the variant to an appropriate animal model of allograft rejection as described herein.

In some embodiments, a polypeptide, e.g., a IL13Rα2 polypeptide, can be a variant of a sequence described herein, e.g. a variant of a IL13Rα2 polypeptide comprising the amino acid sequence of SEQ ID NO: 2. In some embodiments, the variant is a conservative substitution variant. Variants can be obtained by mutations of native nucleotide sequences, for example. A "variant," as referred to herein, is a polypeptide substantially homologous to a native or reference polypeptide, but which has an amino acid sequence different from that of the native or reference polypeptide because of one or a plurality of deletions, insertions or substitutions. Polypeptide-encoding DNA sequences encompass sequences that comprise one or more additions, deletions, or substitutions of nucleotides when compared to a native or reference DNA sequence, but that encode a variant protein or fragment thereof that retains the relevant biological activity relative to the reference protein, e.g., at least 50% of the wildtype reference protein. As to amino acid sequences, one of skill will recognize that individual substitutions, deletions or additions to a nucleic acid, peptide, polypeptide, or protein sequence which alters a single amino acid or a small percentage, (i.e. 5% or fewer, e.g. 4% or fewer, or 3% or fewer, or 1% or fewer) of amino acids in the encoded sequence is a "conservatively modified variant" where the alteration results in the substitution of an amino acid with a chemically similar amino acid. It is contemplated that some changes can potentially improve the relevant activity, such that a variant, whether conservative or note, has more than 100% of the activity of wildtype, e.g. 110%, 125%, 150%, 175%, 200%, 500%, 1000% or more.

One method of identifying amino acid residues which can be substituted is to align, for example, the human polypeptide to a homolog from one or more non-human species. Alignment can provide guidance regarding not only residues likely to be necessary for function but also, conversely, those residues likely to tolerate change. Where, for example, an alignment shows two identical or similar amino acids at corresponding positions, it is more likely that that site is important functionally. Where, conversely, alignment shows residues in corresponding positions to differ significantly in size, charge, hydrophobicity, etc., it is more likely that that site can tolerate variation in a functional polypeptide. The variant amino acid or DNA sequence can be at least 90%, at least 95%, at least 96%, at least 97%, at least 98%, at least 99%, or more, identical to a native or reference sequence, e.g. SEQ ID NOs: 2, 4, 6, 8, or 10 or a nucleic acid encoding one of those amino acid sequences. The degree of homology (percent identity) between a native and a mutant sequence can be determined, for example, by comparing the two sequences using freely available computer programs commonly employed for this purpose on the world wide web. The variant amino acid or DNA sequence can be at least 90%, at least 91%, at least 92%, at least 93%, at least 94%, at least 95%, at least 96%, at least 97%, at least 98%, at least 99%, or more, similar to the sequence from which it is derived (referred to herein as an "original" sequence). The degree of similarity (percent similarity) between an original and a mutant sequence can be determined, for example, by using a similarity matrix. Similarity matrices are well known in the art and a number of tools for comparing two sequences using similarity matrices are freely available online, e.g. BLASTp (available on the world wide web at http://blast.ncbi.nlm.nih.gov), with default parameters set.

A given amino acid can be replaced by a residue having similar physiochemical characteristics, e.g., substituting one aliphatic residue for another (such as Ile, Val, Leu, or Ala for one another), or substitution of one polar residue for another (such as between Lys and Arg; Glu and Asp; or Gln and Asn). Other such conservative substitutions, e.g., substitutions of entire regions having similar hydrophobicity characteristics, are well known. Polypeptides comprising conservative amino acid substitutions can be tested in any one of the assays described herein to confirm that a desired activity of a native or reference polypeptide is retained. Conservative substitution tables providing functionally similar amino acids are well known in the art. Such conservatively modified variants are in addition to and do not exclude polymorphic variants, interspecies homologs, and alleles consistent with the disclosure. Typically conservative substitutions for one another include: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, Proteins (1984)).

Any cysteine residue not involved in maintaining the proper conformation of the polypeptide also can be substituted, generally with serine, to improve the oxidative stability of the molecule and prevent aberrant crosslinking. Conversely, cysteine bond(s) can be added to the polypeptide to improve its stability or facilitate oligomerization.

In some embodiments, a polypeptide, e.g., a IL13Rα2 polypeptide, administered to a subject can comprise one or more amino acid substitutions or modifications. In some embodiments, the substitutions and/or modifications can prevent or reduce proteolytic degradation and/or prolong half-life of the polypeptide in the subject. In some embodiments, a polypeptide can be modified by conjugating or fusing it to other polypeptide or polypeptide domains such as, by way of non-limiting example, transferrin (WO06096515A2), albumin (Yeh et al., 1992), growth hormone (US2003104578AA); cellulose (Levy and Shoseyov, 2002); and/or Fc fragments (Ashkenazi and Chamow, 1997). The references in the foregoing paragraph are incorporated by reference herein in their entireties.

In some embodiments, a polypeptide, e.g., an IL13Rα2 polypeptide, as described herein can comprise at least one peptide bond replacement. A single peptide bond or multiple peptide bonds, e.g. 2 bonds, 3 bonds, 4 bonds, 5 bonds, or 6 or more bonds, or all the peptide bonds can be replaced. An isolated peptide as described herein can comprise one type of peptide bond replacement or multiple types of peptide bond replacements, e.g. 2 types, 3 types, 4 types, 5 types, or more types of peptide bond replacements. Non-limiting examples of peptide bond replacements include urea, thiourea, carbamate, sulfonyl urea, trifluoroethylamine, ortho-(aminoalkyl)-phenylacetic acid, para-(aminoalkyl)-phenylacetic acid, meta-(aminoalkyl)-phenylacetic acid, thioamide, tetrazole, boronic ester, olefinic group, and derivatives thereof.

In some embodiments, a polypeptide, e.g., an IL13Rα2 polypeptide, as described herein can comprise naturally occurring amino acids commonly found in polypeptides and/or proteins produced by living organisms, e.g. Ala (A), Val (V), Leu (L), Ile (I), Pro (P), Phe (F), Trp (W), Met (M), Gly (G), Ser (S), Thr (T), Cys (C), Tyr (Y), Asn (N), Gln (Q), Asp (D), Glu (E), Lys (K), Arg (R), and His (H). In some embodiments, an IL13Rα2 polypeptide as described herein can comprise alternative amino acids. Non-limiting examples of alternative amino acids include, D-amino acids; beta-amino acids; homocysteine, phosphoserine, phosphothreonine, phosphotyrosine, hydroxyproline, gamma-carboxyglutamate; hippuric acid, octahydroindole-2-carboxylic acid, statine, 1,2,3,4,-tetrahydroisoquinoline-3-carboxylic acid, penicillamine (3-mercapto-D-valine), ornithine, citrulline, alpha-methyl-alanine, para-benzoylphenylalanine, para-amino phenylalanine, p-fluorophenylalanine, phenylglycine, propargylglycine, sarcosine, and tert-butylglycine), diaminobutyric acid, 7-hydroxy-tetrahydroisoquinoline carboxylic acid, naphthylalanine, biphenylalanine, cyclohexylalanine, amino-isobutyric acid, norvaline, norleucine, tert-leucine, tetrahydroisoquinoline carboxylic acid, pipecolic acid, phenylglycine, homophenylalanine, cyclohexylglycine, dehydroleucine, 2,2-diethylglycine, 1-amino-1-cyclopentanecarboxylic acid, 1-amino-1-cyclohexanecarboxylic acid, amino-benzoic acid, amino-naphthoic acid, gamma-aminobutyric acid, difluorophenylalanine, nipecotic acid, alpha-amino butyric acid, thienyl-alanine, t-butylglycine, trifluorovaline; hexafluoroleucine; fluorinated analogs; azide-modified amino acids; alkyne-modified amino acids; cyano-modified amino acids; and derivatives thereof.

In some embodiments, a polypeptide, e.g. an IL13Rα2 polypeptide, can be modified, e.g. by addition of a moiety to one or more of the amino acids comprising the peptide. In some embodiments, a polypeptide as described herein can comprise one or more moiety molecules, e.g. 1 or more moiety molecules per peptide, 2 or more moiety molecules per peptide, 5 or more moiety molecules per peptide, 10 or more moiety molecules per peptide or more moiety molecules per peptide. In some embodiments, a polypeptide as described herein can comprise one more types of modifications and/or moieties, e.g. 1 type of modification, 2 types of modifications, 3 types of modifications or more types of modifications. Non-limiting examples of modifications and/or moieties include PEGylation; glycosylation; HESylation; ELPylation; lipidation; acetylation; amidation; end-capping modifications; cyano groups; phosphorylation; albumin, and cyclization. In some embodiments, an end-capping modification can comprise acetylation at the N-terminus, N-terminal acylation, and N-terminal formylation. In some embodiments, an end-capping modification can comprise amidation at the C-terminus, introduction of C-terminal alcohol, aldehyde, ester, and thioester moieties. The half-life of a polypeptide can be increased by the addition of moieties, e.g. PEG or albumin.

In some embodiments, the polypeptide administered to the subject (or a nucleic acid encoding such a polypeptide) can be a functional fragment of one of the amino acid sequences described herein. As used herein, a "functional fragment" is a fragment or segment of a peptide which retains at least 50% of the wildtype reference polypeptide's activity according to the assays described below herein. A functional fragment can comprise conservative substitutions of the sequences disclosed herein.

Alterations of the original amino acid sequence can be accomplished by any of a number of techniques known to one of skill in the art. Mutations can be introduced, for example, at particular loci by synthesizing oligonucleotides containing a mutant sequence, flanked by restriction sites permitting ligation to fragments of the native sequence. Following ligation, the resulting reconstructed sequence encodes an analog having the desired amino acid insertion, substitution, or deletion. Alternatively, oligonucleotide-directed site-specific mutagenesis procedures can be employed to provide an altered nucleotide sequence having particular codons altered according to the substitution, deletion, or insertion required. Techniques for making such alterations include those disclosed by Walder et al. (Gene 42:133, 1986); Bauer et al. (Gene 37:73, 1985); Craik (BioTechniques, January 1985, 12-19); Smith et al. (Genetic Engineering: Principles and Methods, Plenum Press, 1981); and U.S. Pat. Nos. 4,518,584 and 4,737,462, which are herein incorporated by reference in their entireties. In some embodiments, a polypeptide as described herein can be chemically synthesized and mutations can be incorporated as part of the chemical synthesis process.

In some embodiments, a polypeptide, e.g., an IL13Rα2 polypeptide, as described herein can be formulated as a pharmaceutically acceptable prodrug. As used herein, a "prodrug" refers to compounds that can be converted via some chemical or physiological process (e.g., enzymatic processes and metabolic hydrolysis) to a therapeutic agent. Thus, the term "prodrug" also refers to a precursor of a biologically active compound that is pharmaceutically acceptable. A prodrug may be inactive when administered to a subject, i.e. an ester, but is converted in vivo to an active compound, for example, by hydrolysis to the free carboxylic acid or free hydroxyl. The prodrug compound often offers advantages of solubility, tissue compatibility or delayed release in an organism. The term "prodrug" is also meant to include any covalently bonded carriers, which release the active compound in vivo when such prodrug is administered to a subject. Prodrugs of an active compound may be prepared by modifying functional groups present in the active compound in such a way that the modifications are cleaved, either in routine manipulation or in vivo, to the parent active compound. Prodrugs include compounds wherein a hydroxy, amino or mercapto group is bonded to any group that, when the prodrug of the active compound is administered to a subject, cleaves to form a free hydroxy, free amino or free mercapto group, respectively. Examples of prodrugs include, but are not limited to, acetate, formate and benzoate derivatives of an alcohol or acetamide, formamide and benzamide derivatives of an amine functional group in the active compound and the like. See Harper, "Drug Latentiation" in Jucker, ed. *Progress in Drug*

Research 4:221-294 (1962); Morozowich et al, "Application of Physical Organic Principles to Prodrug Design" in E. B. Roche ed. *Design of Biopharmaceutical Properties through Prodrugs and Analogs*, APHA Acad. Pharm. Sci. 40 (1977); *Bioreversible Carriers in Drug in Drug Design, Theory and Application*, E. B. Roche, ed., APHA Acad. Pharm. Sci. (1987); *Design of Prodrugs*, H. Bundgaard, Elsevier (1985); Wang et al. "Prodrug approaches to the improved delivery of peptide drug" in *Curr. Pharm. Design.* 5(4):265-287 (1999); Pauletti et al. (1997) Improvement in peptide bioavailability: Peptidomimetics and Prodrug Strategies, *Adv. Drug. Delivery Rev.* 27:235-256; Mizen et al. (1998) "The Use of Esters as Prodrugs for Oral Delivery of (3-Lactam antibiotics," *Pharm. Biotech.* 11:345-365; Gaignault et al. (1996) "Designing Prodrugs and Bioprecursors I. Carrier Prodrugs," *Pract. Med. Chem.* 671-696; Asgharnejad, "Improving Oral Drug Transport", in *Transport Processes in Pharmaceutical Systems*, G. L. Amidon, P. I. Lee and E. M. Topp, Eds., Marcell Dekker, p. 185-218 (2000); Balant et al., "Prodrugs for the improvement of drug absorption via different routes of administration", *Eur. J. Drug Metab. Pharmacokinet.*, 15(2): 143-53 (1990); Balimane and Sinko, "Involvement of multiple transporters in the oral absorption of nucleoside analogues", *Adv. Drug Delivery Rev.*, 39(1-3): 183-209 (1999); Browne, "Fosphenytoin (Cerebyx)", *Clin. Neuropharmacol.* 20(1): 1-12 (1997); Bundgaard, "Bioreversible derivatization of drugs—principle and applicability to improve the therapeutic effects of drugs", *Arch. Pharm. Chemi* 86(1): 1-39 (1979); Bundgaard H. "Improved drug delivery by the prodrug approach", *Controlled Drug Delivery* 17: 179-96 (1987); Bundgaard H. "Prodrugs as a means to improve the delivery of peptide drugs", *Arfv. Drug Delivery Rev.* 8(1): 1-38 (1992); Fleisher et al. "Improved oral drug delivery: solubility limitations overcome by the use of prodrugs", *Arfv. Drug Delivery Rev.* 19(2): 115-130 (1996); Fleisher et al. "Design of prodrugs for improved gastrointestinal absorption by intestinal enzyme targeting", *Methods Enzymol.* 112 (Drug Enzyme Targeting, Pt. A): 360-81, (1985); Farquhar D, et al., "Biologically Reversible Phosphate-Protective Groups", *Pharm. Sci.*, 72(3): 324-325 (1983); Freeman S, et al., "Bioreversible Protection for the Phospho Group: Chemical Stability and Bioactivation of Di(4-acetoxy-benzyl) Methylphosphonate with Carboxyesterase," *Chem. Soc., Chem. Commun.*, 875-877 (1991); Friis and Bundgaard, "Prodrugs of phosphates and phosphonates: Novel lipophilic alphaacyloxyalkyl ester derivatives of phosphate- or phosphonate containing drugs masking the negative charges of these groups", *Eur. J. Pharm. Sci.* 4: 49-59 (1996); Gangwar et al., "Pro-drug, molecular structure and percutaneous delivery", *Des. Biopharm. Prop. Prodrugs Analogs, [Symp.]* Meeting Date 1976, 409-21. (1977); Nathwani and Wood, "Penicillins: a current review of their clinical pharmacology and therapeutic use", *Drugs* 45(6): 866-94 (1993); Sinhababu and Thakker, "Prodrugs of anticancer agents", *Adv. Drug Delivery Rev.* 19(2): 241-273 (1996); Stella et al., "Prodrugs. Do they have advantages in clinical practice?", *Drugs* 29(5): 455-73 (1985); Tan et al. "Development and optimization of anti-HIV nucleoside analogs and prodrugs: A review of their cellular pharmacology, structure-activity relationships and pharmacokinetics", *Adv. Drug Delivery Rev.* 39(1-3): 117-151 (1999); Taylor, "Improved passive oral drug delivery via prodrugs", *Adv. Drug Delivery Rev.*, 19(2): 131-148 (1996); Valentino and Borchardt, "Prodrug strategies to enhance the intestinal absorption of peptides", *Drug Discovery Today* 2(4): 148-155 (1997); Wiebe and Knaus, "Concepts for the design of anti-HIV nucleoside prodrugs for treating cephalic HIV infection", *Adv. Drug Delivery Rev.*: 39(1-3):63-80 (1999); Waller et al., "Prodrugs", *Br. J. Clin. Pharmac.* 28: 497-507 (1989), which are incorporated by reference herein in their entireties.

In some embodiments, a polypeptide as described herein can be a pharmaceutically acceptable solvate. The term "solvate" refers to a peptide as described herein in the solid state, wherein molecules of a suitable solvent are incorporated in the crystal lattice. A suitable solvent for therapeutic administration is physiologically tolerable at the dosage administered. Examples of suitable solvents for therapeutic administration are ethanol and water. When water is the solvent, the solvate is referred to as a hydrate. In general, solvates are formed by dissolving the compound in the appropriate solvent and isolating the solvate by cooling or using an antisolvent. The solvate is typically dried or azeotroped under ambient conditions.

The peptides of the present invention can be synthesized by using well known methods including recombinant methods and chemical synthesis. Recombinant methods of producing a peptide through the introduction of a vector including nucleic acid encoding the peptide into a suitable host cell is well known in the art, such as is described in Sambrook et al., Molecular Cloning: A Laboratory Manual, 2d Ed, Vols 1 to 8, Cold Spring Harbor, N.Y. (1989); M. W. Pennington and B. M. Dunn, Methods in Molecular Biology: Peptide Synthesis Protocols, Vol 35, Humana Press, Totawa, N.J. (1994), contents of both of which are herein incorporated by reference. Peptides can also be chemically synthesized using methods well known in the art. See for example, Merrifield et al., J. Am. Chem. Soc. 85:2149 (1964); Bodanszky, M., Principles of Peptide Synthesis, Springer-Verlag, New York, N.Y. (1984); Kimmerlin, T. and Seebach, D. J. Pept. Res. 65:229-260 (2005); Nilsson et al., Annu. Rev. Biophys. Biomol. Struct. (2005) 34:91-118; W. C. Chan and P. D. White (Eds.) Fmoc Solid Phase Peptide Synthesis: A Practical Approach, Oxford University Press, Cary, N.C. (2000); N. L. Benoiton, Chemistry of Peptide Synthesis, CRC Press, Boca Raton, Fla. (2005); J. Jones, Amino Acid and Peptide Synthesis, $2^{nd}$ Ed, Oxford University Press, Cary, N.C. (2002); and P. Lloyd-Williams, F. Albericio, and E. Giralt, Chemical Approaches to the synthesis of peptides and proteins, CRC Press, Boca Raton, Fla. (1997), contents of all of which are herein incorporated by reference. Peptide derivatives can also be prepared as described in U.S. Pat. Nos. 4,612,302; 4,853,371; and 4,684,620, and U.S. Pat. App. Pub. No. 2009/0263843, contents of all which are herein incorporated by reference.

In some embodiments, the technology described herein relates to a nucleic acid encoding a polypeptide (e.g. an IL13Rα2 polypeptide) as described herein. As used herein, the term "nucleic acid" or "nucleic acid sequence" refers to any molecule, preferably a polymeric molecule, incorporating units of ribonucleic acid, deoxyribonucleic acid or an analog thereof. The nucleic acid can be either single-stranded or double-stranded. A single-stranded nucleic acid can be one strand nucleic acid of a denatured double-stranded DNA. Alternatively, it can be a single-stranded nucleic acid not derived from any double-stranded DNA. In one aspect, the template nucleic acid is DNA. In another aspect, the template is RNA. Suitable nucleic acid molecules are DNA, including genomic DNA or cDNA. Other suitable nucleic acid molecules are RNA, including mRNA. The nucleic acid molecule can be naturally occurring, as in genomic DNA, or it may be synthetic, i.e., prepared based up human action, or may be a combination of the two. The nucleic acid molecule can also have certain modification such as 2'-deoxy, 2'-deoxy-2'-fluoro, 2'-O-methyl, 2'-O-methoxyethyl (2'-O-MOE), 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), or 2'-O—N-methylacetamido (2'-O-NMA), cholesterol addition, and phosphorothioate backbone as described in US Patent Application 20070213292; and certain ribonucleoside that are is linked between the 2'-oxygen and the 4'-carbon atoms with a methylene unit as described in U.S. Pat. No. 6,268,490, wherein both patent and patent application are incorporated hereby reference in their entirety.

In some embodiments, a nucleic acid encoding a polypeptide as described herein (e.g. an IL13Rα2 polypeptide) is comprised by a vector. In some of the aspects described herein, a nucleic acid sequence encoding a given polypeptide as described herein, or any module thereof, is operably linked to a vector. The term "vector", as used herein, refers to a nucleic acid construct designed for delivery to a host cell or for transfer between different host cells. As used herein, a vector can be viral or non-viral. The term "vector" encompasses any genetic element that is capable of replication when associated with the proper control elements and that can transfer gene sequences to cells. A vector can include, but is not limited to, a cloning vector, an expression vector, a plasmid, phage, transposon, cosmid, chromosome, virus, virion, etc.

As used herein, the term "expression vector" refers to a vector that directs expression of an RNA or polypeptide from sequences linked to transcriptional regulatory sequences on the vector. The sequences expressed will often, but not necessarily, be heterologous to the cell. An expression vector may comprise additional elements, for example, the expression vector may have two replication systems, thus allowing it to be maintained in two organisms, for example in human cells for expression and in a prokaryotic host for cloning and amplification. The term "expression" refers to the cellular processes involved in producing RNA and proteins and as appropriate, secreting proteins, including where applicable, but not limited to, for example, transcription, transcript processing, translation and protein folding, modification and processing. "Expression products" include RNA transcribed from a gene, and polypeptides obtained by translation of mRNA transcribed from a gene. The term "gene" means the nucleic acid sequence which is transcribed (DNA) to RNA in vitro or in vivo when operably linked to appropriate regulatory sequences. The gene may or may not include regions preceding and following the coding region, e.g. 5' untranslated (5'UTR) or "leader" sequences and 3' UTR or "trailer" sequences, as well as intervening sequences (introns) between individual coding segments (exons).

As used herein, the term "viral vector" refers to a nucleic acid vector construct that includes at least one element of viral origin and has the capacity to be packaged into a viral vector particle. The viral vector can contain the nucleic acid encoding a polypeptide as described herein in place of non-essential viral genes. The vector and/or particle may be utilized for the purpose of transferring any nucleic acids into cells either in vitro or in vivo. Numerous forms of viral vectors are known in the art.

By "recombinant vector" is meant a vector that includes a heterologous nucleic acid sequence, or "transgene" that is capable of expression in vivo. It should be understood that the vectors described herein can, in some embodiments, be combined with other suitable compositions and therapies. In some embodiments, the vector is episomal. The use of a suitable episomal vector provides a means of maintaining the nucleotide of interest in the subject in high copy number extra chromosomal DNA thereby eliminating potential effects of chromosomal integration.

In some embodiments, an inhibitor of a given polypeptide can be an antibody reagent specific for that polypeptide. As used herein an "antibody" refers to IgG, IgM, IgA, IgD or IgE molecules or antigen-specific antibody fragments thereof (including, but not limited to, a Fab, F(ab')$_2$, Fv, disulphide linked Fv, scFv, single domain antibody, closed conformation multispecific antibody, disulphide-linked scfv, diabody), whether derived from any species that naturally produces an antibody, or created by recombinant DNA technology; whether isolated from serum, B-cells, hybridomas, transfectomas, yeast or bacteria.

As described herein, an "antigen" is a molecule that is bound by a binding site on an antibody agent. Typically, antigens are bound by antibody ligands and are capable of raising an antibody response in vivo. An antigen can be a polypeptide, protein, nucleic acid or other molecule or portion thereof. The term "antigenic determinant" refers to an epitope on the antigen recognized by an antigen-binding molecule, and more particularly, by the antigen-binding site of said molecule.

As used herein, the term "antibody reagent" refers to a polypeptide that includes at least one immunoglobulin variable domain or immunoglobulin variable domain sequence and which specifically binds a given antigen. An antibody reagent can comprise an antibody or a polypeptide comprising an antigen-binding domain of an antibody. In some embodiments, an antibody reagent can comprise a monoclonal antibody or a polypeptide comprising an antigen-binding domain of a monoclonal antibody. For example, an antibody can include a heavy (H) chain variable region (abbreviated herein as VH), and a light (L) chain variable region (abbreviated herein as VL). In another example, an antibody includes two heavy (H) chain variable regions and two light (L) chain variable regions. The term "antibody reagent" encompasses antigen-binding fragments of antibodies (e.g., single chain antibodies, Fab and sFab fragments, F(ab')2, Fd fragments, Fv fragments, scFv, and domain antibodies (dAb) fragments (see, e.g. de Wildt et al., Eur J. Immunol. 1996; 26(3):629-39; which is incorporated by reference herein in its entirety)) as well as complete antibodies. An antibody can have the structural features of IgA, IgG, IgE, IgD, IgM (as well as subtypes and combinations thereof). Antibodies can be from any source, including mouse, rabbit, pig, rat, and primate (human and non-human primate) and primatized antibodies. Antibodies also include midibodies, humanized antibodies, chimeric antibodies, and the like.

The VH and VL regions can be further subdivided into regions of hypervariability, termed "complementarity determining regions" ("CDR"), interspersed with regions that are more conserved, termed "framework regions" ("FR"). The extent of the framework region and CDRs has been precisely defined (see, Kabat, E. A., et al. (1991) Sequences of Proteins of Immunological Interest, Fifth Edition, U.S. Department of Health and Human Services, NIH Publication No. 91-3242, and Chothia, C. et al. (1987) J. Mol. Biol. 196:901-917; which are incorporated by reference herein in their entireties). Each VH and VL is typically composed of three CDRs and four FRs, arranged from amino-terminus to carboxy-terminus in the following order: FR1, CDR1, FR2, CDR2, FR3, CDR3, FR4.

The terms "antigen-binding fragment" or "antigen-binding domain", which are used interchangeably herein are used to refer to one or more fragments of a full length antibody that retain the ability to specifically bind to a target of interest. Examples of binding fragments encompassed within the term "antigen-binding fragment" of a full length antibody include (i) a Fab fragment, a monovalent fragment consisting of the VL, VH, CL and CH1 domains; (ii) a F(ab')2 fragment, a bivalent fragment including two Fab fragments linked by a disulfide bridge at the hinge region; (iii) an Fd fragment consisting of the VH and CH1 domains; (iv) an Fv fragment consisting of the VL and VH domains of a single arm of an antibody, (v) a dAb fragment (Ward et al., (1989) Nature 341:544-546; which is incorporated by reference herein in its entirety), which consists of a VH or VL domain; and (vi) an isolated complementarity determining region (CDR) that retains specific antigen-binding functionality.

As used herein, the term "specific binding" refers to a chemical interaction between two molecules, compounds, cells and/or particles wherein the first entity binds to the second, target entity with greater specificity and affinity than it binds to a third entity which is a non-target. In some embodiments, specific binding can refer to an affinity of the first entity for the second target entity which is at least 10 times, at least 50 times, at least 100 times, at least 500 times, at least 1000 times or greater than the affinity for the third nontarget entity. A reagent specific for a given target is one that exhibits specific binding for that target under the conditions of the assay being utilized.

Additionally, and as described herein, a recombinant humanized antibody can be further optimized to decrease potential immunogenicity, while maintaining functional activity, for therapy in humans. In this regard, functional activity means a polypeptide capable of displaying one or more known functional activities associated with a recombinant antibody or antibody reagent thereof as described herein. Such functional activities include, e.g. the ability to bind to e.g., CRTH2.

As used herein, "expression level" refers to the number of mRNA molecules and/or polypeptide molecules encoded by a given gene that are present in a cell or sample. Expression levels can be increased or decreased relative to a reference level.

As used herein, the terms "treat," "treatment," "treating," or "amelioration" refer to therapeutic treatments, wherein the object is to reverse, alleviate, ameliorate, inhibit, slow down or stop the progression or severity of a condition associated with a disease or disorder, e.g. HPS or pulmonary fibrosis. The term "treating" includes reducing or alleviating at least one adverse effect or symptom of a condition, disease or disorder, e.g. HPS or pulmonary fibrosis. Treatment is generally "effective" if one or more symptoms or clinical markers are reduced. Alternatively, treatment is "effective" if the progression of a disease is reduced or halted. That is, "treatment" includes not just the improvement of symptoms or markers, but also a cessation of, or at least slowing of, progress or worsening of symptoms compared to what would be expected in the absence of treatment. Beneficial or desired clinical results include, but are not limited to, alleviation of one or more symptom(s), diminishment of extent of disease, stabilized (i.e., not worsening) state of disease, delay or slowing of disease progression, amelioration or palliation of the disease state, remission (whether partial or total), and/or decreased mortality, whether detectable or undetectable. The term "treatment" of a disease also includes providing relief from the symptoms or side-effects of the disease (including palliative treatment).

As used herein, the term "pharmaceutical composition" refers to the active agent in combination with a pharmaceutically acceptable carrier e.g. a carrier commonly used in the pharmaceutical industry. The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, the term "administering," refers to the placement of a compound as disclosed herein into a subject by a method or route which results in at least partial delivery of the agent at a desired site. Pharmaceutical compositions comprising the compounds disclosed herein can be administered by any appropriate route which results in an effective treatment in the subject.

The term "statistically significant" or "significantly" refers to statistical significance and generally means a two standard deviation (2SD) or greater difference.

Other than in the operating examples, or where otherwise indicated, all numbers expressing quantities of ingredients or reaction conditions used herein should be understood as modified in all instances by the term "about." The term "about" when used in connection with percentages can mean±1%.

As used herein the term "comprising" or "comprises" is used in reference to compositions, methods, and respective component(s) thereof, that are essential to the method or composition, yet open to the inclusion of unspecified elements, whether essential or not.

The term "consisting of" refers to compositions, methods, and respective components thereof as described herein, which are exclusive of any element not recited in that description of the embodiment.

As used herein the term "consisting essentially of" refers to those elements required for a given embodiment. The term permits the presence of elements that do not materially affect the basic and novel or functional characteristic(s) of that embodiment.

The singular terms "a," "an," and "the" include plural referents unless context clearly indicates otherwise. Similarly, the word "or" is intended to include "and" unless the context clearly indicates otherwise. Although methods and materials similar or equivalent to those described herein can be used in the practice or testing of this disclosure, suitable methods and materials are described below. The abbreviation, "e.g." is derived from the Latin exempli gratia, and is used herein to indicate a non-limiting example. Thus, the abbreviation "e.g." is synonymous with the term "for example."

Definitions of common terms in cell biology and molecular biology can be found in "The Merck Manual of Diagnosis and Therapy", 19th Edition, published by Merck Research Laboratories, 2006 (ISBN 0-911910-19-0); Robert S. Porter et al. (eds.), The Encyclopedia of Molecular Biology, published by Blackwell Science Ltd., 1994 (ISBN 0-632-02182-9); Benjamin Lewin, Genes X, published by Jones & Bartlett Publishing, 2009 (ISBN-10: 0763766321); Kendrew et al. (eds.), Biology and Biotechnology: a Comprehensive Desk Reference, published by VCH Publishers, Inc., 1995 (ISBN 1-56081-569-8) and Current Protocols in Protein Sciences 2009, Wiley Intersciences, Coligan et al., eds.

Unless otherwise stated, the present invention was performed using standard procedures, as described, for example in Sambrook et al., Molecular Cloning: A Laboratory Manual (4 ed.), Cold Spring Harbor Laboratory Press, Cold Spring Harbor, N.Y., USA (2012); Davis et al., Basic Methods in Molecular Biology, Elsevier Science Publishing, Inc., New York, USA (1995); or Methods in Enzymology: Guide to Molecular Cloning Techniques Vol. 152, S. L. Berger and A. R. Kimmel Eds., Academic Press Inc., San Diego, USA (1987); Current Protocols in Protein Science (CPPS) (John E. Coligan, et. al., ed., John Wiley and Sons, Inc.), Current Protocols in Cell Biology (CPCB) (Juan S. Bonifacino et. al. ed., John Wiley and Sons, Inc.), and Culture of Animal Cells: A Manual of Basic Technique by R. Ian Freshney, Publisher: Wiley-Liss; 5th edition (2005), Animal Cell Culture Methods (Methods in Cell Biology, Vol. 57, Jennie P. Mather and David Barnes editors, Academic Press, 1st edition, 1998) which are all incorporated by reference herein in their entireties.

Other terms are defined herein within the description of the various aspects of the invention.

All patents and other publications; including literature references, issued patents, published patent applications, and co-pending patent applications; cited throughout this application are expressly incorporated herein by reference for the purpose of describing and disclosing, for example, the methodologies described in such publications that might be used in connection with the technology described herein. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The description of embodiments of the disclosure is not intended to be exhaustive or to limit the disclosure to the precise form disclosed. While specific embodiments of, and examples for, the disclosure are described herein for illustrative purposes, various equivalent modifications are possible within the scope of the disclosure, as those skilled in the relevant art will recognize. For example, while method steps or functions are presented in a given order, alternative embodiments may perform functions in a different order, or functions may be performed substantially concurrently. The teachings of the disclosure provided herein can be applied to other procedures or methods as appropriate. The various embodiments described herein can be combined to provide further embodiments. Aspects of the disclosure can be modified, if necessary, to employ the compositions, functions and concepts of the above references and application to provide yet further embodiments of the disclosure. Moreover, due to biological functional equivalency considerations, some changes can be made in protein structure without affecting the biological or chemical action in kind or amount. These and other changes can be made to the disclosure in light of the detailed description. All such modifications are intended to be included within the scope of the appended claims.

Specific elements of any of the foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

The technology described herein is further illustrated by the following examples which in no way should be construed as being further limiting.

Some embodiments of the technology described herein can be defined according to any of the following numbered paragraphs:

1. A method of treating Hermansky Pudlak Syndrome (HPS) in a subject in need thereof, the method comprising administering an agonist of IL-13Rα2 and/or an inhibitor of CRTH2 to the subject.
2. A method of treating pulmonary fibrosis in a subject in need of treatment for Hermansky Pudlak Syndrome (HPS), the method comprising administering an agonist of IL-13Rα2 and/or an inhibitor of CRTH2 to the subject.
3. A method of treating pulmonary fibrosis in a subject determined to have Hermansky Pudlak Syndrome (HPS), the method comprising administering an agonist of IL-13Rα2 and/or an inhibitor of CRTH2 to the subject.
4. The method of any of paragraphs 1-3, wherein the subject is a subject identified as having an increased level of CHI3L1 expression and/or activity.
5. A method comprising:
    measuring the level of CHI3L1 in a test sample obtained from a subject with Hermansky Pudlak Syndrome (HPS);
    wherein an increase in the CHI3L1 level relative to a reference level indicates the subject has a higher risk of having or developing pulmonary fibrosis.
6. An assay comprising:
    contacting a sample obtained from the subject with Hermansky Pudlak Syndrome (HPS) with a CHI3L1-specific reagent to detect the presence or level of CHI3L1; measuring the presence or intensity of a signal which indicates the presence or level of CHI3L1 in the sample;
    wherein an increase in the CHI3L1 level relative to a reference level indicates the subject has a higher risk of having or developing pulmonary fibrosis.
7. A method for selecting a treatment regimen for a subject with Hermansky Pudlak Syndrome (HPS), comprising:
    contacting a sample obtained from the subject with Hermansky Pudlak Syndrome (HPD) with a CHI3L1-specific reagent to detect the presence or level of CHI3L1; measuring the presence or intensity of a signal which indicates the presence or level of CHI3L1 in the sample;
    selecting a treatment regimen comprising a treatment for pulmonary fibrosis when the subject has an increase in the CHI3L1 level relative to a reference level; and selecting a treatment regimen not comprising a treatment for pulmonary fibrosis when the subject does not have an increase in the CHI3L1 level relative to a reference level.
8. A method of identifying a subject with Hermansky Pudlak Syndrome (HPS) in need of treatment for pulmonary fibrosis, the method comprising:
    measuring the level of CHI3L1 in a test sample obtained from a subject; and identifying the subject as being in need of treatment for pulmonary fibrosis when the expression level of CHI3L1 is increased relative to a reference level.
9. A method of determining if a subject with Hermansky Pudlak Syndrome (HPS) is at risk for pulmonary fibrosis, the method comprising:

measuring the level of CHI3L1 in a test sample obtained from a subject;

comparing the level of CHI3L1 in the sample to a reference level of CHI3L1;

determining that the subject is at risk for pulmonary fibrosis when the level of CHI3L1 is increased relative to a reference level; and determining that the subject is not at risk for pulmonary fibrosis when the level of CHI3L1 is not increased relative to a reference level.

10. A method of determining the efficacy of a treatment for pulmonary fibrosis in a subject with Hermansky Pudlak Syndrome (HPS), the method comprising:
   (a) measuring the level of CHI3L1 in a test sample obtained from a subject before administration of the treatment;
   (b) measuring the level of CHI3L1 in a test sample obtained from a subject after administration of the treatment; and
   (c) determining that the treatment is not efficacious when the expression level determined in step (b) is increased relative to the expression level determined in step (a).

11. A method of treatment for pulmonary fibrosis in a subject with Hermansky Pudlak Syndrome, the method comprising;
   measuring the level of CHI3L1 in a test sample obtained from a subject;
   treating the subject with a pulmonary fibrosis treatment when the level of CHI3L1 is increased relative to a reference level; and
   not treating the subject with a pulmonary fibrosis treatment when the level of CHI3L1 is not increased relative to a reference level.

12. The assay or method of any of paragraphs 1-11, wherein the sample obtained from the subject is a blood, serum or plasma sample.

13. The assay or method of any of paragraphs 1-12, wherein a detectable signal is generated by a CHI3L1-specific reagent when a CHI3L1 molecule is present.

14. The assay or method of any of paragraphs 1-13, wherein the CHI3L1-specific reagent is detectably labeled or capable of generating a detectable signal.

15. The assay or method of any of paragraphs 1-14, wherein the treatment for pulmonary fibrosis is an agonist of IL-13Rα2 or an inhibitor of CRTH2.

16. The assay or method of paragraph 15, wherein the agonist of IL-13Rα2 is an agonist of Rab32/38.

17. The assay or method of any of paragraphs 1-16, wherein the inhibitor of CRTH2 is selected from the group consisting of:
   OC-459; AZD-1981; Setipiprant; QAW-039; QAV-680; MK-7246; ADC-3680; BI671800; ARRY-502; RG-7581; AZD-5985; AZD-8075; AM461; AM211; AMG-853; $PGD_2$; AM432; CAY-10471; TM-30089; TM-30643; TM-30642; Ramatroban; and 00000459.

18. The assay or method of any of paragraphs 1-17, wherein the level of CHI3L1 is determined by measuring the level of a nucleic acid.

19. The assay or method of any of paragraphs 1-18, wherein the level of CHI3L1 is determined by determined the level of CHI3L1 RNA transcript.

20. The assay or method of any of paragraphs 1-19, wherein the level of the nucleic acid is determined using a method selected from the group consisting of: RT-PCR; quantitative RT-PCR; Northern blot; microarray based expression analysis; next-generation sequencing; and RNA in situ hybridization.

21. The assay or method of any of paragraphs 1-17, wherein the level of CHI3L1 is determined by measuring the level of CHI3L1 polypeptide.

22. The assay or method of paragraph 21, wherein the level of the polypeptide is determined using a method selected from the group consisting of:
   Western blot; immunoprecipitation; enzyme-linked immunosorbent assay (ELISA); radioimmunological assay (RIA); sandwich assay; fluorescence in situ hybridization (FISH); immunohistological staining; radioimmunometric assay; immunofluoresence assay; mass spectroscopy; FACS; and immunoelectrophoresis assay.

23. The assay or method of any of paragraphs 1-22, wherein the polypeptide level is measured using an antibody reagent.

24. The assay or method of paragraph 23, wherein the antibody reagent is detectably labeled or generates a detectable signal.

25. The assay or method of any of paragraphs 1-24, wherein the expression level of CHI3L1 is normalized relative to the expression level of one or more reference genes or reference proteins.

26. The assay or method of any of paragraphs 1-25, wherein the reference level of CHI3L1 is the expression level of CHI3L1 in a prior sample obtained from the subject.

27. A kit for performing the method/assay of any of paragraphs 1-26.

28. A computer system for determining the risk of a subject with Hermansky Pudlak Syndrome (HPS) having or developing pulmonary fibrosis, the system comprising:
   a measuring module configured to measure the level of CHI3L1 in a test sample obtained from a subject;
   a storage module configured to store output data from the determination module;
   a comparison module adapted to compare the data stored on the storage module with a reference level, and to provide a retrieved content, and
   a display module for displaying whether the sample comprises a level of CHI3L1 which is significantly increased relative to the reference expression level and/or displaying the relative level of CHI3L1.

29. The system of paragraph 28, wherein the measuring module measures the intensity of a detectable signal from an assay indicating the level of CHI3L1 polypeptide in the test sample.

30. The system of paragraph 29, wherein the assay is an immunoassay.

31. The system of any of paragraphs 28-30, wherein the measuring module measures the intensity of a detectable signal from a RT-PCR assay indicating the level of CHI3L1 RNA transcript in the test sample.

32. The system of any of paragraphs 28-31, wherein if the computing module determines that the level of CHI3L1 in the test sample obtained from a subject is greater by a statistically significant amount than the reference level, the display module displays a signal indicating that the levels in the sample obtained from a subject are greater than those of the reference level.

33. The system of any of paragraphs 28-32, wherein the signal indicates that the subject has an increased likelihood of having or developing pulmonary fibrosis.

34. The system of any of paragraphs 28-33, wherein the signal indicates the subject is in need of treatment for pulmonary fibrosis.
35. The system of any of paragraphs 28-34, wherein the signal indicates the degree to which the level of CHI3L1 in the sample obtained from a subject varies from the reference level.

EXAMPLES

Example 1: Elevated Chitinase 3-like-1 and Differential Trafficking of IL-13Rα2 and CRTH2 Contribute to Pulmonary Injury and Fibroproliferative Repair in Hermansky-Pudlak Syndrome Hermansky-Pudlak Syndrome (HPS) comprises a group of inherited disorders caused by mutations that alter the function of lysosome-related organelles Pulmonary fibrosis is the major cause of morbidity and mortality in BLOC-3 mutant HPS-1 and HPS-4 patients. Chitinase 3-like-1 (CHI3L1), a prototypic chitinase-like protein, plays a protective role by ameliorating cell death and stimulating fibroproliferative repair. It is demonstrated herein that CHI3L1 is a biomarker that differentiates HPS patients that will develop fibrosis from those that will remain fibrosis-free, and associates with rapidly progressive disease. Using murine models it is also demonstrated that a defect in CHI3L1 inhibition of epithelial apoptosis and exaggerated CHI3L1-driven fibroproliferation play important roles in HPS fibrosis. Lastly it is demonstrated that these divergent responses are mediated by differences in the trafficking and effector functions of two CHI3L1 receptors. Specifically, the enhanced sensitivity to apoptosis is due to the BLOC-3 dependent and thus abnormal trafficking of IL-13Rα2. In contrast, the fibrosis is due to interactions of Chi3l1 and CRTH2 which traffics normally in HPS patients.

Hermansky-Pudlak Syndrome (HPS) is a group of inherited autosomal recessive disorders that occur worldwide[1]. Nine genetic subtypes (HPS1-9) have been described with each mutation affecting the function of lysosome-related organelles (LROs). HPS-1 is particularly common in northwest Puerto Rico where 1:1800 people are affected and the carrier frequency is 1 in 21 persons. The signs and symptoms of HPS are related to the dysfunction of a variety of LROs[2,3]. The dysfunction of melanosomes accounts for the oculocutaneous albinism and visual impairment found in all HPS patients[4]. The dysfunction of platelet dense granules accounts for the bleeding disorder that is often the presenting complaint of the disease[4,5]. Ceroid deposition also occurs in multiple organs, and inflammatory bowel disease has been reported in various subtypes of HPS[2,6-8]. More importantly, pulmonary fibrosis has been appreciated in HPS-1 and HPS-4 patients, whose genetic defects are in biogenesis of lysosome-related organelle complex 3 (BLOC-3), which includes HPS1 and HPS4 proteins, and, less commonly, HPS-2 patients[3,9-12]. To date, pulmonary fibrosis has not been reported in patients with BLOC-2 defects (i.e., HPS-3, HPS-5, or HPS-6). Due to the untreatable and progressive nature of the pulmonary fibrosis of HPS, this complication is the leading cause of death[13]. However, there is no way to predict in which HPS-1 or HPS-4 patients lung involvement is imminent, or which patients will progress most rapidly. In addition, although it is known that murine genetic models of HPS-1 manifest exaggerated injury and fibroproliferative repair responses to fibrogenic agents like bleomycin[14], the mechanism(s) by which LRO-related defects in trafficking lead to injury and fibrosis have not been adequately defined. Furthermore, no plausible explanation for why fibrosis develops in patients with BLOC-3 mutations and not in patients with BLOC-2 mutations has been put forth. Thus, the field would benefit greatly from the identification of a biomarker that can predict disease occurrence and rate of progression and define the mechanisms by which LRO dysfunction leads to injury and fibroproliferative repair.

The 18 glycosyl hydrolase (GH 18) gene family contains true chitinases (Cs) that degrade chitin polysaccharides and chitinase-like proteins (CLPs) which bind but do not degrade chitin[15]. GH 18 genes are members of an ancient gene family that exists in species as diverse as plants, insects and man, and whose evolution during speciation is characterized by a particularly impressive increase in CLPs coinciding with the appearance of mammals[16,17]. Retention of GH 18 genes across species and evolutionary time has led to the belief that some of these moieties play essential roles in biology. Recent studies have confirmed this speculation[15, 18-21], particularly for the prototypic CLP, chitinase 3-like-1 (CHI3L1; also called YKL-40 in man and BRP-39 in the mouse). CHI3L1 has been shown by our laboratory and others to play major roles in anti-pathogen, antigen-induced, and oxidant-induced inflammation, repair and remodeling responses by regulating a variety of essential biologic processes including oxidant injury, apoptosis, pyroptosis, inflammasome activation, Th1/Th2 inflammatory balance, M2 macrophage differentiation, TGF-β1 elaboration, dendritic cell accumulation and activation and MAPK and Akt signaling[18,20-25]. Surprisingly, the regulation of CHI3L1 and its roles in HPS and animal models of the disease have not been addressed. In addition, although recent studies have defined IL-13Rα2 as the first receptor for any GH 18 moiety and demonstrated that it mediates many of the effects of CHI3L1[27], the role(s) of CHI3L1 receptors in HPS has not been previously addressed.

The inventors hypothesized that CHI3L1 is dysregulated in HPS patients with BLOC-3 defects, and plays an important role(s) in the pathogenesis of HPS lung disease. To test this hypothesis, plasma from patients with various types of HPS were obtained, the levels of CHI3L1 were assessed and the relationships between these levels and the presence, severity and progression of lung disease were assessed. Wild type (WT) and HPS1 mutant mice were also used to characterize the roles of CHI3L1 and its receptors in the injury and fibroproliferative repair responses induced by intratracheal bleomycin.

The results presented herein demonstrate that the levels of circulating CHI3L1 are increased in patients with HPS-1 and HPS-4 when compared to controls and non-BLOC-3 HPS patients and that, in the BLOC-3 patients, these levels correlate with the presence and severity of lung disease. CHI3L1 levels are increased in HPS1 mutant mice at baseline and after bleomycin treatment, and null mutations of HPS1 cause exaggerated bleomycin-induced epithelial cell apoptosis and fibrotic responses. These murine studies also demonstrate that CHI3L1 inhibits injury and stimulates repair in WT mice. In contrast, in HPS1 mutant mice, the ability of CHI3L1 to stimulate fibroproliferation is preserved but its ability to control epithelial apoptosis is markedly diminished. Lastly, provided herein are insights into the mechanisms that underlie these seemingly opposed responses by demonstrating that they are due to differences in the trafficking and function of two different CHI3L1 receptors. Specifically, the abnormal regulation of apoptosis is due to abnormal BLOC-3- and Rab32/38-dependent plasma membrane trafficking of IL-13Rα2, and can be overcome with IL-13Rα2 overexpression. In contrast, the exaggerated collagen accumulation is mediated by CHI3L1 interaction with CRTH2 which traffics normally in HPS1 mutant cells and tissues and CRTH2 inhibition significantly diminishes this CHI3L1-induced fibrotic response.

Results

The Levels of CHI3L1 are Increased in the Circulation of HPS-1 and HPS-4 Patients.

Figure 1B:
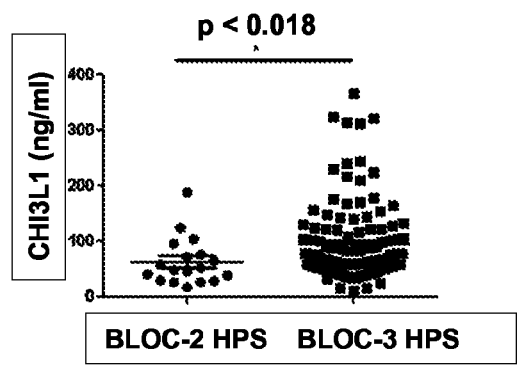

To determine if CHI3L1 is dysregulated in HPS, the levels of circulating CHI3L1 were measured in patients >18 years of age with HPS and controls who had been assessed for the presence or absence of pulmonary fibrosis. 147 plasma samples from HPS patients were obtained. Of these, 129 had BLOC-3 related HPS (125 HPS-1 and 4 HPS-4) and 18 had BLOC-2 HPS (12 HPS-3, 4 HPS-5 and 2 HPS-6). No other demographic information was available for the HPS subjects. Plasma from age-matched healthy controls were used as controls (n=38). These assays demonstrated that CHI3L1 is elevated in the circulation of HPS-1 and HPS-4 patients compared to normal controls (FIG. 1A). Moreover, the levels of CHI3L1 were elevated in the circulation of HPS-1 and HPS-4 patients compared to HPS-3, HPS-5, and HPS-6 patients (FIG. 1B). These studies demonstrate that the levels of CHI3L1 are elevated in the circulation of patients with BLOC-3 related HPS, who are more likely to develop pulmonary fibrosis, compared to normal controls and to BLOC-2 related HPS patients who will not develop pulmonary fibrosis.

The Levels of CHI3L1 are Elevated in HPS-1 and HPS-4 Patients with Pulmonary Fibrosis.

Figure 1C:
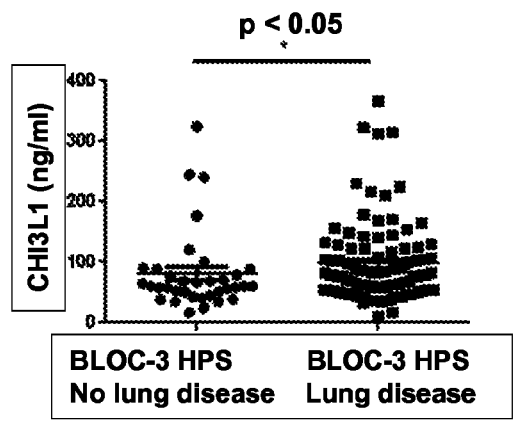

Having found that HPS-1 and HPS-4 patients had elevated circulating CHI3L1, these patients were stratified into those with and those without documented lung disease. It was found that HPS-1 and HPS-4 patients with lung disease have significantly elevated levels of circulating CHI3L1 compared to HPS-1 and HPS-4 patients without known lung disease (FIG. 1C). These results demonstrate that circulating CHI3L1 is highest in those HPS patients with BLOC-3 mutations who have pulmonary fibrosis.

The Levels of CHI3L1 Correlate with Disease Severity.

Figure 1D:
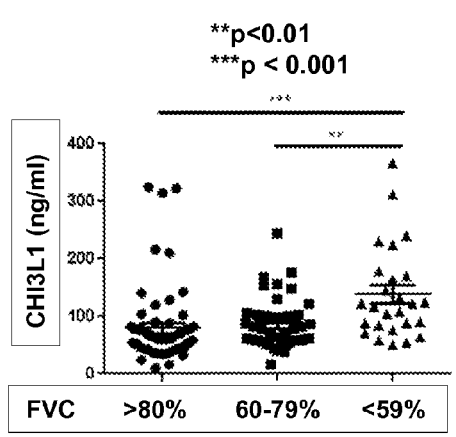
Figure 1E:
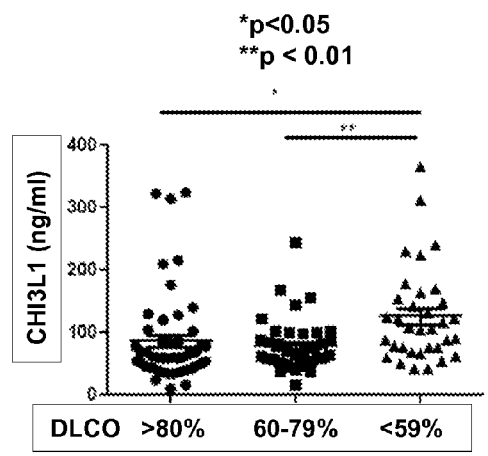
Figure 1F:
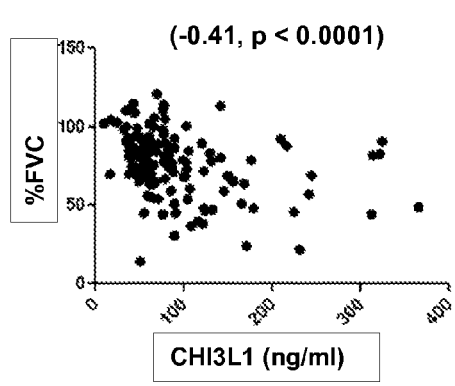
Figure 1G:
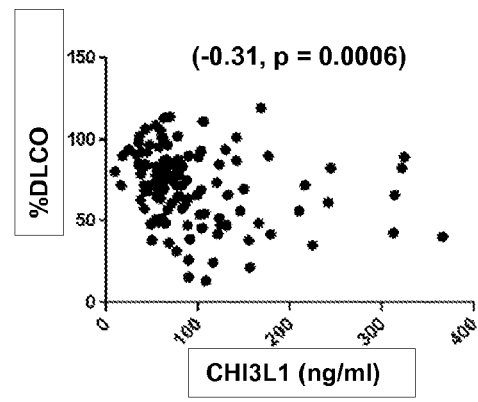

HPS-1 and HPS-4 patients with pulmonary fibrosis were next stratified into mild disease (defined as forced vital capacity (FVC)>80% predicted), mild-moderate disease (defined as FVC between 60-79% predicted) and severe disease (defined as FVC<59% predicted). It was found that the levels of circulating CHI3L1 were similar in patients with mild and moderate disease (FIG. 1D). In contrast, patients with severe disease had levels of CHI3L1 that were significantly elevated compared to mild and moderate patients (FIG. 1D). The levels of CHI3L1 also correlated with severity when assessed using the diffusing capacity (DLCO). These evaluations demonstrated that patients with severe disease had the highest levels of CHI3L1 (FIG. 1E). In accord with these findings, the levels of CHI3L1 displayed a modest but significant negative correlation with FVC (FIG. 1F) and a negative correlation with DLCO (FIG. 1G).

The Levels of CHI3L1 are Elevated in Pale Ear Mice, a Mouse Model of HPS-1.

Figure 2A:
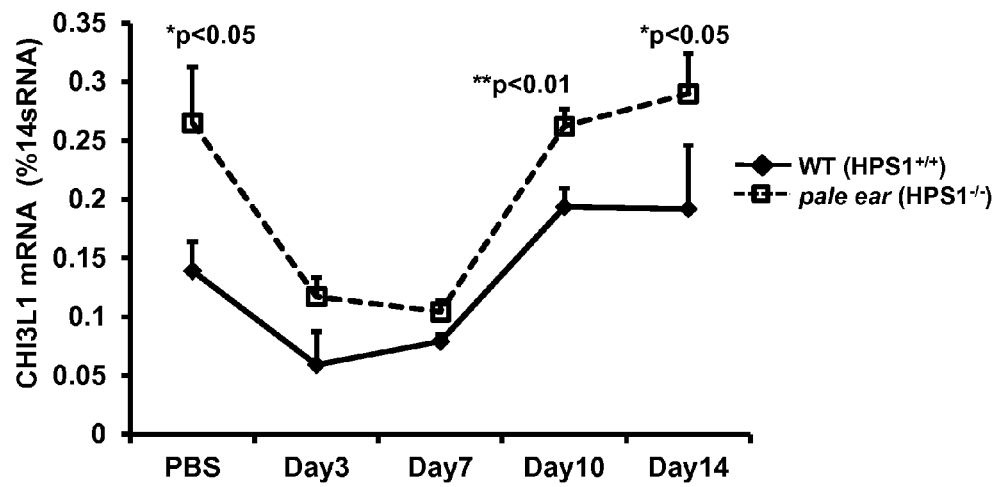
FIGS. 2A-2B demonstrate that CHI3L1 levels are increased in the lungs of pale ear mice. WT and pale ear mice ($HPS1^{-/-}$) were subjected to intratracheal saline or bleomycin administration.
Figure 2B:
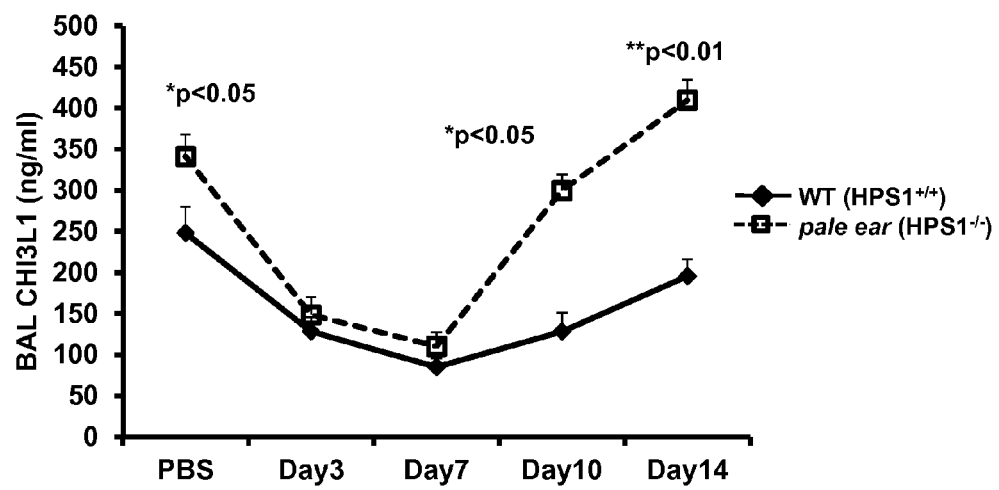

The pale ear mouse, which has a null mutation of the HPS1 gene, shares many aspects of the human disease phenotype[14,28]. To determine if CHI3L1 is dysregulated in pale ear mice, lung lysate CHI3L1 mRNA and bronchoalveolar lavage (BAL) CHI3L1 protein in wild type (WT) and pale ear mice were evaluated at baseline and after bleomycin challenge. These assessments were undertaken during the injury and fibroproliferative repair phases of the bleomycin response. At baseline, the levels of CHI3L1 were elevated in the lungs of pale ear mice compared to WT controls (FIGS. 2A and 2B). In WT mice, bleomycin administration caused early tissue injury that was associated with a significant decrease in tissue and BAL CHI3L1 (FIGS. 2A and 2B). During the fibroproliferative phase (day 5-14), the levels of CHI3L1 returned to normal (FIGS. 2A and 2B). Interestingly, the levels of tissue and BAL CHI3L1 in pale ear mice were increased at all time points (FIGS. 2A and 2B). These studies demonstrate that the expression of CHI3L1 is increased at baseline and during bleomycin-induced injury and repair in pale ear mice.

The Levels of Epithelial Apoptosis and Tissue Fibrosis are Elevated in Pale Ear Mice.

Figure 3A:
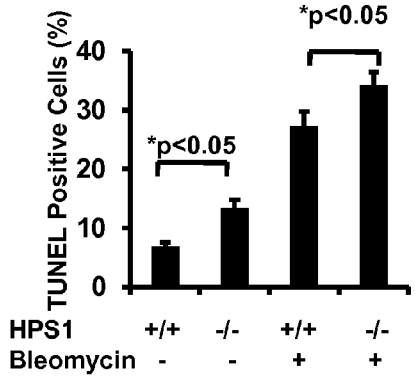
FIGS. 3A-3F demonstrate that CHI3L1 does not regulate apoptosis but does regulate fibroproliferative repair in HPS.
Figure 3B:
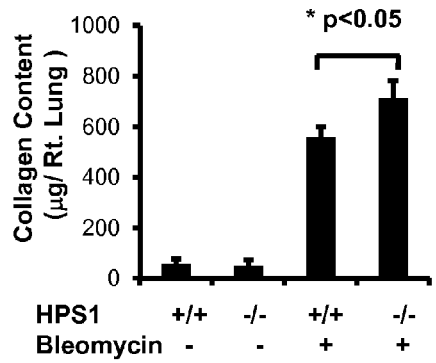
Figure 11:
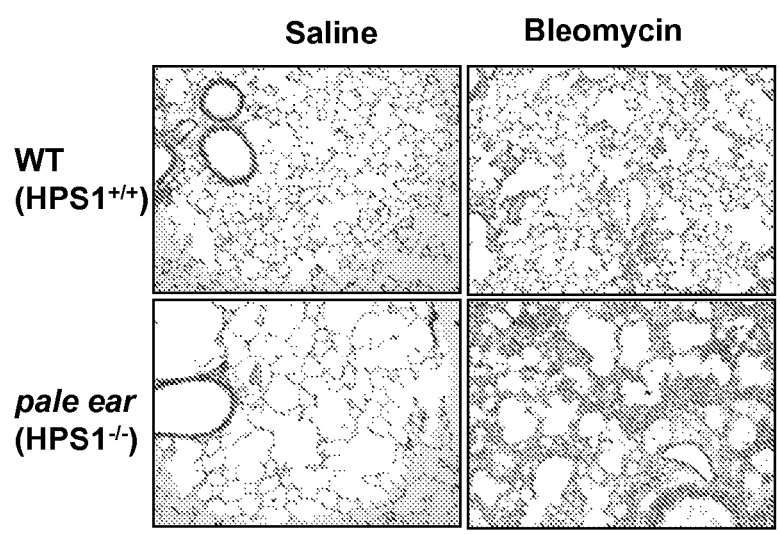
FIG. 11 demonstrates that pale ear mice develop enhanced apoptosis during injury and enhanced pulmonary fibrosis during repair. WT and pale ear mice were subjected to intratracheal bleomycin administration. H&E staining was performed on Day 14. Images are representative of a minimum of 4 mice in each group.

Studies from the inventors and others have demonstrated that injury is an obligatory prerequisite for the development of tissue fibrosis[29]. Thus, studies were undertaken to evaluate both of these responses in WT mice and pale ear mice after bleomycin administration. These studies demonstrated that, in WT mice, bleomycin caused an acute injury response characterized by alveolar type II epithelial cell apoptosis on Day 7 that was followed temporally by enhanced collagen accumulation and tissue fibrosis on Day 14 (FIGS. 3A and 3B, FIG. 11). At baseline pale ear mice had a modest but statistically significant increase in epithelial TUNEL staining (FIG. 3A and data not shown). They did not however, manifest noticeable increases in lung collagen content (FIG. 3B and FIG. 11). Importantly, both the differences in TUNEL staining and in collagen content were exaggerated in bleomycin-treated pale ear mice. Specifically, after bleomycin administration pale ear mice manifested exaggerated levels of epithelial apoptosis (FIG. 3A and data not shown). In addition, as described in the literature[14], pale ear mice also exhibited enhanced fibrotic responses compared to WT controls (FIG. 3B and FIG. 11).

Endogenous CHI3L1 does not Regulate Apoptosis but does Regulate Fibroproliferative Repair in Pale Ear Mice.

Figure 3C:
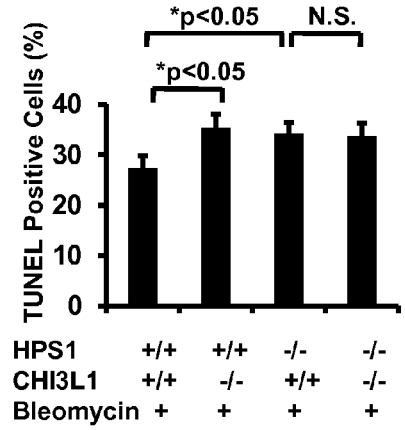
Figure 3D:
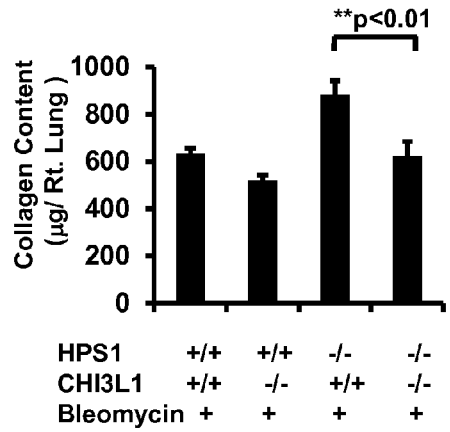
Figure 12A:
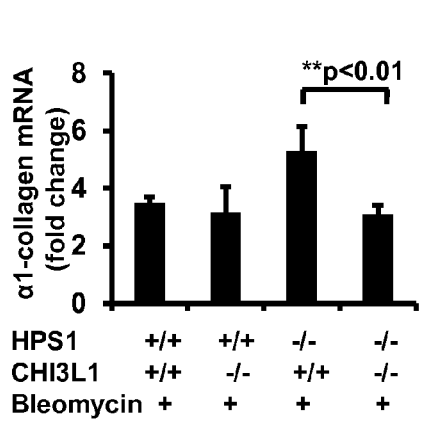
FIGS. 12A-12F demonstrate that CHI3L1 regulates fibroproliferative repair in pale ear mice. WT, CHI3L1⁻/⁻, pale ear, and HPS1⁻/⁻CHI3L1⁻/⁻ mice were subjected to intratracheal bleomycin administration. mRNA levels of (FIG. 12A) α1-procollagen (Col1-α1), (FIG. 12B) fibronectin were evaluated by qRT-PCR, and (FIG. 12C) BAL TGF-β levels were evaluated by ELISA. WT, CHI3L1 Tg, pale ear, and HPS1⁻/⁻CHI3L1 Tg mice were subjected to intratracheal bleomycin administration. mRNA levels of (FIG. 12D) α1-procollagen (Col1-α1), (FIG. 12E) fibronectin were evaluated by qRT-PCR, and (FIG. 12F) BAL TGF-β levels were evaluated by ELISA. Values are mean±SEM with a minimum of 4 mice in each group. *p≤0.05,**p≤0.01.
Figure 12D:
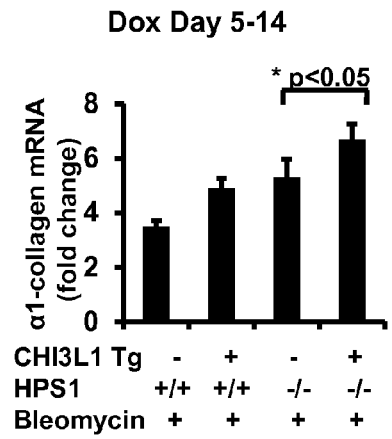
Figure 12B:
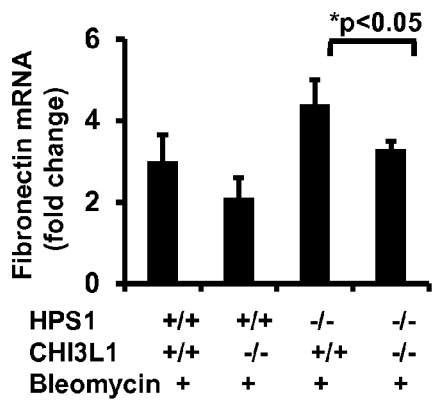
Figure 12E:
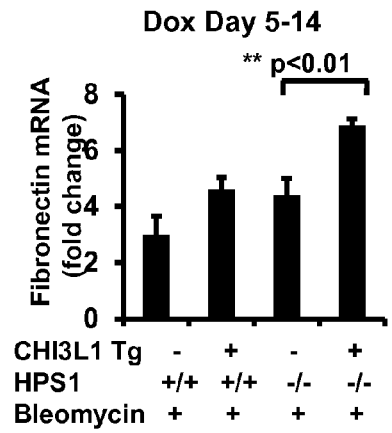
Figure 12C:
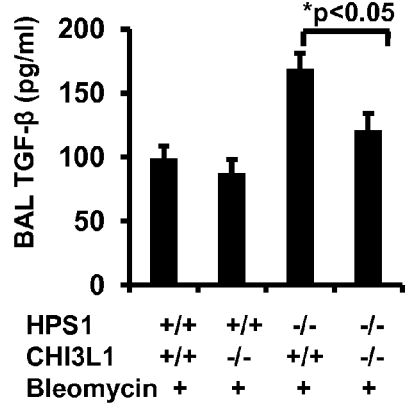

The bleomycin-induced epithelial injury (apoptosis) and fibroproliferative repair (collagen accumulation) responses were compared in WT mice, CHI3L1 null mice, pale ear mice, and pale ear/CHI3L1 double mutants. When compared to the WT controls, bleomycin-challenged CHI3L1 null mice and pale ear mice manifest exaggerated levels of apoptosis (FIG. 3C). In contrast, the levels of collagen accumulation in CHI3L1 mutant and pale ear mice were comparable to and exceeded, respectively, those of WT controls (FIG. 3D). Importantly, the exaggerated bleomycin-induced epithelial cell death response in pale ear mice was not altered by an absence of CHI3L1 (FIG. 3C). In contrast, the enhanced fibrotic response in pale ear mice was significantly diminished in the absence of CHI3L1 (FIG. 3D). In accord with these later findings, the levels of mRNA encoding α1-procollagen and fibronectin and the levels of BAL TGF-β1 were significantly decreased in pale ear/CHI3L1 double mutant mice compared to pale ear mice (FIGS. 12A-12C). These studies demonstrated that endogenous CHI3L1 regulates bleomycin-induced epithelial apoptosis and tissue fibrosis in WT mice but only regulates fibrosis in pale ear mice.

Transgenic CHI3L1 Rescues the Bleomycin-Induced Type II Epithelial Cell Apoptosis in WT but not in Pale Ear Mice.

Figure 3E:
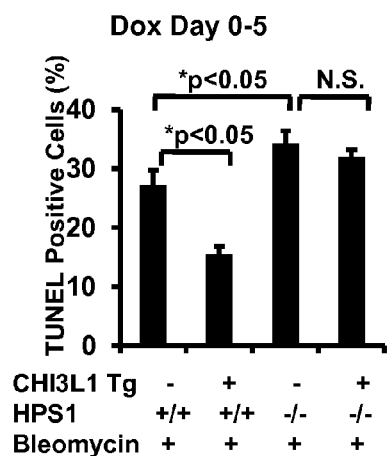

To further define the roles of CHI3L1 in the injury phase of bleomycin-induced responses, CHI3L1 transgenic (Tg) mice in which CHI3L1 was selectively and inducibly targeted to the lung using the CC10 promoter[20] were used. In these experiments CHI3L1 Tg mice were generated on WT and pale ear genetic backgrounds, the CHI3L1 Tg activated only during the tissue injury phase (Days 0-5) after bleomycin administration, and the levels of apoptosis characterized using TUNEL evaluations 7 days after bleomycin administration. As noted above, bleomycin increased the levels of apoptosis in WT mice and caused an exaggerated apoptotic response in pale ear mice (FIG. 3E). Interestingly, transgenic CHI3L1 markedly decreased the bleomycin-induced apoptosis in the WT mice (FIG. 3E). Importantly, transgenic CHI3L1 did not rescue the apoptosis phenotype in pale ear mice (FIG. 3E). This demonstrates that CHI3L1 has important anti-apoptotic effects in bleomycin treated WT mice and that this protective response is blunted in mice with null mutations of HPS1.

Transgenic CHI3L1 Exaggerates Bleomycin-Induced Fibroproliferative Repair in WT and Pale Ear Mice.

Figure 3F:
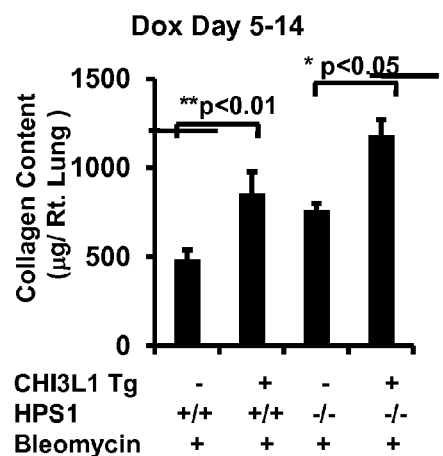
Figure 12F:
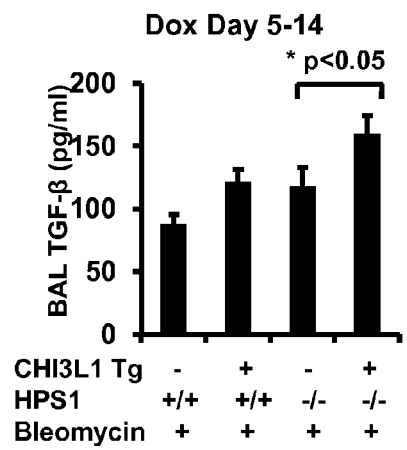

The CHI3L1 Tg mice were also used to further define the roles of CHI3L1 in bleomycin-induced fibroproliferative repair. Bleomycin was administered to WT and pale ear mice and the investigators activated the CHI3L1 transgene only during the fibroproliferative phase (days 5-14) of this response. In these experiments, transgenic CHI3L1 significantly increased the collagen accumulation in the lungs from both WT and pale ear mice (FIG. 3F). In accord with these findings the levels of mRNA encoding α1-procollagen and fibronectin, and the levels of BAL TGF-β1 (FIGS. 12D-12F) were also increased in WT and pale ear mice. These studies demonstrate that, when overexpressed only during the fibroproliferative repair phase of the bleomycin-induced response, CHI3L1 stimulates fibrosis and matrix gene expression in WT mice and mice with null mutations of HPS1.

IL-13Rα2 Membrane Trafficking is Impaired in Pale Ear Mice.

Figure 4:
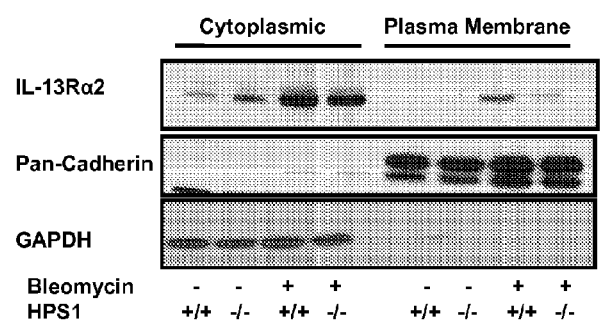
FIG. 4 demonstrates that IL-13Rα2 membrane trafficking is impaired in pale ear mice. Total protein was extracted from the cytoplasmic fraction or plasma membrane fraction of WT and pale ear mouse lung. Western blot analysis was performed to detect IL-13Rα2. Pan-Cadherin and GAPDH were used as specificity and loading controls. Values are mean±SEM with a minimum of 4 mice in each group.

The studies noted above highlight a defect in the ability of CHI3L1 to control epithelial cell apoptosis in pale ear mice. The inventors have identified that CHI3L1 binds to, signals and controls apoptosis via IL-13Rα2[27,30]. Hence, it was sought to determine if IL-13Rα2 trafficking is altered in the setting of BLOC-3 mutations and contributes to the pathogenesis of pulmonary fibrosis in pale ear mice. WT and pale ear mice were treated with bleomycin, and IL-13Rα2 immunofluorescence staining was performed using pan-cadherin or early endosome antigen (EEA) 1 markers to highlight the plasma membrane and endosomal compartments, respectively. In keeping with the literature, in WT mice at baseline, the majority of the IL-13Rα2 was intracellular, with a small fraction on the cell membrane (data not shown). In contrast, in pale ear mouse lungs the cytoplasmic pool was readily noted but the membrane pool could not be appreciated (data not shown). Importantly, bleomycin treatment caused profound IL-13Rα2 membrane translocation in the WT lung as indicated by its colocalization with cadherin (data not shown). In contrast, IL-13Rα2 remained in the endosomal compartment in bleomycin-treated pale ear mouse lungs, demonstrating that its trafficking to plasma membrane was impaired (data not shown). Western blot analysis confirmed these observations; in WT lung lysates, IL-13Raα2 could be detected in the plasma membrane fraction, while membrane translocation of IL-13Rα2 was significantly diminished in pale ear mouse lungs (FIG. 4). These results demonstrate that IL-13Rα2 exists in a cytoplasmic pool and can be mobilized to the plasma membrane after stimulation with agents like bleomycin. In addition, it demonstrates that IL-13Rα2 trafficking to the plasma membrane is dependent on a pathway that involves the BLOC-3 complex.

IL-13Rα2 Rescues the Anti-Apoptotic Effects of CHI3L1 in Primary Type II Epithelial Cells from Pale Ear Mice.

Figure 5A:
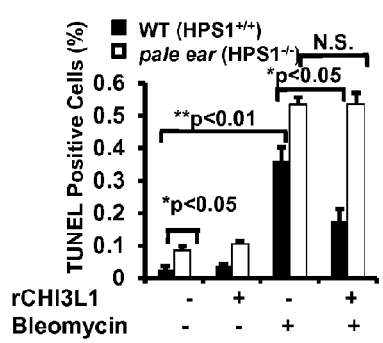
FIGS. 5A-5B demonstrate that Chi3l1 inhibits bleomycin induced cellular apoptosis in cells from wild type but not pale ear mice. Primary Type II alveolar epithelial cells were extracted from WT and pale ear mice, pre-treated with recombinant CHI3L1, transfected with empty vector or an IL-13Rα2 construct, and treated with bleomycin in vitro. TUNEL staining was performed and TUNEL-positive cells were counted.
Figure 5B:
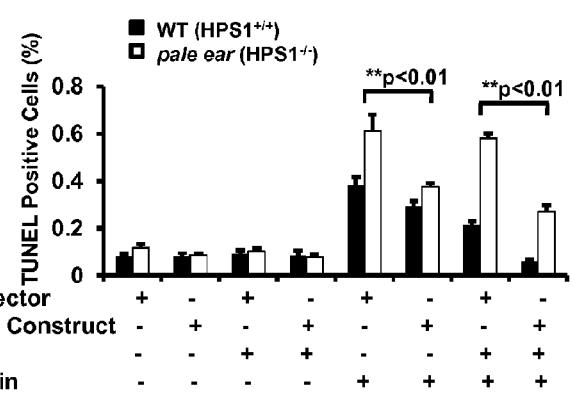

To further understand the role(s) of IL-13Rα2 in the defective CHI3L1 regulation of epithelial apoptosis in pale ear mice, alveolar type II cells were isolated from lungs of WT and pale ear mice; the trafficking of IL-13Rα2 in these cells was assessed and the ability of IL-13Rα2 to rescue the antiapoptotic effects of CHI3L1 was evaluated. Consistent with our in vivo findings, IL-13Rα2 membrane translocation was readily appreciated in cells from WT mice following bleomycin stimulation (data not shown). In contrast, IL-13Rα2 remained in the cytoplasmic fraction in bleomycin-treated pale ear cells (data not shown). Bleomycin treatment also induced epithelial apoptosis in cells from WT mice and exaggerated apoptotic responses were seen in cells from pale ear mice (FIG. 5A). Recombinant CHI3L1 was a powerful inhibitor of bleomycin-induced apoptosis in cells from WT mice (FIG. 5A). In contrast, it did not decrease the apoptosis in similarly treated cells from pale ear mice (FIG. 5A). However, transfection of cells from pale ear mice with a construct that expressed IL-13Rα2 allowed a membrane pool of IL-13Rα2 to be appreciated (data not shown) and rescued the antiapoptotic effects of rCHI3L1 (FIG. 5B). These studies demonstrate that IL-13Rα2 expression restores the membrane localization of IL-13Rα2 and the anitapoptotic effects of CHI3L1 in bleomycin treated pale ear epithelial cells.

The BLOC-3-Rab32/38 Axis Plays an Important Role in the Antiapoptotic Effects of IL-13Rα2.

Figure 5C:
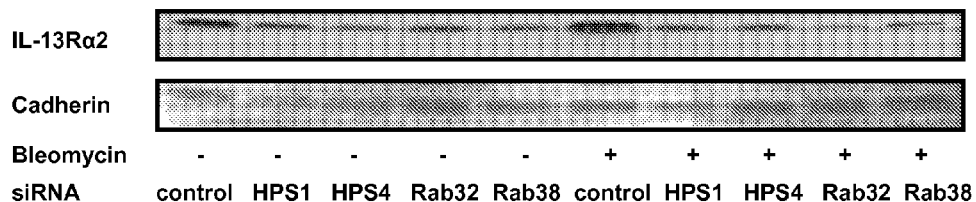
FIGS. 5C to 5E demonstrate that the BLOC-3-Rab32/38 axis plays an important role in the trafficking and antiapoptotic effects of IL-13Rα2. A549 cells were treated with HPS1, HPS4, Rab32, or Rab38 siRNA, transfected with empty vector or IL-13Rα2 construct, and treated with bleomycin in vitro.
Figure 5D:
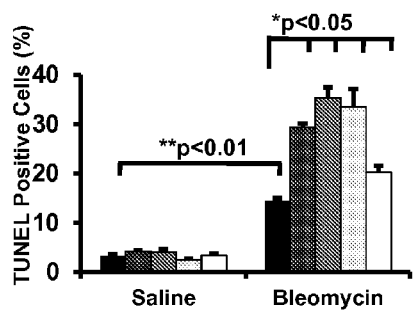
Figure 5E:
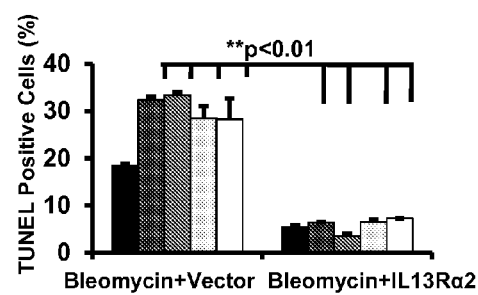
Figure 13:
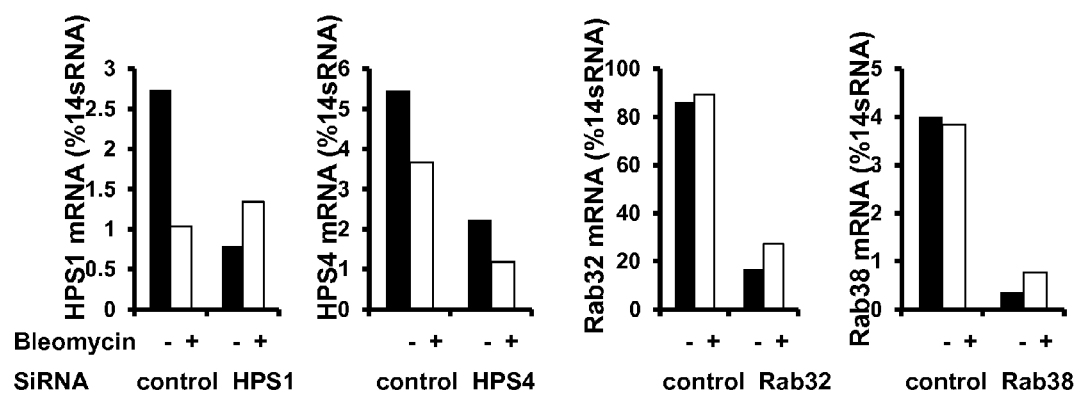
FIG. 13 depicts graphs of A549 cells treated with HPS1, HPS4, Rab32, or Rab38 siRNA. mRNA levels of HPS1, HPS4, Rab32, Rab38 were evaluated by qRT-PCR.

BLOC-3 is as a guanine nucleotide exchange factor for the Rab small GTPase family member Rab32/38[30]. As a result, HPS1 and HPS4 are required for the normal trafficking and activation of Rab32/38. The studies noted above highlight a critical role of BLOC-3 in IL-13Rα2 membrane trafficking and its anti-apoptotic response. To further understand this trafficking pathway, Type II epithelial A549 cells were treated with siRNA that specifically silenced HPS1, HPS4, Rab32, or Rab38 (FIG. 13). Bleomycin-induced IL-13Rα2 membrane trafficking was significantly diminished when the expression of any of these moieties was significantly diminished (FIG. 5C). In accord with the findings noted above, bleomycin-induced apoptotic responses were exaggerated when the expression of HPS1, HPS4, Rab32, or Rab38 were diminished (FIG. 5D) and IL-13Rα2 transfection could rescue this exaggerated apoptotic response (FIG. 5E). These studies demonstrate that BLOC-3 and its target Rab32/38 are required for IL-13Rα2 membrane trafficking and its anti-apoptotic effects.

CHI3L1 Promotes Fibroproliferation Via CRTH2.

The studies highlighted above demonstrate that CHI3L1 is induced and plays an anti-apoptotic role during the injury phase of bleomycin administration. They also demonstrate that this cytoprotective effect is mediated via IL-13Rα2 and that, in HPS1 null mice, the ability of Chi311 to exert its antiapoptotic effects are diminished due to the abnormal trafficking of IL-13Rα2. In contrast, the fibrogenic effects of CHI3L1 were intact in WT and HPS1 null mice and did not utilize IL-13Raα2 in either setting. This suggested that CHI3L1 might mediate its fibroproliferative effects via a different receptor. To address this possibility, yeast 2 hybrid evaluations were undertaken to define the binding partners of CHI3L1. This approach was the first to define IL-13Rα2 as a receptor for CHI3L1. Interestingly, in addition to IL-13Rα2, one of the most intriguing positive clones encoded the prostaglandin D2 receptor CRTH2. The ability of CHI3L1 and CRTH2 to interact with one another was then assessed using co-immunoprecipitation (Co-IP) evaluations.

Figure 6A:
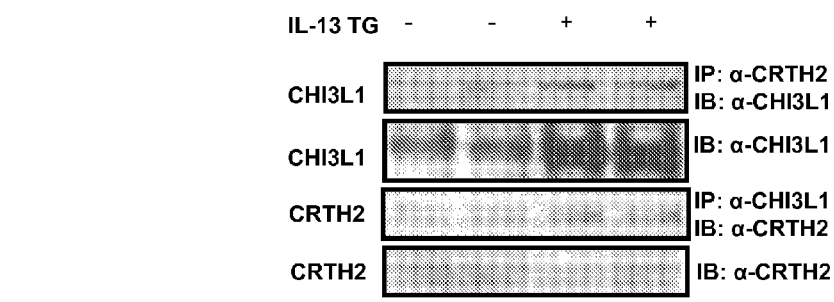
FIGS. 6A-6E demonstrate that CHI3L1 binds to and promotes fibrosis development through CRTH2.
Figure 6B:
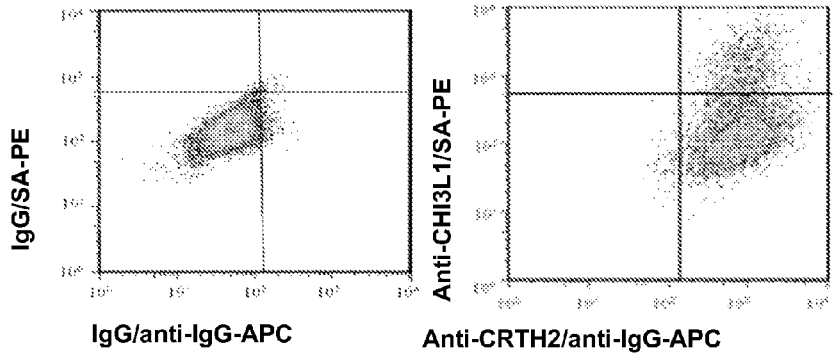
Figure 6C:
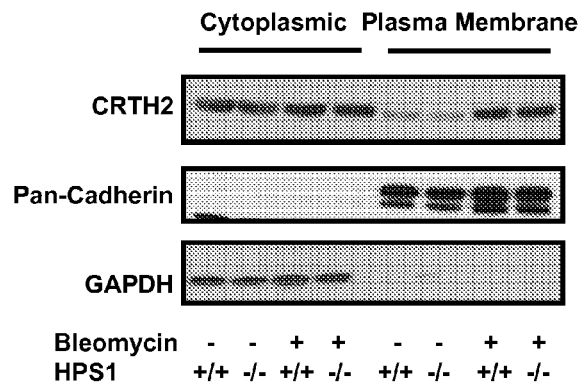
Figure 6D:
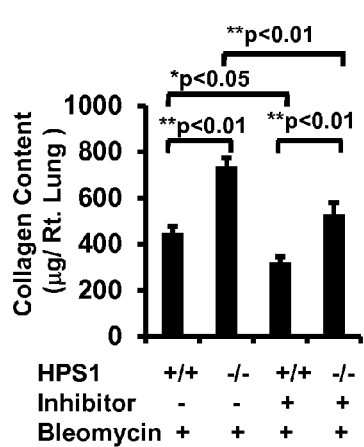
Figure 6E:
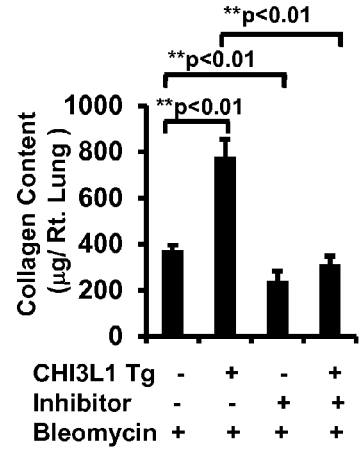

These studies demonstrated that the two moieties physically bind one another because the immunoprecipitation of one always brought down the other (FIG. 6A). Immunochemical evaluations also demonstrated that CHI3L1 and CRTH2 colocalize on the surface of the cell (FIG. 6B). Lastly, the role(s) of CRTH2 in the fibroproliferative effects of bleomycin in WT, HPS1 null and CHI3L1 Tg mice were evaluated. In these experiments, the inhibition of CRTH2 decreased to levels of bleomycin-induced collagen accumulation in WT mice, and HPS1 null mice (FIG. 6D). In addition, the exaggerated fibrosis that was caused by activation of the CHI3L1 transgene activation during fibroproliferative repair was also abrogated by CRTH2 inhibition (FIG. 6E). In accord with these findings, the trafficking of CRTH2 was similar in lungs from WT and pale ear mice following bleomycin treatment (FIG. 6C). These studies demonstrate that CRTH2 traffics normally in WT and HPS cells and tissues and plays a critical role in CHI3L1-induced fibroproliferative responses.

Discussion

HPS pulmonary fibrosis develops in the fourth or fifth decade of life and is the leading cause of death in HPS-1 and HPS-4 patients[3,9,10,13]. Despite considerable effort to understand the natural history and pathogenesis of this disorder, biomarkers that predict which HPS patients will develop pulmonary fibrosis and which patients will manifest rapidly progressive disease have not been defined. In addition, little is known about the mechanisms that drive the lung injury and the progressive fibrotic response in HPS patients, and no therapeutics successfully intervene in these responses. The data presented herein indicate that CHI3L1 is an important biomarker in HPS pulmonary fibrosis because the levels of CHI3L1 are elevated in the circulation of BLOC-3 HPS patients (who are more likely to develop pulmonary fibrosis) compared to BLOC-2 HPS patients and controls and that, in BLOC-3 patients, the levels correlate with disease severity. The present results also demonstrate that CHI3L1 plays an important role in the pathogenesis of HPS pulmonary fibrosis. Specifically, in bleomycin-treated normal mice CHI3L1 decreases epithelial injury while stimulating fibroproliferative repair. In contrast, in the pale ear mouse model of HPS-1, the ability of CHI3L1 to inhibit epithelial apoptosis is markedly blunted while the fibroproliferative effects of CHI3L1 are augmented. This demonstrates that a defect in the CHI3L1 axis is a major contributor to the exaggerated sensitivity of HPS epithelium to injury inducing and apoptotic stimuli[14,31]. Important insights are also provided into the mechanisms that underlie the defect in CHI3L1 inhibition of epithelial apoptosis and the integrity of fibroproliferative repair in HPS. These studies demonstrate that IL-13Rα2, the receptor that CHI3L1 uses to mediate its antiapoptotic effect[27,32], does not traffic properly to the cell membrane in pale ear/HPS1 null cells and tissues. They also demonstrate that overexpression of IL-13Rα2 rescues this antiapoptotic effect. Simultaneously, they demonstrate that CHI3L1 also binds to CRTH2, that CRTH2 traffics normally in cells and tissues from pale ear mice and that CHI3L1 utilizes CRTH2 to optimally promote tissue fibrotic responses.

When viewed in combination, these results demonstrate that CHI3L1 is a biomarker that differentiates HPS patients that will develop fibrosis from those that will remain fibrosis-free, and associates with rapidly progressive disease. They also demonstrate that defective CHI3L1 inhibition of epithelial apoptosis and exaggerated CHI3L1-CRTH2-driven fibroproliferation play important roles in the enhanced epithelial injury and fibrosis of HPS. Lastly, it is demonstrated that these effects are due to differential receptor trafficking and function. Specifically, IL-13Rα2 traffics to the plasma membrane via a BLOC-3-dependent mechanism and a defect in the trafficking of this receptor is an important event in the exaggerated epithelial apoptosis in BLOC-3 HPS patients. In contrast, CRTH2 traffics normally in BLOC-3 defective cells and tissues allowing the elevated levels of CHI3L1 to engender exaggerated fibroproliferative repair.

Only scant data exist regarding the simultaneous regulation of all phases of fibrogenesis in fibrotic diseases. The field is particularly lacking in the understanding of the responses that control epithelial apoptosis in the setting of oxidant and other injuries. Therefore, the discovery of a protein with the ability to exert compartment-specific effects upon different components of the fibrotic response is quite exciting. Without wishing to be limited by theory, the data presented herein suggest that CHI3L1 is just such a moiety, with distinct roles in injury and repair. Specifically, CHI3L1 has protective effects that can be mediated by its ability to decrease epithelial apoptosis, inhibit inflammation and decrease oxidant injury[36]. CHI3L1 can also drive fibroproliferative repair by augmenting alternative macrophage activation, fibroblast proliferation and extracellular matrix gene expression during the repair response. As noted above and in studies from other groups, HPS mouse models do not spontaneously develop fibrosis[37]. However, they consistently manifest exaggerated sensitivity to fibrogenic, injurious and apoptotic stimuli and these exaggerated injury responses are believed to lead to the pulmonary fibrosis that follows[14,28,31,37-42]. The present studies add to this body of data by demonstrating, for the first time, that the CHI3L1 axis plays an essential role in the regulation of epithelial apoptosis and that this response is blunted in pale ear mice. Hence, interventions that augment CHI3L1 can be therapeutically useful in controlling the injury phase of a variety of pulmonary disorders.

IL-13Rα2 was described as a high-affinity receptor for IL-13 that is distinct from the IL-13Rα1-IL-4Rα receptor dimer that IL-13 shares with IL-4[43,44]. It was initially believed to be a decoy receptor[45]. However, other studies demonstrated that IL-13 signals and regulates a variety of cellular and tissue responses via IL-13Rα2[44,46-52]. Recent studies by the inventors identified the first receptor for any GH 18 moiety by demonstrating that IL-13Rα2 binds to and is activated by CHI3L1[27,53]. These studies also showed that CHI3L1 mediates its antiapoptotic effects via this ligand-receptor interaction[27,53]. Importantly, the majority of IL-13Rα2 exists in an intracellular cytoplasmic pool and traffics to the plasma membrane after appropriate cellular activation[53-55]. However, the mechanism(s) of IL-13Rα2 mobilization to the plasma membrane has not been defined. The current studies demonstrate that IL-13Rα2 trafficking to the cell surface is mediated by a BLOC-3 complex-dependent pathway. In fact, insufficient IL-13Rα2 membrane localization is responsible for the enhanced apoptotic response in pale ear mice and overexpression of IL-13Rα2 rescues the anti-apoptotic effects of CHI3L1 in pale ear cells. These studies define, for the first time, the important role that abnormalities in IL-13Rα2 trafficking play in HPS. The data presented herein indicate that interventions that increase IL-13Rα2 membrane localization can be beneficial in the treatment of BLOC-3 HPS patients.

The genes mutated in HPS encode subunits of the BLOCs. Until recently, the molecular functions of the HPS1-HPS4 complex, BLOC-3, remained mysterious. It is now known that BLOC-3 is a Rab32 and Rab38 guanine nucleotide exchange factor (GEF) and is required for melanosome cargo delivery and pigmentation[30], melanosome biogenesis[12,30] and the trafficking of melanin-producing enzymes in melanocytes[30,58]. In the present studies it is demonstrated, for the first time, that Rab 32/38 also play critical roles in IL-13Rα2 trafficking and that loss of BLOC-3-mediated Rab32/38 activity can explain the Type II lung epithelial cell dysfunction and apoptosis seen in pale ear mice. Without wishing to be bound by theory, interventions that augment Rab32/38 can improve IL-13Raα2 trafficking and prove therapeutically useful in BLOC-3 HPS patients.

Overall, these studies indicate that interventions that increase IL-13Rα2 membrane localization and block CRTH2 function, alone or in combination, can be used to treat BLOC-3 HPS patients.

In summary, the present studies demonstrate that BLOC-3 HPS is associated with higher levels of CHI3L1 and suggest that CHI3L1 is likely produced as a protective response based on its ability to simultaneously decrease epithelial cell apoptosis and stimulate fibroproliferative repair in normal individuals. However, in HPS, the ability of CHI3L1 to inhibit epithelial cell apoptosis is impaired due, at least in part, to faulty trafficking and insufficient membrane expression of the CHI3L1 receptor IL-13Rα2. On the other hand, the sustained and enhanced production of CHI3L1 interacts with CRTH2, which traffics normally, and causes an exaggerated fibroproliferative repair response and fibrotic excess in BLOC HPS patients.

Materials and Methods

Patient Characteristics.

One hundred and forty seven samples were obtained from molecularly confirmed HPS patients ≥18 years of age with or without known lung disease that were enrolled in a clinical protocol approved by the NHGRI Institutional Review Board. All patients gave written, informed consent. Of the 147 patients, 129 had BLOC-3 related HPS (125 HPS-1 and 4 HPS-4) and 18 had BLOC-2 related disease (12 HPS-3, 4 HPS-5 and 2 HPS-6). The mean age of BLOC-3 related patients was 37.7±0.9 years while the mean age of the BLOC-3 unrelated patients was 36.3±2.9 (p=0.46). The mean FVC in the BLOC-3 related subject was 76.7±1.0 vs 94.0±2.6 (p=0.0002). The mean DLCO in the BLOC-3 related subjects was 72.0±2.0 vs 103.6±3.5 (p<0.0001).

ELISA.

Human CHI3L1 was assayed using a commercially available ELISA kit (Quidel) as previously described[61]. CHI3L1 levels in mouse BAL samples were quantified using coating and detection antibodies from MedImmune. TGF-β1 levels in mouse BAL samples were quantified using an ELISA kit (R&D Systems) following the manufacturer's instructions.

Knockout and Transgenic (Tg) Mice.

Pale ear mice were obtained from Jackson Laboratory (HPS1$^{-/-}$). CHI3L1/BRP-39 Knockout mice (CHI3L1$^{-/-}$) and CC-10 driven, lung-specific, inducible CHI3L1/YKL-40 Tg mice (CHI3L1Tg) were previously generated in our laboratory[20]. CHI3L1Tg mice or their wild-type littermate controls (transgene negative) were given doxycycline (1 g/L) in their drinking water for up to 2 weeks. All mice were congenic on a C57BL/6 background and were genotyped as previously described Animal experiments were approved by the Yale School of Medicine and Brown University Institutional Animal Care and Use Committees in accordance with federal guidelines.

Bleomycin Administration.

Sex-matched, 8-wk-old wild-type (WT), pale ear, CHI3L1$^{-/-}$, and CHI3L1Tgmice (≥5 mice/group) were exposed to a single bleomycin injection (1.25 U/kg; Teva Parenteral Medicines, Irvine, Calif.) via intratracheal administration. Mice were sacrificed and evaluated at Day 7 and Day 14 to examine apoptosis and fibrosis, respectively.

mRNA Analysis.

Total cellular RNA was obtained using TRIzol reagent (Invitrogen), according to the manufacturer's instructions. mRNA was measured using real-time RT-PCR as described previously[20,21]. The primer sequences for extracellular matrix genes were obtained from PrimerBank (pga.mgh.harvard.edu/primerbank/) or the same as previously used[20,62,63].

Histologic Analysis.

Mouse lungs were removed en bloc, inflated to 25 cm pressure with PBS containing 0.5% low melting point agarose gel, fixed, embedded in paraffin, sectioned, and stained. Hematoxylin and eosin, and Mallory's trichrome stains were performed in the Research Histology Laboratory of the Department of Pathology at the Yale University School of Medicine. BAL and lung inflammation was assessed as described previously[20].

Quantification of Lung Collagen.

Animals were anesthetized, median sternotomy was performed, and right heart perfusion completed with calcium and magnesium-free PBS. The heart and lungs were then removed. The right lung was frozen in liquid nitrogen and stored at −80° C. until used. Collagen content was determined by quantifying total soluble collagen using the Sircol Collagen Assay kit (Biocolor, Accurate Chemical & Scientific Co., Westbury, N.Y.) according to the manufacturer's instructions.

TUNEL Analysis.

End labeling of exposed 3'-OH ends of DNA fragments in paraffin-embedded tissue was undertaken with the TUNEL in situ cell death detection kit AP (Roche Diagnostics). SPC co-staining was performed using a goat anti-mouse SPC primary antibody (Santa Cruz) and Alexa Fluor 594 secondary antibody. After staining, 8-10 random pictures were obtained from each lung, and a minimum of 300 cells were visually evaluated in each section. The labeled cells were expressed as a percentage of total nuclei.

Immunofluorescence Staining.

To localize the expression of IL-13Rα2, double-label immunofluorescence staining was undertaken using Paraffin-embedded lungs from WT and pale ear mice. Monoclonal anti-IL-13Rα2 (R&D), anti-CRTH2 (Santa Cruz), antibodies against Pan-Canherin (Abcam), and EEA1 (Cell Signaling), were used in these evaluations.

Type II Epithelial Cell and A549 Cell Culture.

WT and pale ear mouse lungs were digested with collagenase and DNase I. The resulting suspension was filtered through Falcon cell strainers, and the cells were negatively selected with anti-CD16/CD32 antibodies. Cells were maintained in BEGM+5% charcoal-stripped FBS and 10 ng/ml KGF. A549 cells were obtained from the American Type Culture Collection (ATCC, Manassas, Va.) and maintained in DMEM+2 mM glutamine+10% FBS. Primary Type II Cells were pre-treated with 500 ng/ml recombinant CHI3L1, transfected with IL-13Rα2 construct, and stimulated with 100 μg/ml bleomycin. In A549 cells, HPS1, HPS4, Rab32, and Rab38 siRNA were co-transfected with IL-13Rα2 construct, and stimulated with 100 μg/ml bleomycin. Cells were cytospun onto slides. Immunofluorescence and/or TUNEL staining were performed as previously described.

Western Blot Analysis.

Lung and cell lysates were fractioned using Plasma Membrane Protein Extraction Kit (Abcam) and Western blot analysis was completed with antibodies that react selectively with IL-13Rα2 (R&D), Pan-Canherin(Abcam), GAPDH (Cell Signaling) as described previously[29].

Co-Immunoprecipitation.

Proteins from the lung lysate of WT mice or IL-13 Tg mice were clarified by centrifugation for 10 min at 4° C. CHI3L1 and CRTH2 were immunoprecipitated with anti-CHI3L1 rabbit polyclonal antibody (MedImmune) or anti-CRTH2 monoclonal antibody (Santa Cruz), respectively, using Catch and Release V2.0 (Reversible Immunoprecipitation System, EMD Millipore). The precipitates were subjected to immunoblotting with antibodies against CRTH2 or CHI3L1, respectively.

FACS Analysis.

THP-1 cells were incubated in the presence or absence of anti-CHI3L1-biotin antibody and anti-CRTH2 immunoglobulin G (IgG) antibody without permeabilization. Cells were then washed and stained with streptavidin (SA)-PE and anti-igG-APC and subjected to flow cytometric analysis.

CRTH2 Inhibition.

Sex-matched, 8-wk-old wild-type (WT), pale ear, and CHI3L1 Tg mice (≥5 mice/group) were exposed to a single bleomycin injection (1.25 U/kg; Teva Parenteral Medicines, Irvine, Calif.) via intratracheal administration. Mice were treated with 30 mg/kg CAY10471 (Cayman Chemical) (IP, every other day) or DMSO control from Day 5 to Day 14.

Statistics.

Human data are presented as dot plots with means±SEM unless stated otherwise. Normal distribution was verified with the D'Agostino and Pearson Omnibus test. Normally distributed data were compared using Student's t test or ANOVA with Bonferroni's post test as appropriate. Correlations between pulmonary function and plasma YKL-40 concentrations were performed for those subjects on whom clinical data were available using Spearman correlations. Non-normally distributed data in two groups were compared using the nonparametric two-tailed Mann-Whitney test. GraphPad Prism 5.0 (GraphPad Software, La Jolla, Calif.) and SPSS 13.0 (SPSS Inc, Chicago, Ill.) were used for the analysis. Mouse data are expressed as mean±SEM. As appropriate, groups were compared by ANOVA; follow-up comparisons between groups were conducted using a two-tailed Student t test. A p value of ≤0.05 was considered to be significant.

REFERENCES

1. Gahl, W. & Huizing, M. Hermansky-Pudlak Syndrome (October 2012) in: GeneReviews at GeneTests: Medical Genetics Information Resource. [database online]. (Original 2002; Updated 2004, March 2007, September 2012). Copyright, University of Washington, Seattle, 1997-2010. Available at on the world wide web at www.genetests.org. (2012).
2. Schinella, R. A., Greco, M. A., Cobert, B. L., Denmark, L. W. & Cox, R. P. Hermansky-Pudlak syndrome with granulomatous colitis. *Ann Intern Med* 92, 20-23 (1980).
3. Anderson, P. D., Huizing, M., Claassen, D. A., White, J. & Gahl, W. A. Hermansky-Pudlak syndrome type 4 (HPS-4): clinical and molecular characteristics. *Hum Genet* 113, 10-17 (2003).
4. Gahl, W. A., et al. Genetic defects and clinical characteristics of patients with a form of oculocutaneous albinism (Hermansky-Pudlak syndrome). *N Engl J Med* 338, 1258-1264 (1998).
5. Hermansky, F. & Pudlak, P. Albinism associated with hemorrhagic diathesis and unusual pigmented reticular cells in the bone marrow: report of two cases with histochemical studies. *Blood* 14, 162-169 (1959).
6. Tsilou, E. T., et al. Milder ocular findings in Hermansky-Pudlak syndrome type 3 compared with Hermansky-Pudlak syndrome type 1. *Ophthalmology* 111, 1599-1603 (2004).
7. Parker, M. S., et al. The Hermansky-Pudlak syndrome. *Ann Diagn Pathol* 1, 99-103 (1997).
8. Mahadeo, R., Markowitz, J., Fisher, S. & Daum, F. Hermansky-Pudlak syndrome with granulomatous colitis in children. *J Pediatr* 118, 904-906 (1991).
9. Li, W., et al. Murine Hermansky-Pudlak syndrome genes: regulators of lysosome-related organelles. *Bioessays* 26, 616-628 (2004).
10. Brantly, M., et al. Pulmonary function and high-resolution CT findings in patients with an inherited form of pulmonary fibrosis, Hermansky-Pudlak syndrome, due to mutations in HPS-1. *Chest* 117, 129-136 (2000).
11. Chiang, P. W., et al. The Hermansky-Pudlak syndrome 1 (HPS1) and HPS4 proteins are components of two complexes, BLOC-3 and BLOC-4, involved in the biogenesis of lysosome-related organelles. *J Biol Chem* 278, 20332-20337 (2003).
12. Carmona-Rivera, C., Simeonov, D. R., Cardillo, N. D., Gahl, W. A. & Cadilla, C. L. A divalent interaction between HPS1 and HPS4 is required for the formation of the biogenesis of lysosome-related organelle complex-3 (BLOC-3). *Biochimica et biophysica acta* 1833, 468-478 (2013).
13. Pierson, D. M., et al. Pulmonary fibrosis in hermansky-pudlak syndrome. a case report and review. *Respiration* 73, 382-395 (2006).
14. Young, L. R., Pasula, R., Gulleman, P. M., Deutsch, G. H. & McCormack, F. X. Susceptibility of Hermansky-Pudlak mice to bleomycin-induced type II cell apoptosis and fibrosis. *Am J Respir Cell Mol Biol* 37, 67-74 (2007).
15. Lee, C. G., et al. Role of chitin and chitinase/chitinase-like proteins in inflammation, tissue remodeling, and injury. *Annu Rev Physiol* 73, 479-501 (2011).
16. Aerts, J. M., et al. Biomarkers for lysosomal storage disorders: identification and application as exemplified by chitotriosidase in Gaucher disease. *Acta Paediatr Suppl* 97, 7-14 (2008).
17. Funkhouser, J. D. & Aronson, N. N., Jr. Chitinase family GH18: evolutionary insights from the genomic history of a diverse protein family. *BMC Evol Biol* 7, 96 (2007).
18. Dela Cruz, C. S., et al. Chitinase 3-like-1 promotes Streptococcus pneumoniae killing and augments host tolerance to lung antibacterial responses. *Cell host & microbe* 12, 34-46 (2012).
19. Lee, C. G. & Elias, J. A. Role of breast regression protein-39/YKL-40 in asthma and allergic responses. *Allergy Asthma Immunol Res* 2, 20-27 (2010).
20. Lee, C. G., et al. Role of breast regression protein 39 (BRP-39)/chitinase 3-like-1 in Th2 and IL-13-induced tissue responses and apoptosis. *J Exp Med* 206, 1149-1166 (2009).
21. Sohn, M. H., et al. The chitinase-like proteins breast regression protein-39 and YKL-40 regulate hyperoxia-induced acute lung injury. *Am J Respir Crit Care Med* 182, 918-928 (2010).
22. Areshkov, P. O., Avdieiev, S. S., Balynska, O. V., Leroith, D. & Kaysan, V. M. Two closely related human members of chitinase-like family, CHI3L1 and CHI3L2, activate ERK1/2 in 293 and U373 cells but have the different influence on cell proliferation. *Int J Biol Sci* 8, 39-48 (2012).

23. Chen, C.-C., Llado, V., Eurich, K., Tran, H. T. & Mizoguchi, E. Carbohydrate-binding motif in chitinase 3-like 1 (CH13L1/YKL-40) specifically activates Akt signaling pathway in colonic epithelial cells. *Clin. Immunol.* 140, 268-275 (2011).

24. Kim, M. N., et al. Involvement of the MAPK and PI3K pathways in chitinase 3-like 1-regulated hyperoxia-induced airway epithelial cell death. *Biochem Biophys Res Commun* 421, 790-796 (2012).

25. Matsuura, H., et al. Role of Breast Regression Protein (BRP)-39 in the Pathogenesis of Cigarette Smoke-Induced Inflammation and Emphysema. *Am J Respir Cell Mol Biol* (2011).

26. Coffman, F. D. Chitinase 3-Like-1 (CHI3L1): a putative disease marker at the interface of proteomics and glycomics. *Crit Rev Clin Lab Sci* 45, 531-562 (2008).

27. He, C. H., et al. Chitinase 3-like 1 Regulates Cellular and Tissue Responses via IL-13 Receptor alpha2. *Cell Rep* 4, 830-841 (2013).

28. Young, L. R., Borchers, M. T., Allen, H. L., Gibbons, R. S. & McCormack, F. X. Lung-restricted macrophage activation in the pearl mouse model of Hermansky-Pudlak syndrome. *J Immunol* 176, 4361-4368 (2006).

29. Lee, C. G., et al. Early growth response gene 1-mediated apoptosis is essential for transforming growth factor beta1-induced pulmonary fibrosis. *J Exp Med* 200, 377-389 (2004).

30. Gerondopoulos, A., Langemeyer, L., Liang, J. R., Linford, A. & Ban, F. A. BLOC-3 mutated in Hermansky-Pudlak syndrome is a Rab32/38 guanine nucleotide exchange factor. *Current biology: CB* 22, 2135-2139 (2012).

31. Young, L. R., et al. The alveolar epithelium determines susceptibility to lung fibrosis in Hermansky-Pudlak syndrome. *Am J Respir Crit Care Med* 186, 1014-1024 (2012).

32. Avila, N. A., et al. Hermansky-Pudlak syndrome: radiography and CT of the chest compared with pulmonary function tests and genetic studies. *AJR Am J Roentgenol* 179, 887-892 (2002).

33. Thannickal, V. J., Toews, G. B., White, E. S., Lynch, J. P., 3rd & Martinez, F. J. Mechanisms of pulmonary fibrosis. *Annu Rev Med* 55, 395-417 (2004).

34. Panos, R. J., Mortenson, R. L., Niccoli, S. A. & King, T. E., Jr. Clinical deterioration in patients with idiopathic pulmonary fibrosis: causes and assessment. *Am J Med* 88, 396-404 (1990).

35. Sime, P. J. & O'Reilly, K. M. Fibrosis of the lung and other tissues: new concepts in pathogenesis and treatment. *Clin Immunol* 99, 308-319 (2001).

36. Sohn, M. H., et al. The chitinase-like proteins breast regression protein-39 and YKL-40 regulate hyperoxia-induced acute lung injury. *Am J Respir Crit Care Med* 182, 918-928.

37. Swank, R. T., Novak, E. K., McGarry, M. P., Rusiniak, M. E. & Feng, L. Mouse models of Hermansky Pudlak syndrome: a review. *Pigment Cell Res* 11, 60-80 (1998).

38. Feng, L., Rigatti, B. W., Novak, E. K., Gorin, M. B. & Swank, R. T. Genomic structure of the mouse Ap3b1 gene in normal and pearl mice. *Genomics* 69, 370-379 (2000).

39. Mahavadi, P., et al. Epithelial stress and apoptosis underlie Hermansky-Pudlak syndrome-associated interstitial pneumonia. *Am J Respir Crit Care Med* 182, 207-219.

40. Yoshioka, Y., et al. Inflammatory response and cathepsins in silica-exposed Hermansky-Pudlak syndrome model pale ear mice. *Pathol Int* 54, 322-331 (2004).

41. Rouhani, F. N., et al. Alveolar macrophage dysregulation in Hermansky-Pudlak syndrome type 1. *Am J Respir Crit Care Med* 180, 1114-1121 (2009).

42. Atochina-Vasserman, E. N., et al. Early alveolar epithelial dysfunction promotes lung inflammation in a mouse model of Hermansky-Pudlak syndrome. *Am J Respir Crit Care Med* 184, 449-458 (2011).

43. Lupardus, P. J., Birnbaum, M. E. & Garcia, K. C. Molecular basis for shared cytokine recognition revealed in the structure of an unusually high affinity complex between IL-13 and IL-13Ralpha2. *Structure* 18, 332-342 (2010).

44. Strober, W., Kitani, A., Fichtner-Feigl, S. & Fuss, I. J. The signaling function of the IL-13Ralpha2 receptor in the development of gastrointestinal fibrosis and cancer surveillance. *Curr. Mol. Med.* 9, 740-750 (2009).

45. Konstantinidis, A. K., et al. Cellular localization of interleukin 13 receptor alpha2 in human primary bronchial epithelial cells and fibroblasts. *J. Investig. Allergol. Clin. Immunol.* 18, 174-180 (2008).

46. Daines, M. O., et al. Level of expression of IL-13Ralpha2 impacts receptor distribution and IL-13 signaling. *J. Immunol.* 176, 7495-7501 (2006).

47. Fichtner-Feigl, S., et al. Induction of IL-13 triggers TGF-beta1-dependent tissue fibrosis in chronic 2,4,6-trinitrobenzene sulfonic acid colitis. *J. Immunol.* 178, 5859-5870 (2007).

48. Fichtner-Feigl, S., Strober, S., Kawakami, K., Puri, R. K. & Kitani, A. IL-13 signaling through the IL-13alpha(2) receptor is involved in induction of TGF-beta(1) production and fibrosis. *Nat. Med.* 12, 99-106 (2006).

49. Fichtner-Feigl, S., Strober, W., Geissler, E. K. & Schlitt, H.-J. Cytokines mediating the induction of chronic colitis and colitis-associated fibrosis. *Mucosal Immunol.* 1 (Suppl 1), S24-S27 (2008).

50. Fichtner-Feigl, S., et al. Restoration of tumor immunosurveillance via targeting of interleukin-13 receptor-alpha 2. *Cancer Res.* 68, 3467-3475 (2008).

51. Yang, J. S., Allahverdian, S., Singhera, G. K., MacRedmond, R. E. & Dorscheid, D. R. IL-13Ralpha2/AP-1 complex signalling mediates airway epithelial repair without effects on remodeling pathways. *Allergy Asthma Clin Immunol.* 6, P27-P28 (2010).

52. Yang, J. S. Y., Wadsworth, S. J., Singhera, G. K. & Dorscheid, D. The regulation of IL-13ralpha1 and IL-13ralpha2 expression and distribution in airway epithelial repair. *Am. J. Respir. Crit. Care Med.* 183, A2812 (2011).

53. Daines, M. O. & Hershey, G. K. A novel mechanism by which interferon-gamma can regulate interleukin (IL)-13 responses. Evidence for intracellular stores of IL-13 receptor alpha-2 and their rapid mobilization by interferon-gamma. *The Journal of biological chemistry* 277, 10387-10393 (2002).

54. Daines, M. O., et al. Level of expression of IL-13R alpha 2 impacts receptor distribution and IL-13 signaling. *Journal of immunology* 176, 7495-7501 (2006).

55. Tabata, Y., et al. Allergy-driven alternative splicing of IL-13 receptor alpha2 yields distinct membrane and soluble forms. *Journal of immunology* 177, 7905-7912 (2006).

56. Chiaramonte, M. G., et al. Regulation and function of the interleukin 13 receptor alpha 2 during a T helper cell type 2-dominant immune response. *J Exp Med* 197, 687-701 (2003).

57. Wilson, M. S., et al. IL-13Ralpha2 and IL-10 coordinately suppress airway inflammation, airway-hyperreactivity, and fibrosis in mice. *J Clin Invest* 117, 2941-2951 (2007).
58. Wasmeier, C., et al. Rab38 and Rab32 control post-Golgi trafficking of melanogenic enzymes. *The Journal of cell biology* 175, 271-281 (2006).
59. DeFronzo, R. A., Gunnarsson, R., Bjorkman, O., Olsson, M. & Wahren, J. Effects of insulin on peripheral and splanchnic glucose metabolism in noninsulin-dependent (type II) diabetes mellitus. *J Clin Invest* 76, 149-155 (1985).
60. Marchesini, G., et al. Association of nonalcoholic fatty liver disease with insulin resistance. *The American journal of medicine* 107, 450-455 (1999).
61. Chupp, G. L., et al. A chitinase-like protein in the lung and circulation of patients with severe asthma. *N Engl J Med* 357, 2016-2027 (2007).
62. Zhou, Y., et al. Amphiregulin, an Epidermal Growth Factor Receptor Ligand, Plays an Essential Role in the Pathogenesis of Transforming Growth Factor-beta-induced Pulmonary Fibrosis. *The Journal of biological chemistry* 287, 41991-42000 (2012).
63. Kang, H. R., Lee, C. G., Homer, R. J. & Elias, J. A. Semaphorin 7A plays a critical role in TGF-beta1-induced pulmonary fibrosis. *The Journal of experimental medicine* 204, 1083-1093 (2007).

Example 2: Effects of Lentivirus IL-13Rα2 on Bleomycin-Induced Pulmonary Fibrosis in Wild Type and HPS-1 Null Mice Wild type (WT) and HPS-1 null mice were treated with bleomycin. Some mice received Lentivirus without an insert (negative). Others received Lentivirus expressing IL-13Receptor alpha2 (IL-13Ra2) as noted. Collagen content was assessed 14 days after bleomycin administration. For each bar N=2 that were within 10% of each other. Collagen content was reduced in both wildtype and HPS-1 null mice treated with the lentivirus expressing IL-12Ra2, with a greater effect observed in the HPS-1 null mice.

What is claimed herein is:

1. A method of treating Hermansky Pudlak Syndrome (HPS) in a subject in need thereof, the method comprising administering an agonist of Rab32/38 or an inhibitor of CRTH2 to the subject.

2. A method of treating pulmonary fibrosis in a subject in need of treatment for Hermansky Pudlak Syndrome (HPS), the method comprising administering an agonist of Rab32/38 or an inhibitor of CRTH2 to the subject.

3. The method of claim 1, wherein the subject is a subject identified as having an increased level of CHI3L1 expression and/or activity.

4. A method of treatment for pulmonary fibrosis in a subject with Hermansky Pudlak Syndrome, the method comprising;
    measuring the level of CHI3L1 in a test sample obtained from a subject;
    treating the subject with a pulmonary fibrosis treatment when the level of CHI3L1 is increased relative to a reference level; and
    not treating the subject with a pulmonary fibrosis treatment when the level of CHI3L1 is not increased relative to a reference level;
    wherein the pulmonary fibrosis treatment is an agonist of Rab32/38 or an inhibitor of CRTH2.

5. The method of claim 4, wherein the sample obtained from the subject is a blood or plasma sample.

6. The method of claim 4, wherein a detectable signal is generated by a CHI3L1-specific reagent when a CHI3L1 molecule is present.

7. The method of claim 6, wherein the CHI3L1-specific reagent is detectably labeled or capable of generating a detectable signal.

8. The method of claim 1, wherein the inhibitor of CRTH2 is selected from the group consisting of:
    OC-459; AZD-1981; Setipiprant; QAW-039; QAV-680; MK-7246; ADC-3680; BI671800; ARRY-502; RG-7581; AZD-5985; AZD-8075; AM461; AM211; AMG-853; PGD$_2$; AM432; CAY-10471; TM-30089; TM-30643; TM-30642; Ramatroban; and OC000459.

9. The method of claim 4, wherein the level of CHI3L1 is measured by measuring the level of a nucleic acid.

10. The method of claim 9, wherein the level of CHI3L1 is measured by measuring the level of CHI3L1 RNA transcript.

11. The method of claim 10, wherein the level of the nucleic acid is measured using a method selected from the group consisting of:
    RT-PCR; quantitative RT-PCR; Northern blot; microarray based expression analysis; next-generation sequencing; and RNA in situ hybridization.

12. The method of claim 4, wherein the level of CHI3L1 is measured by measuring the level of CHI3L1 polypeptide.

13. The method of claim 12, wherein the level of the polypeptide is determined using a method selected from the group consisting of:
    Western blot; immunoprecipitation; enzyme-linked immunosorbent assay (ELISA); radioimmunological assay (RIA); sandwich assay; fluorescence in situ hybridization (FISH); immunohistological staining; radioimmunometric assay; immunofluoresence assay; mass spectroscopy; FACS; and immunoelectrophoresis assay.

14. The method of claim 12, wherein the polypeptide level is measured using an antibody reagent.

15. The method of claim 14, wherein the antibody reagent is detectably labeled or generates a detectable signal.

16. The method of claim 4, wherein the expression level of CHI3L1 is normalized relative to the expression level of one or more reference genes or reference proteins.

17. The method of claim 4, wherein the reference level of CHI3L1 is the expression level of CHI3L1 in a prior sample obtained from the subject.

* * * * *